US012759678B2

(12) United States Patent
Sheldon-Coulson et al.

(10) Patent No.: US 12,759,678 B2
(45) **Date of Patent: *Oct. 13, 2026**

(54) CHEMICAL COLLECTION AND PROCESSING VESSEL AND METHODS FOR FLUID TRANSFER AT SEA

(71) Applicant: Lone Gull Holdings, Ltd., Portland, OR (US)

(72) Inventors: Garth Alexander Sheldon-Coulson, Portland, OR (US); Brian Lee Moffat, Portland, OR (US); Dominic Piro, Honolulu, HI (US)

(73) Assignee: Lone Gull Holdings, Ltd., Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/270,086

(22) Filed: Jul. 15, 2025

(65) Prior Publication Data

US 2025/0340275 A1 Nov. 6, 2025

Related U.S. Application Data

(63) Continuation of application No. 18/789,494, filed on Jul. 30, 2024, now Pat. No. 12,391,344, which is a (Continued)

(51) Int. Cl.
*B63B 35/44* (2006.01)
*B63B 27/34* (2006.01)
*C07C 29/152* (2006.01)

(52) U.S. Cl.
CPC .............. *B63B 35/44* (2013.01); *B63B 27/34* (2013.01); *C07C 29/152* (2013.01); *B63B 2035/4486* (2013.01)

(58) Field of Classification Search
CPC ....... C07C 29/152; C07C 31/04; B63B 35/44; B63B 27/34; B63B 2035/4486; Y02E 10/30
See application file for complete search history.

(56) References Cited

U.S. PATENT DOCUMENTS 5,710,464 A 1/1998 Kao et al.
7,715,516 B2 5/2010 Smith et al.
(Continued)

FOREIGN PATENT DOCUMENTS

WO 2022046472 A2 3/2022

OTHER PUBLICATIONS

Office Action for U.S. Appl. No. 18/652,647, dated Sep. 6, 2024, 16 pages.

(Continued)

*Primary Examiner* — Jafar F Parsa
(74) *Attorney, Agent, or Firm* — Schwabe, Williamson & Wyatt, P.C.

(57) ABSTRACT

Embodiments disclosed herein include a vessel for floating and traveling adjacent to an upper surface of a body of water. In an embodiment, the vessel comprises a support structure, a first floatation chamber coupled to the support structure, a second floatation chamber coupled to the support structure, the second floatation chamber laterally spaced apart from and fluidly coupled to the first floatation chamber, and a third floatation chamber coupled to the support structure, the third floatation chamber laterally spaced apart from the first floatation chamber and from the second floatation chamber. In an embodiment, the vessel further comprises a robot system coupled to the support structure, where the robot system comprises an end effector and a nozzle head coupled to the end effector.

14 Claims, 31 Drawing Sheets

Related U.S. Application Data continuation of application No. 18/438,077, filed on Feb. 9, 2024, now Pat. No. 12,077,259.

(60) Provisional application No. 63/446,236, filed on Feb. 16, 2023.

(56) References Cited

U.S. PATENT DOCUMENTS

| | | | |
|---|---|---|---|
| 2009/0281480 | A1 | 11/2009 | Orlebeke |
| 2010/0320759 | A1 | 12/2010 | Lightfoot |
| 2011/0155039 | A1 | 6/2011 | Moore |
| 2012/0011050 | A1 | 1/2012 | Lambert |
| 2018/0071675 | A1 | 3/2018 | Eisamen et al. |
| 2019/0186459 | A1 | 6/2019 | Skjoldhammer |
| 2021/0354791 | A1 | 11/2021 | Sheldon-Coulson |

OTHER PUBLICATIONS

Office Action for U.S. Appl. No. 18/652,652, dated Sep. 6, 2024, 14 pages.

International Search Report and Written Opinion from PCT/US2024/015431 dated Jun. 13, 2024, 14 pgs.

International Preliminary Report on Patentability from PCT/US2024/015431 dated Aug. 28, 2025, 11 pgs.

First Examination Report from Chilean Patent Application No. 202502191 dated Jul. 2, 2026, 25 pgs.

CHEMICAL COLLECTION AND PROCESSING VESSEL AND METHODS FOR FLUID TRANSFER AT SEA

CROSS-REFERENCE TO RELATED APPLICATIONS

This application is a Continuation of U.S. patent application Ser. No. 18/789,494, filed on Jul. 30, 2024, which is a Continuation of U.S. patent application Ser. No. 18/438,077, filed on Feb. 9, 2024, now U.S. Pat. No. 12,077,259, issued on Sep. 3, 2024, which claims the benefit of U.S. Provisional Patent Application No. 63/446,236, filed on Feb. 16, 2023, the entire contents of which are hereby incorporated by reference herein.

BACKGROUND

A buoyant, wave energy conversion (WEC) device is best deployed in a location where ocean waves are found. In the absence of a subsea electrical cable to carry its energy to shore, the energy a WEC extracts from ocean waves must either be used at sea to perform work there, or else be converted into a chemical fuel so that it may be transported to land and used by consumers there. Producing chemical fuels at sea requires a low-cost and efficient infrastructure to synthesize, collect, and transport to shore, those chemical fuels.

SUMMARY OF THE INVENTIONS

Disclosed is a novel type of ocean-going vessel configured to:

1) collect liquids, gasses and/or other chemical products from a wave energy conversion (WEC) apparatus (or other oceanic platform) via a transfer apparatus, and store and/or process said liquids, gasses and/or other chemical products based on the specific mission of the embodiment;
2) when at rest, to drift adjacent to an upper surface of a body of water over which waves pass in a manner similar to that of a WEC from which it retrieves chemical products, thereby reducing the likelihood of complications such as those that might arise during an attempt to couple two vessels moving out of phase as they oscillate in response to the passage of waves;
3) deliver collected and/or or synthesized chemical products to shore, to other vessels and/or to other platforms, and/or reintroduce portions of synthesized chemical products back into the environment as dictated by the specific mission of the embodiment.

Herein disclosed is a vessel that tends to drift adjacent to a moving upper surface of a body of water in a fashion similar to that of a free-floating WEC, while also possessing a capability to retrieve, store, and/or process liquids, gasses and other chemical products obtained from a WEC. The vessel disclosed herein permits a significant simplification of an otherwise inherently complex process and/or infrastructure, and is expected to thereby significantly reduce cost of that infrastructure and/or the execution of that process.

The storage and transportation of gases tends to require a compression of those gases in order to increase the density of material to be stored and transported. However, compression consumes additional energy. And compressed gases must be stored in strong vessels that won't break or leak and those vessels tend to be relatively expensive. By contrast, the storage and transportation of liquids tends to be relatively simple and inexpensive.

Embodiments of the vessel disclosed herein permit and facilitate the alteration, e.g. from gases to liquids, of chemical products retrieved from WECs, prior to the transportation of those altered and/or reconfigured chemical products. This enables a significant increase in the efficiency with which energy and/or valuable chemicals can be gathered from the sea and the benefit of that energy and/or those valuable chemicals shared with consumers on land.

An embodiment of the vessel disclosed herein retrieves from WECs both hydrogen gas (H2) and aqueous hydrochloric acid solution (HCl). The embodiment uses the HCl in order to facilitate its extraction of carbon dioxide (CO2) from seawater. And, finally, it reacts the H2 and the CO2 in order to synthesize liquid green (i.e. made from renewable sources) methanol (CH3OH) which it then transports to shore or provides to other vessels for consumption or transportation to shore.

Another embodiment of the vessel disclosed herein also retrieves from WECs both hydrogen gas (H2) and aqueous hydrochloric acid solution (HCl). However, this embodiment uses the H2 to generate electrical power. And, it uses that electrical power to retrieve and store the HCl, and to then move, and/or transport, the HCl to deep subsurface waters via a hose or a lowered tank, thereby reducing acidity at the surface of the body of water on which it floats, and thereby allowing ancient calcareous deposits, and/or deep, relatively alkaline water, to neutralize and/or dilute that acid immediately instead of the process that would tend to naturally occur over the course of millennia.

Also disclosed are methods for making a fluid connection and achieving the transfer of fluids from a first floating body (e.g. a WEC) to a second floating body (e.g. an embodiment of the tripod vessel disclosed herein) using a cable robot integral to and controlled by the second floating body and associated hoses and pipes.

While the present disclosure focuses on the use and benefits of the disclosed vessels with respect to the retrieving, storing, processing, and/or sequestering (at depth) of liquids, gasses and/or any contents offloaded from a WEC, similar vessels to those disclosed herein will have utility and benefits with respect to the offloading, storing, processing, synthesis using, and/or sequestering of liquids, gasses and or any chemical products collected at sea, or upon any large body of water, from devices other than WECs, and the scope of the present disclosure includes, but is not limited to, all such other embodiments of the disclosed technologies.

DETAILED DESCRIPTION OF THE PREFERRED EMBODIMENTS

Figure 1:
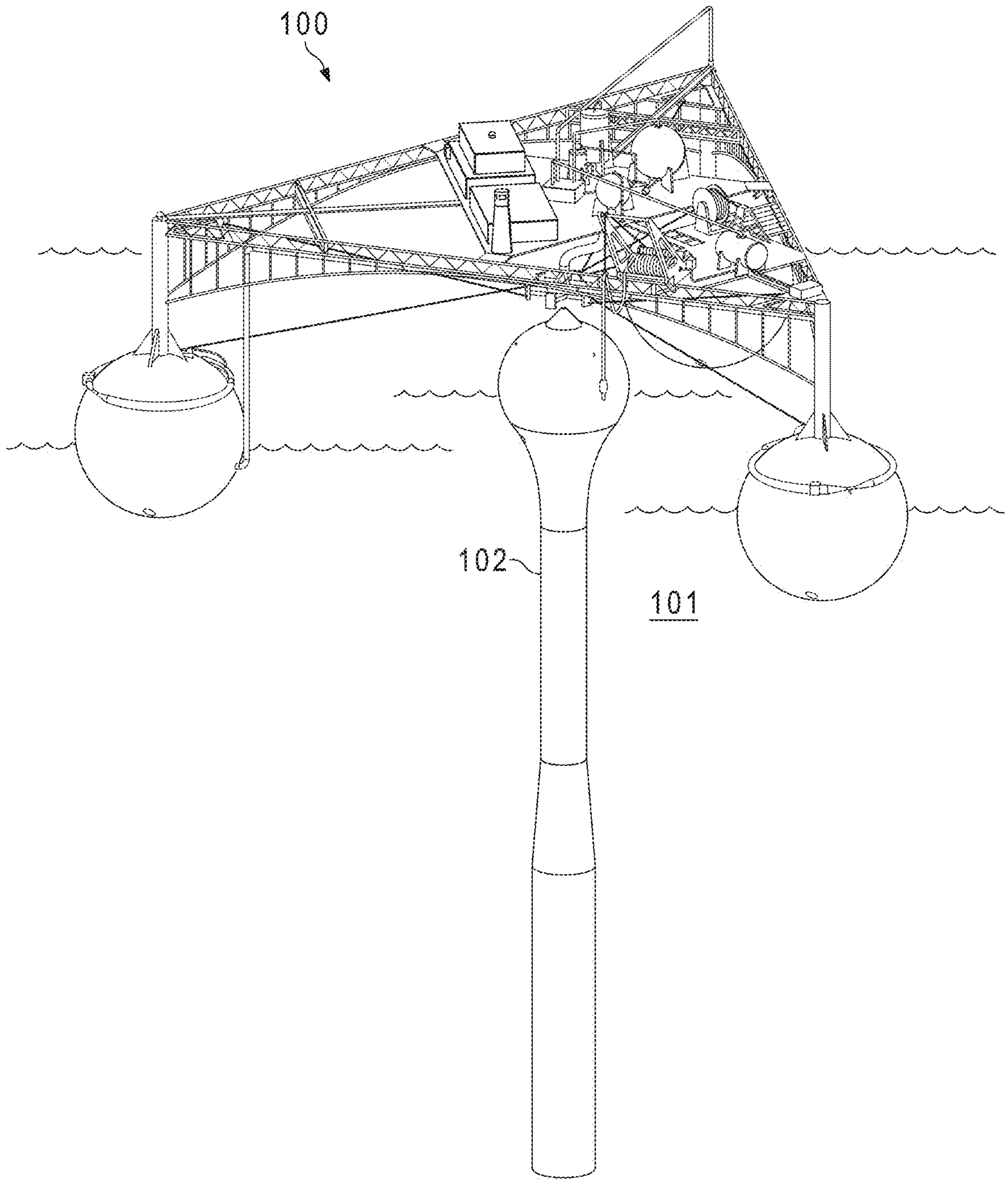
FIG. 1 is a perspective side view of a first embodiment of a collection vessel of the present invention.

For a fuller understanding of the nature and objects of the invention, reference should be made to the preceding Summary of the Invention, taken in connection with the following figures, the illustrations offered therein, and their associated figure descriptions. The following figures, and their associated figure descriptions, offer explanatory illustrations. The following figures, the illustrations offered therein, and their associated figure descriptions, in no way constitute limitations, either explicit or implicit, on and/or of the present invention.

In some implementations, the different embodiments are practiced separately. However, embodiments are not limited to embodiments being practiced in isolation. For example, two or more different embodiments can be combined together in order to be practiced as a single device, process, structure, or the like. The entirety of various embodiments can be combined together in some instances. In other instances, portions of a first embodiment can be combined with portions of one or more different embodiments. For example, a portion of a first embodiment can be combined with a portion of a second embodiment, or a portion of a first embodiment can be combined with a portion of a second embodiment and a portion of a third embodiment.

The embodiments illustrated and discussed in relation to the figures included herein are provided for the purpose of explaining some of the basic principles of the disclosure. However, the scope of this disclosure covers all related, potential, and/or possible, embodiments, even those differing from the idealized and/or illustrative examples presented. This disclosure covers even those embodiments which incorporate and/or utilize modern, future, and/or as of the time of this writing unknown, components, devices, systems, etc., as replacements for the functionally equivalent, analogous, and/or similar, components, devices, systems, etc., used in the embodiments illustrated and/or discussed herein for the purpose of explanation, illustration, and example.

As used herein, “fluidly connected” may refer to two components that are configured to allow for the transfer of one or more fluids (e.g., gas and/or liquid) between the two components. For example, a first chamber may be fluidly connected to a second chamber, when a gas from the first chamber is capable of flowing (either actively (e.g., through pumping) or passively (e.g., through pressure differentials)) from the first chamber to the second chamber and/or from the second chamber to the first chamber. Fluidly connected components may be directly connected to each other. That is, there may not be any intervening components between the first component and the second component. In other instances, one or more additional intervening components (e.g., pipes, valves, chambers, reactors, etc.) may be provided between the first component and the second component so long as the one or more fluids are capable of being transferred between the first chamber and the second chamber along a path that includes the one or more intervening components. Additionally, while “components” may be fluidly connected with each other, the concept of fluidic connections is not limited to structures such as chambers, containers, and the like. That is, a first volume of a liquid or gas may be fluidly connected to a second volume of a liquid or gas even if one or both of the first volume and the second volume are not confined by any specific structure. For example, a volume of fluid within a chamber may be fluidly connected to a generally unconfined volume (e.g., a body of water or the atmosphere surrounding the chamber) through a pipe, tube, port, opening or other passage through a surface of the chamber.

FIG. 1 shows a side perspective view of an embodiment 100 of the current disclosure.

The disclosed vessel 100 floats and travels adjacent to an upper surface of a body of water 101 for the purpose of coupling with and offloading chemical products from WECs 102 that have been deployed at sea for a period of time, and thereafter storing, utilizing, processing, and/or sequestering said chemical products.

Figure 2:
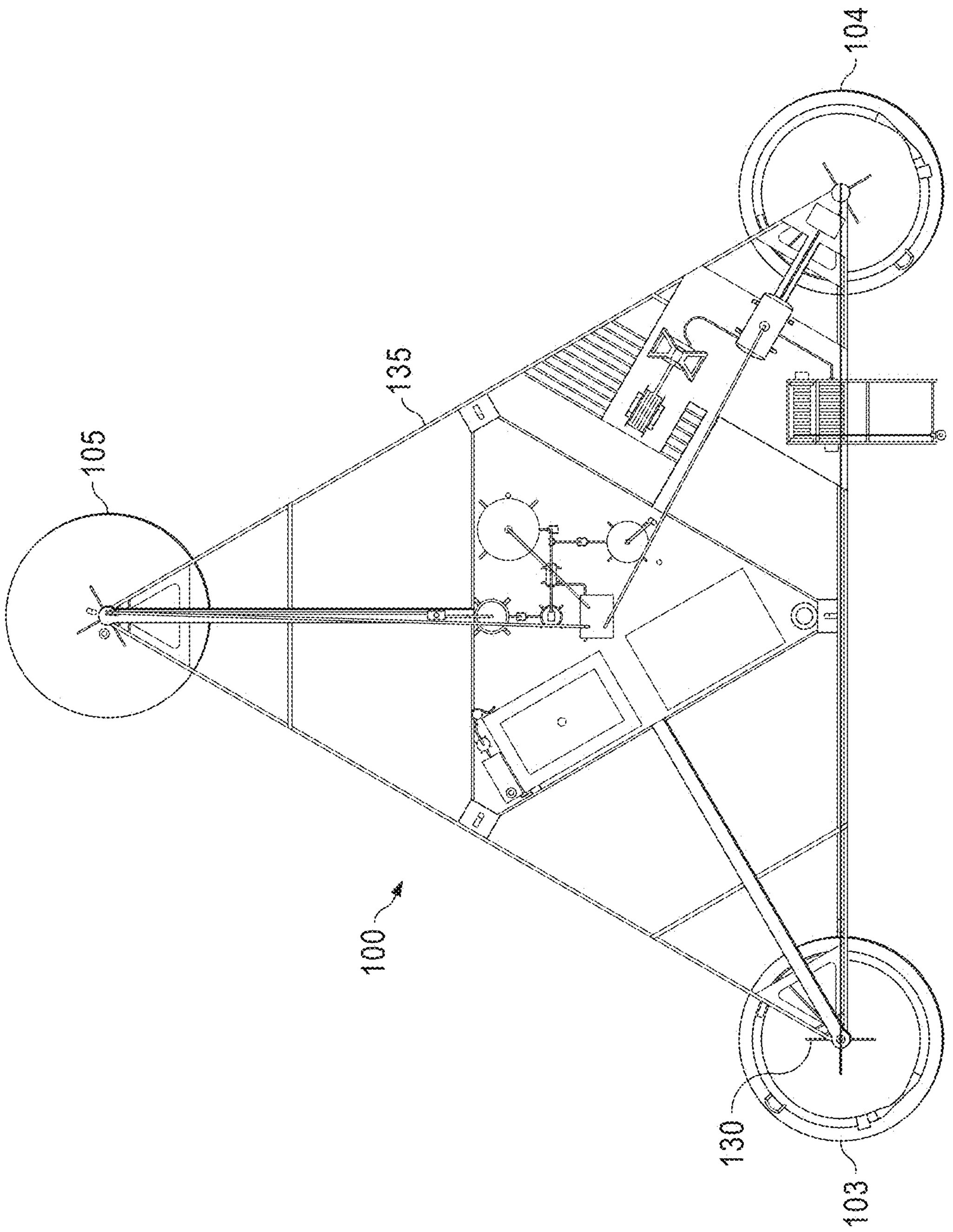
FIG. 2 is a top-down view of the first embodiment.

FIG. 2 shows a top-down view of the same embodiment 100 of the present disclosure that is illustrated in FIG. 1.

Three flotation spheres (a first degassing sphere 103, a second degassing sphere 104, and a methanol ballast sphere 105) are connected to the primary structure of the vessel 100 by a plurality of beams, trusses, girders and like structure 130. While referred to herein as "spheres", it is to be appreciated that the first degassing sphere 103, the second degassing sphere 104, and the methanol ballast sphere 105 may comprise any shaped chamber. For example, a first degassing chamber 103, a second degassing chamber 104, or a methanol ballast chamber 105 may comprise spherical chambers, spherical cap chambers, rectangular chambers, pyramid shaped chambers, frustum shaped chambers, oblong chambers, or the like. The chambers 103, 104, and/or 105 may be symmetric about one or more axes. The chambers 103, 104, and/or 105 may be asymmetric about one or more axes. The upper deck 135 of the vessel is comprised of a latticework of beams, trusses, girders, and structure that provide a platform upon which are mounted and/or affixed chemical storage and processing facilities, equipment, and/or mechanisms, including, but not limited to, tanks and equipment utilized, respectively, for the storage of H2 and HCl retrieved from WECs, and for the extraction from seawater of CO2, as well as the processing of H2 and CO2 in order to synthesize methanol (CH3OH).

Figure 3:
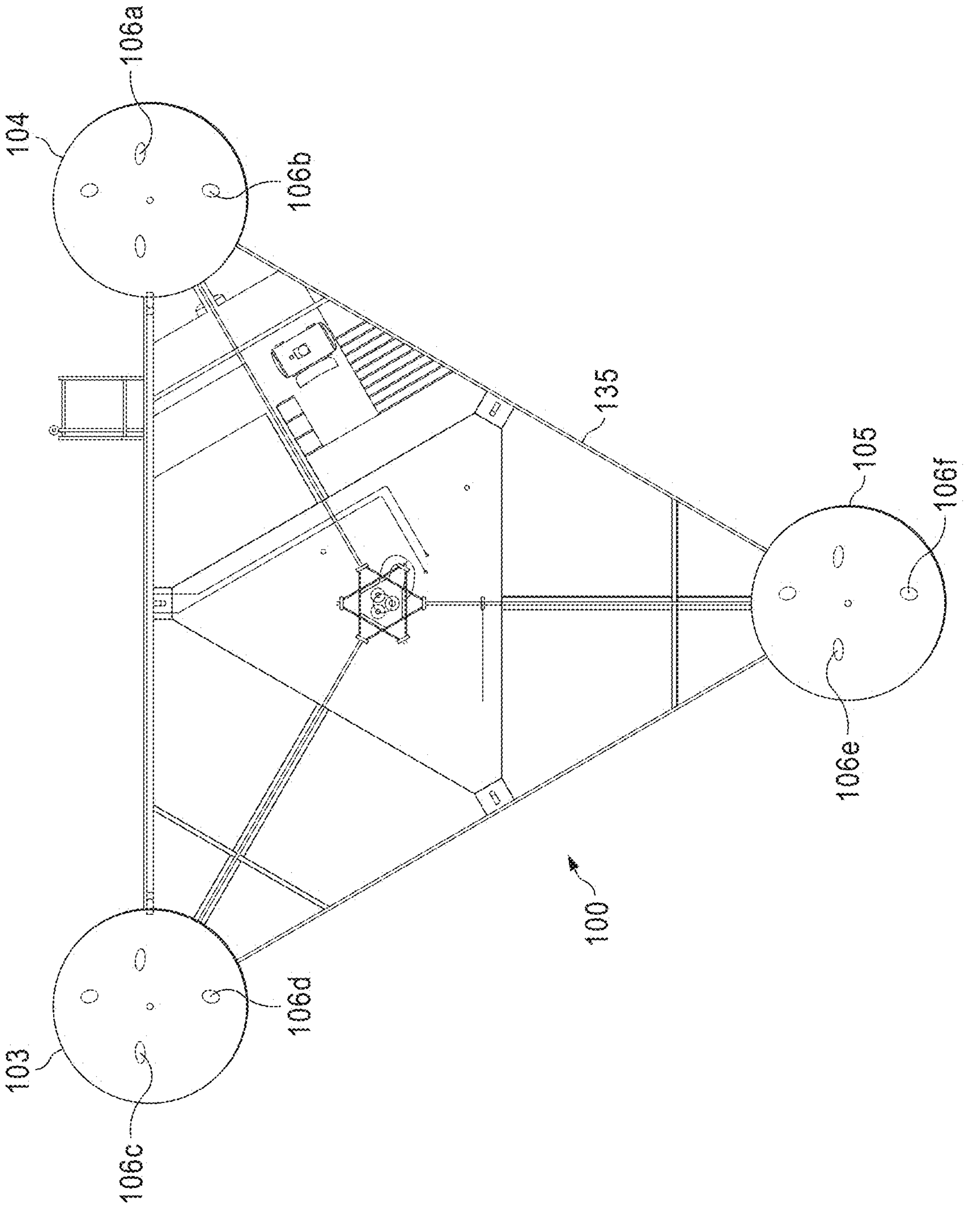
FIG. 3 is a bottom-up view of the first embodiment.

FIG. 3 shows a bottom-up view of the same embodiment 100 of the present disclosure that is illustrated in FIGS. 1 and 2. Each of the first 103 and second 104 degassing spheres, and the methanol ballast sphere 105, includes two directional thrusters, propellers, water jets or other propulsion mechanisms, 106*c* and 106*d*, 106*a* and 106*b*, and 106*e* and 106*f*, respectively, for the purposes of propelling and steering the vessel across bodies of water. Each such thruster is mounted within a nominally submerged tunnel within one of the said spheres.

Figure 4:
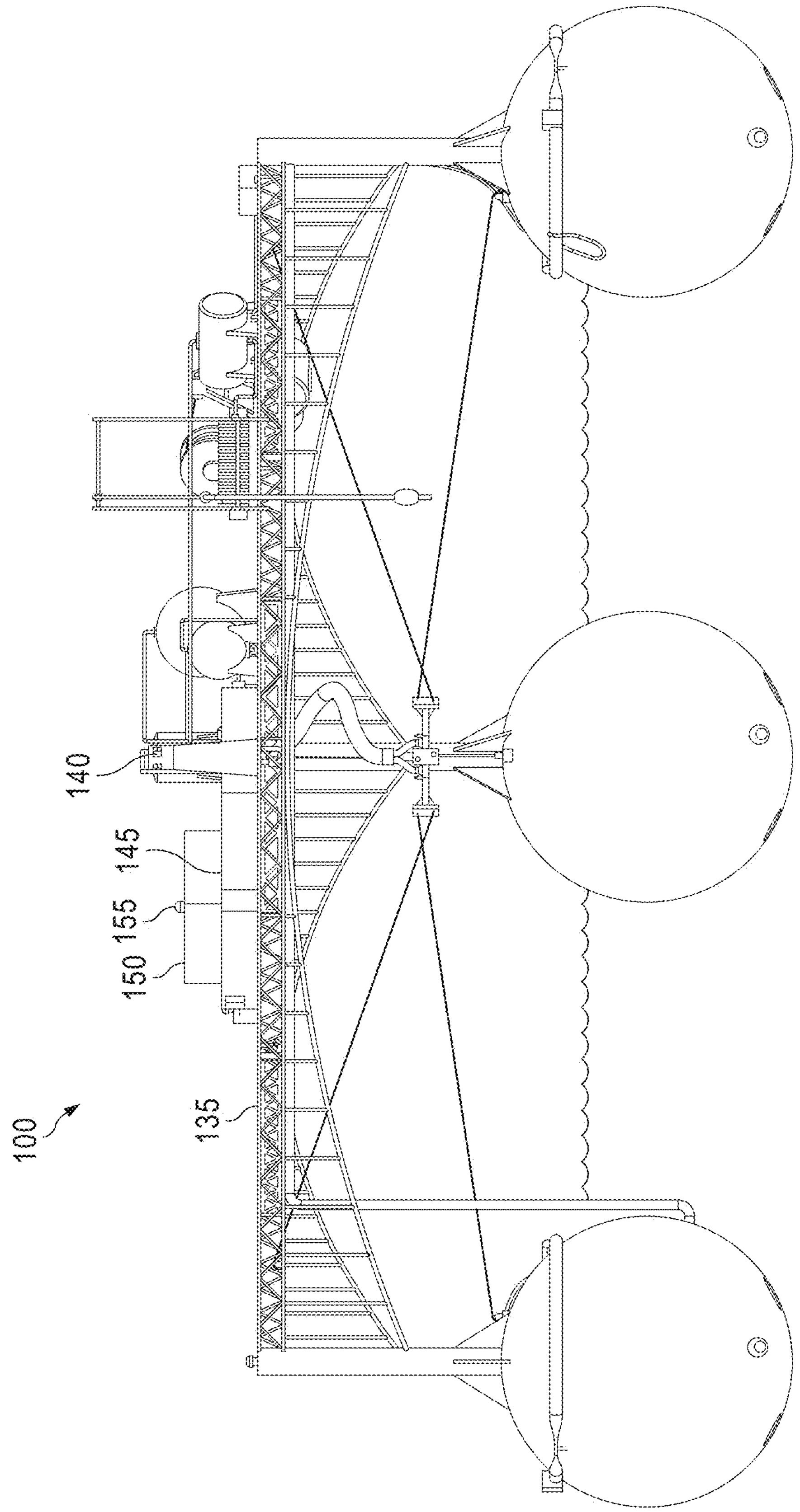
FIG. 4 is a side view of the first embodiment.

FIG. 4 shows a side view of the same embodiment 100 of the present disclosure that is illustrated in FIGS. 1-3. The upper deck 135 includes a bridge or control station 140, spaces for a housing of crew 145, and a structure 150 for accommodating electronic equipment for the purposes of navigation, communications, and for control of onboard chemical synthesizing and/or processing equipment. Some embodiments of the present disclosure may be remotely or autonomously controlled and require no human crew. A plurality 155 of antenna, transmitters, dishes, aerials, and/or receivers, are mounted and/or affixed to the vessel in order to support and/or enable the embodiment's navigational and communications systems.

Figure 5:
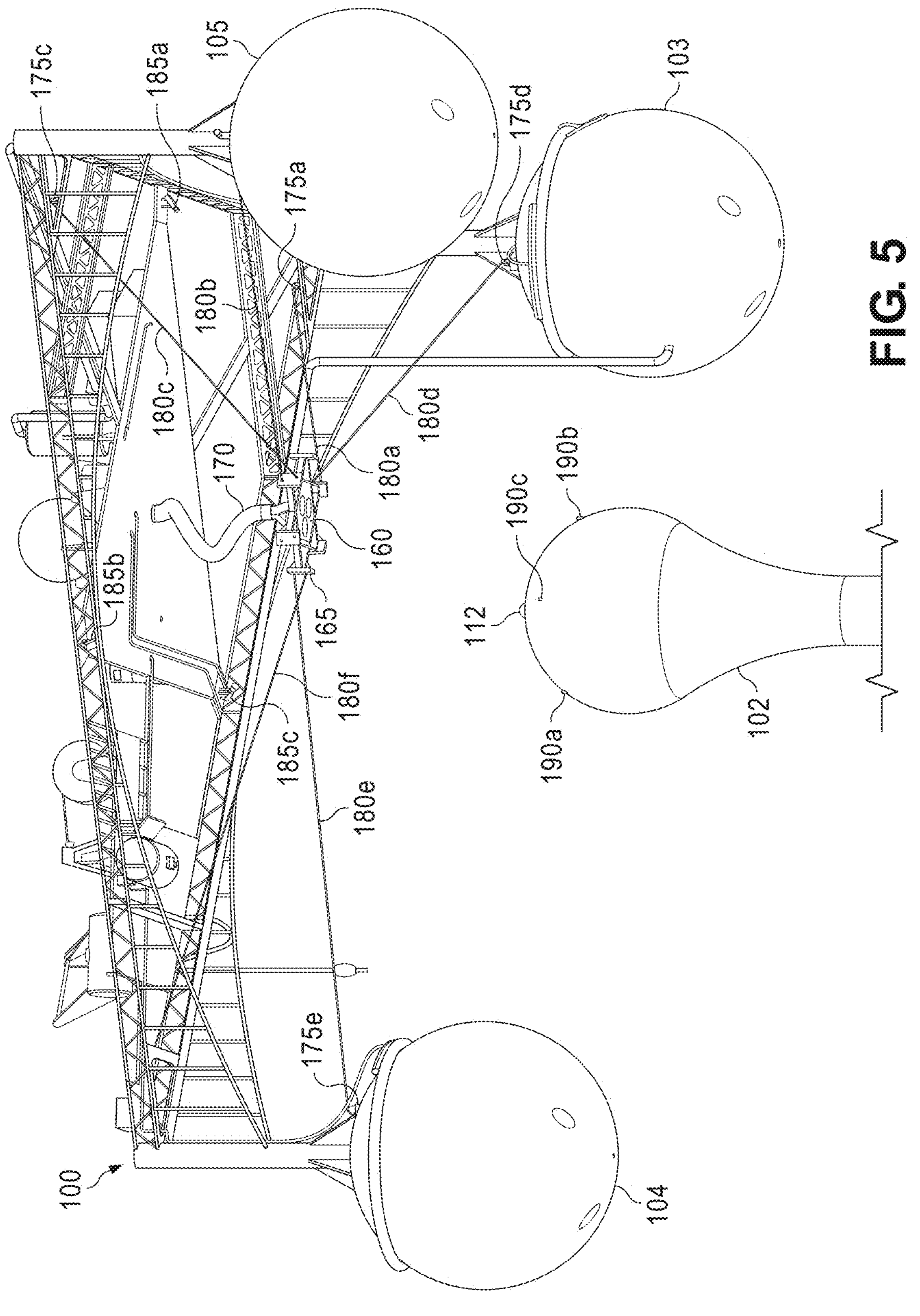
FIG. 5 is perspective bottom-up view of the first embodiment.

FIG. 5 shows a perspective bottom-up view of the underside of the same embodiment 100 of the present disclosure that is illustrated in FIGS. 1-4, with the lower portion of the WEC 102 not shown.

A cable robot system provides a means and/or mechanism which enables the embodiment to fluidly connect to, and to offload fluid contents from, a WEC 102 positioned approximately beneath the embodiment adjacent to a surface of the same body of water.

The cable robot system is comprised of a nozzle head 160, which is situated on an underside of an end effector 165, a composite hose 170, six coiling winch motors 175*a*-*f* (175*b* and 175*f* not visible and shown elsewhere), six control cables 180*a*-*f*, three cameras 185*a*-*c*, and a plurality of computational electronics (not shown). Three of the coiling winch motors 175*a*-*c* are attached to an underside of the upper deck of the embodiment 100, and three coiling winch motors 175*d*-*f* are respectively attached to each of the embodiment's spheres (i.e. to the first 103 and second 104 degassing spheres, and to the methanol ballast sphere 105). Each coiling winch motor, e.g. 175*a*, is attached to and controls the effective length of a control cable, e.g. 180*a*, one end of which is secured to the end effector 165. The nozzle head 160 is further connected to composite hose 170 wherethrough fluid and/or gaseous chemical products of a WEC are retrieved and/or removed from the WEC when the nozzle head 160 is engaged with, and/or fluidly connected to, the WEC offloading nozzle 112. Target nodes 190*a*-*c* on the WEC 102 allow an optical and/or visual location tracking of an orientation and/or position of the WEC 102 relative to the nozzle head 160 via cameras 185*a*-*c* and associated computational electronics thereby tending to facilitate a coupling the nozzle head 160 to the WEC's offloading nozzle 112. In some embodiments, control cables 180*a*-*f* are controlled by motors on the upper deck of those embodiments, with said control cables passing through sheaves disposed on the degassing and methanol ballast spheres and/or elsewhere to provide the requisite angles of the cables incident to the end effector 165.

Figure 6:
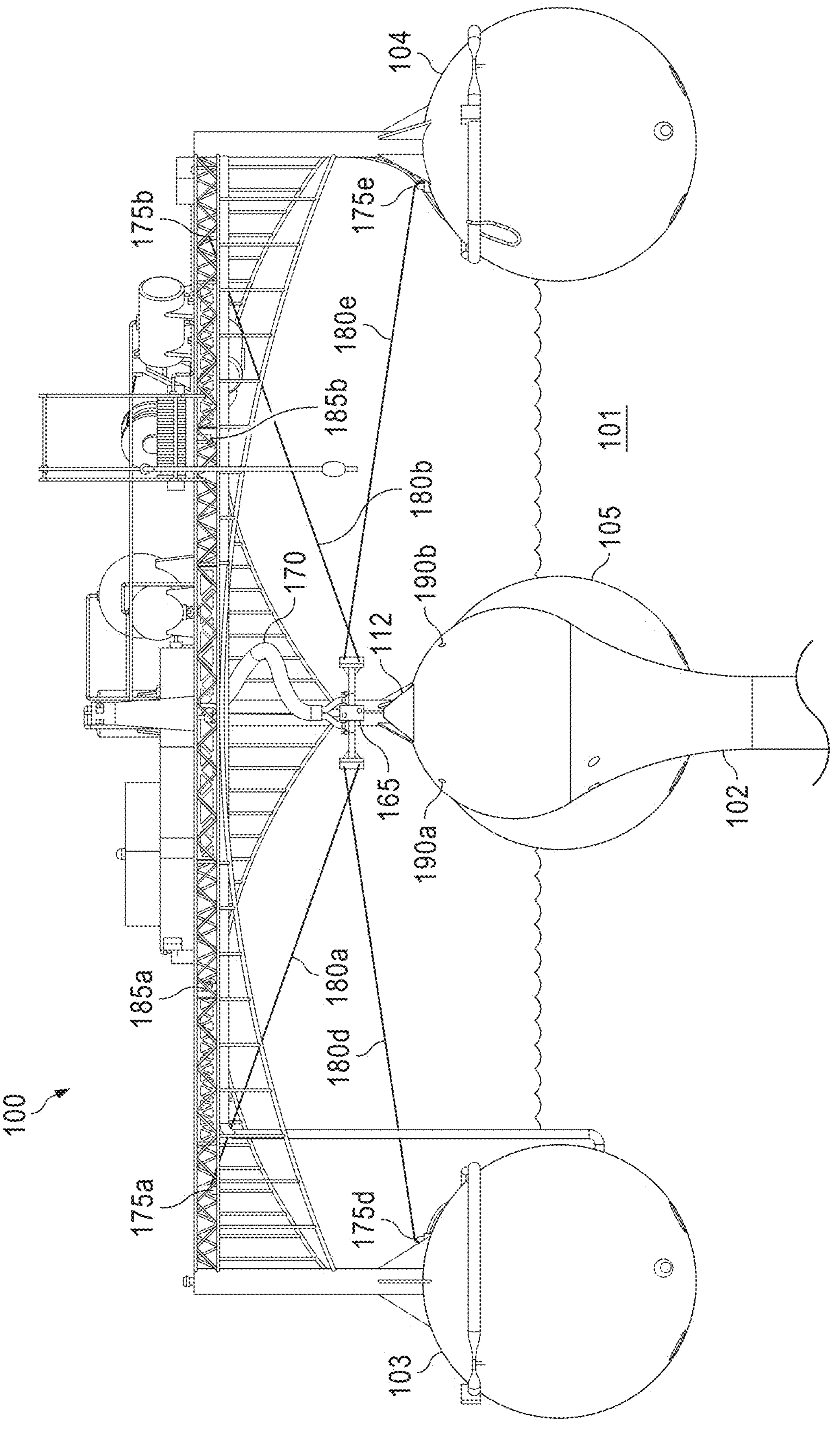
FIG. 6 is a side view of the first embodiment.

FIG. 6 shows a side view of the same embodiment 100 of the present disclosure that is illustrated in FIGS. 1-5, with the lower portion of WEC 102 not shown.

As the embodiment 100 approaches and positions itself over a WEC 102 in a body of water 101, three cameras 185*a*-*c* (185*c* is not visible and shown elsewhere) track target nodes 190*a*-*c* (190*c* is not visible and shown elsewhere) on the WEC 102. As the cameras 185*a*-*c* and associated computational electronics process data so as to determine and/or track a location of the WEC 102 relative to the embodiment's end effector 165, the end effector 165 is moved into a coupling position with the WEC 102 by means of control cables 180*a*-*f* (180*c* and 180*f* are not visible and shown elsewhere) and coiling winch motors 175*a*-*f* (175*c* and 175*f* are not visible and shown elsewhere.) Each cable, e.g. 180*a*, is retracted or allowed to extend by a respective coiling winch motor, e.g. 175*a*, controlled by a computational and control system programmed to control, move, and optimize, a location of the end effector 165 relative to the WEC 102 for the purpose of fluidly coupling the nozzle head 160 with the WEC nozzle 112.

As the WEC 102 and the embodiment 100 move and/or oscillate in response to passing ocean waves, data collected by cameras 185*a*-*c* is used in computations and/or calculations which continuously adjust the respective lengths of cables 180*a*-*f* via respective coiling winch motors 175*a*-*f*. The synchronized retractions and extensions of the control cables 180*a*-*f* move, position, and orient, the embodiment's end effector 165 and nozzle head 160 in six degrees of freedom so as to facilitate, enable, and/or realize, a coupling, and/or a fluid-connection, of the nozzle head to the WEC nozzle 112.

Each extension or retraction of a control cable, e.g. 180*a*, via a respective and/or paired coiling winch motor, e.g. 175*a*, is synchronized with appropriate extensions and/or retractions of one or more complimentary control cables, e.g. 180*a*-*f*, thereby tending to expeditiously move the end effector 165 and nozzle head 160 into a coupling position with the WEC's offloading nozzle 112, and to thereafter maintain that coupling position, even as the embodiment and the WEC move relative to one another. Computations informing the embodiment of proximities and locations of the WEC 102 and end effector 165 relative to one another, and of the embodiment relative to the WEC 102, provide a basis for a continuous alteration, adjustment, and/or control, of a position and/or orientation of the embodiment's end effector 165 via coiling winch motors 175*a*-*f* and control cables 180*a-f* until the nozzle head 160 is successfully fluidly coupled with the offloading nozzle 112 of the WEC.

In some embodiments, a mechanical locking mechanism on either or both of the respective embodiments' nozzle heads and/or respective WECs' offloading nozzles, is initiated and maintained when positive contact, and fluid connection, is confirmed, e.g. via a plurality of electronic sensors, between the respective nozzle heads and WEC offloading nozzles. Once fluidly coupled, a signal from such a nozzle locking mechanism can trigger the cable robot to enter a neutral or slack configuration, where the coiling winch motors 175*a-f* no longer impose significant tension nor significantly inhibit extension and retraction of the cables 180*a-f*. The coiling winch motors 175*a-f* and thereby cables 180*a-f* are allowed to move relatively freely with the movement of the WEC 102 during the offloading process.

Figure 7:
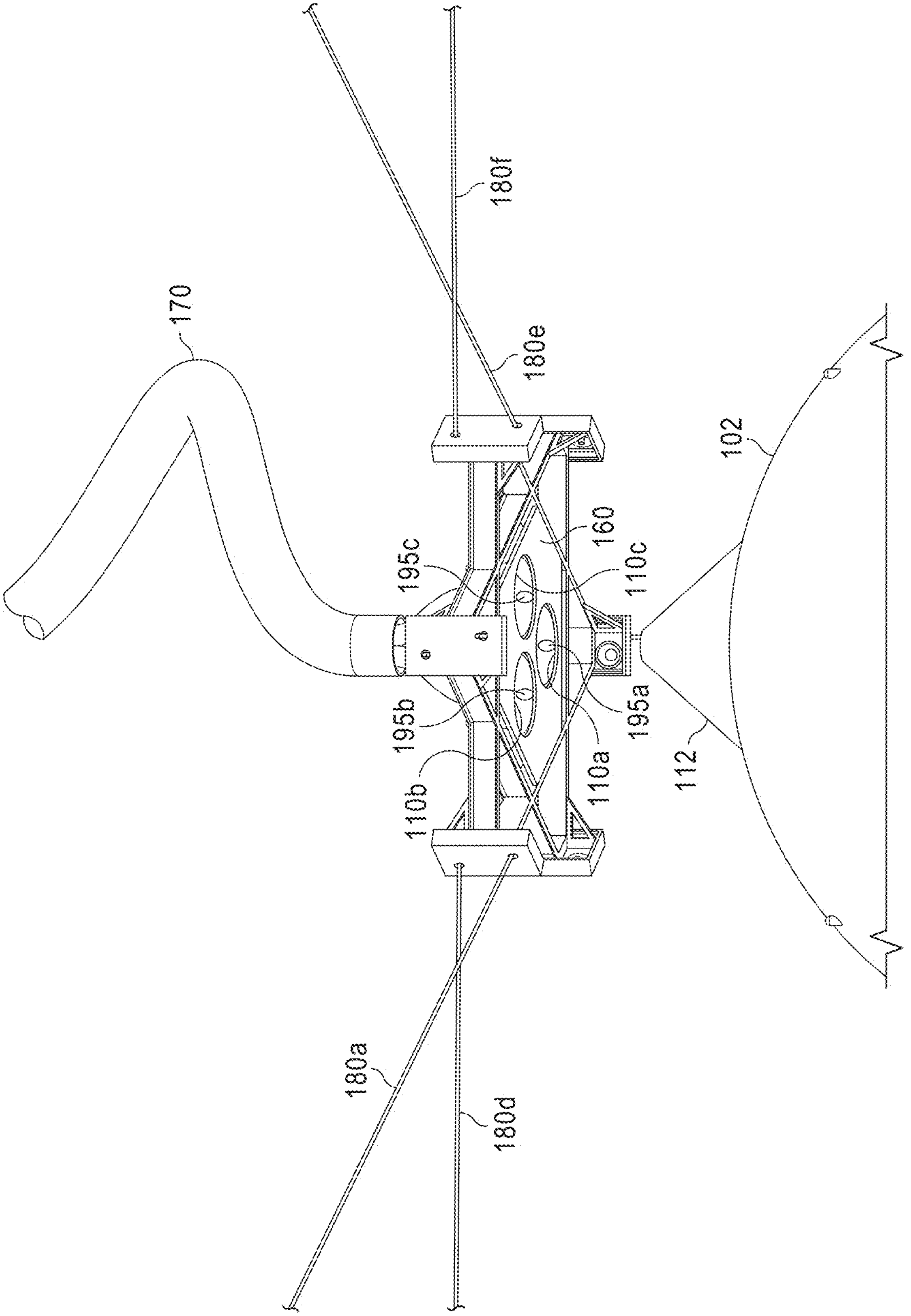
FIG. 7 is a detailed close-up partial perspective view of the first embodiment.

FIG. 7 shows a partial perspective bottom-up view of the lower side of the same embodiment of the present disclosure that is illustrated in FIGS. 1-6, with the majority of the embodiment not shown for clarity.

The nozzle head 160 is comprised of a plurality of ports 110*a-c* (each of which is fluidly connected to a respective hose incorporated within composite hose 170), one or more of which will fluidly connect with a respective one of a WEC's offloading nozzle ports 112 when the nozzle head 160 and WEC offloading nozzle 112 are engaged. Once coupled, an electronic signal initiated by positive engagement of electromagnetic lock, e.g. 195*a*, will trigger the cable robot to enter a neutral or slack configuration, whereby the coiling winch motors 175*a-f* (not visible and shown elsewhere) no longer impose tension nor inhibit extension and retraction of the cables 180*a-f* (180*c-d* are not visible and shown elsewhere) except to the extent required to prevent a cable from becoming slack. The coiling winch motors 175*a-f* (are not visible and shown elsewhere) and thereby the respective cables 180*a-f* are allowed to move more freely with the relative movement of the WEC 102 that tends to result in response to passing ocean waves during the offloading process. Having multiple ports 110*a-c* per nozzle head allows flexibility of offloading in that a single nozzle head 160 may be used to offload different chemical products from different WEC 102 types (i.e. WECs providing hydrochloric acid solution, H2, or some other liquid or gas) using the same embodiment.

In some embodiments, the cable robot will continue to process data as to the relative position and orientation of a WEC 102 to the nozzle head 160 and end effector 165 after coupling, thereby continually and actively adjusting the length and tension of cables 180*a-f* with coiling winch motors 175*a-f* during an offloading process in order to maintain engagement of the nozzle head 160 with the WEC offloading nozzle 112 during the offloading process.

Figure 8:
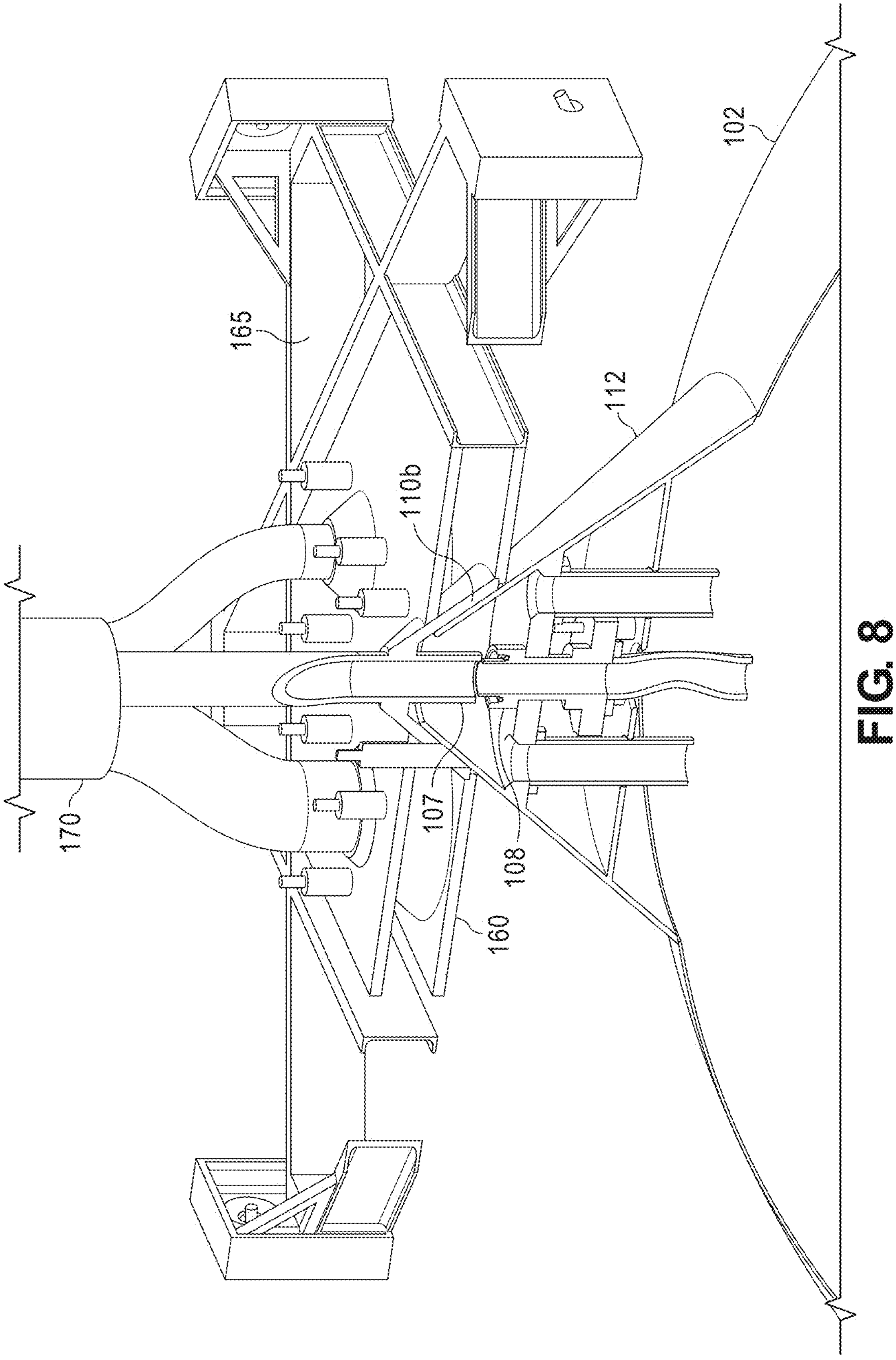
FIG. 8 is a detailed close-up partial perspective view of the first embodiment with some surfaces removed for clarity.

FIG. 8 shows a partial perspective side view of the end effector and nozzle head of the same embodiment of the present disclosure that is illustrated in FIGS. 1-7, with the majority of the embodiment not shown for clarity, and surfaces of the end effector 165 removed for clarity.

Nozzle head 160 comprises a tooling feature 107 (in addition to electromagnetic locks 195*a-c*, which are not visible and shown elsewhere) and a plurality of ports 110*a-c* (110*a* and 110*c* are not visible and shown elsewhere). Ports 110*a-c* are further connected to hoses that form part of composite hose 170, one or more of which will fluidly connect with a respective one or more of a WEC's offloading nozzles 112 when nozzle head 160 and WEC offloading nozzle 112 are engaged. In addition to electromagnetic locks, the engagement of the port 110*a-c* on nozzle head 160 and WEC offloading nozzle 112 is enabled by tooling feature 107 within nozzle head 160, and a tooling feature 108 on WEC offloading nozzle 112. As the nozzle head 160 begins to couple with WEC offloading nozzle 112 and is initially engaged by an electromagnetic lock, e.g. 195*b*, a tooling feature 107 will couple and lock the nozzle head 160 with a complimentary tooling feature 108 within the WEC offloading nozzle 112. This allows flexibility in that nozzle head 160 may be used to offload contents from different WEC 102 types (i.e. WECs providing hydrochloric acid solution, H2, or some other liquid or gas) using a single, same embodiment.

In some modes of operation, compressed gaseous H2 is offloaded from a WEC 102 via the WEC's offloading nozzle 112 and the vessel's 100 nozzle head 160. The nozzle head 160 comprises a plurality of ports (110*a-c*), one of which is specific for offloading H2 from a WEC 102. Once nozzle head 160 and WEC offloading nozzle 112 are coupled, and the tooling feature described previously has enabled and/or achieved positive engagement of the H2 ports on nozzle head 160 and WEC offloading nozzle 112, offloading of the H2 begins. H2 stored under pressure on the WEC will tend to flow through the ports that are engaged via nozzle head 160 and the WEC offloading nozzle 112. Composite hose 170 is routed to and connects to a pump and valve interface 144 (not visible and shown elsewhere) which routes H2 to H2 tank 155 (not visible and shown elsewhere). In some instances the gaseous H2 may be generated by the WEC through the conversion of wave energy into electrical energy (e.g., through the use of a turbine or the like). The electrical energy can be used to power an electrolyzer that converts water into H2 and O2. The H2 can be stored on the WEC and the 02 may be vented to the atmosphere.

Figure 9:
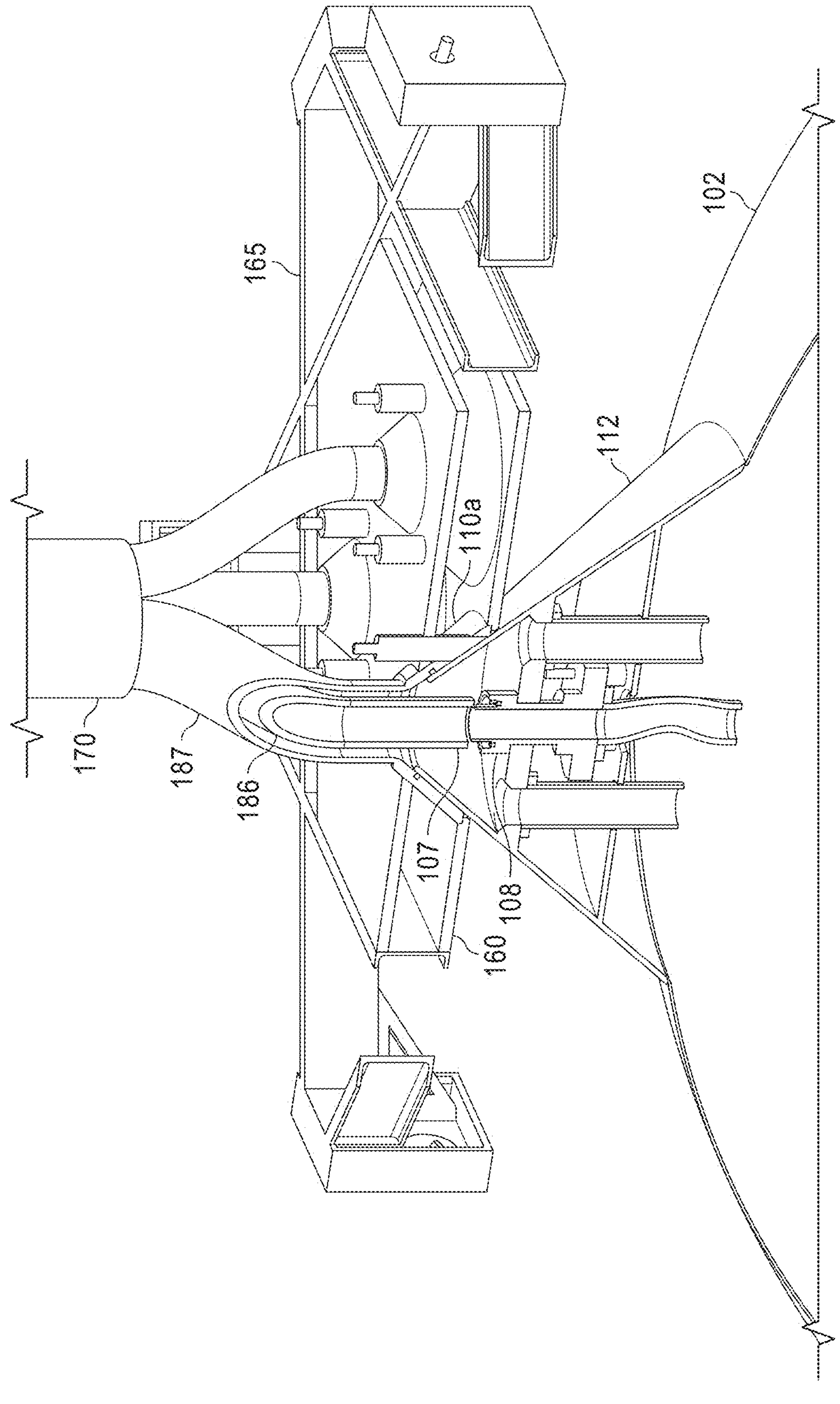
FIG. 9 is a detailed close-up partial perspective view of the first embodiment with some surfaces removed for clarity.

FIG. 9 shows a partial perspective view of the end effector and nozzle head of the same embodiment of the present disclosure that is illustrated in FIGS. 1-8, with the majority of the embodiment not shown for clarity, and portions of the end effector 165 removed for clarity.

In some modes of operation, a liquid and/or aqueous hydrochloric acid solution (HCl) is offloaded from a WEC 102 via the WEC's offloading nozzle 112 and the embodiment's nozzle head 160. The nozzle head 160 comprises a plurality of ports 110*a-c* (110*b* and 110*c* are not visible and shown elsewhere), one of which further comprises two tubes (one tube 186, of a smaller diameter, coaxially disposed within another tube 187, of a larger diameter) which are specific for offloading HCl from the WEC 102. Once nozzle head 160 and WEC offloading nozzle 112 are fluidly coupled, and the tooling feature 107 and tooling feature 108 described previously has enabled positive engagement of the HCl-specific port 110*a*, offloading of the HCl begins. In some instances the HCl may be generated by the WEC through the reaction of H2 gas and Cl2 gas stored on the WEC. The H2 gas and/or the Cl2 gas may be generated through electrolysis using electrical energy from the conversion of wave energy. The H2 gas and the Cl2 gas can be reacted to form HCl in an exothermic reaction, and the HCl may be stored on the WEC. Cl2 may also be generated through pumped osmosis techniques, or the Cl2 may be stored on the WEC as a precursor that is periodically replenished.

Water is forced down inner tube 186 by means of a pump and valve interface 144 (not visible and shown elsewhere). As water moves down through inner tube 186 of the composite hose 170, through the engaged nozzle head 160 port, through WEC offloading nozzle 112 port, and into the WEC, the downward force of the water forces HCl within a circuitous tank on the WEC 102 to be pushed up through outer tube 187 of the composite hose 170 via the engaged port on the WEC offloading nozzle 112 and the nozzle head 160. The HCl is pushed up composite hose 170 which is routed to and connects to a pump and valve interface 144 (not visible and shown elsewhere), which in turn routes the HCl to HCl storage tank 143 (not visible and shown elsewhere), whereby the HCl is stored until such a time that it is used for a chemical process, offloaded to another ship, or sequestered in deep water, sequestration occurring either immediately, or after a determined amount of HCl has been collected and stored aboard the embodiment.

Once chemical products, and/or a sufficient quantity of chemical products, of a WEC 102 are offloaded, nozzle head 160 is decoupled from the WEC's offloading nozzle 112 by means of an automated release switch (not shown) which in turn signals the cable robot to re-tension control cables 180*a-f* with the respective coiling winch motors 175*a-f*. The end effector 165 is then moved thereby to a stowed position, approximately centered under the embodiment until such time as the embodiment settles over another WEC for coupling and offloading.

An alternate embodiment utilizes, incorporates, and/or includes, a nozzle head 160 that is further comprised of a port and hose for transferring CH3OH synthesized aboard the embodiment to another vessel for eventual transport to a land-based storage and distribution facility.

Figure 10:
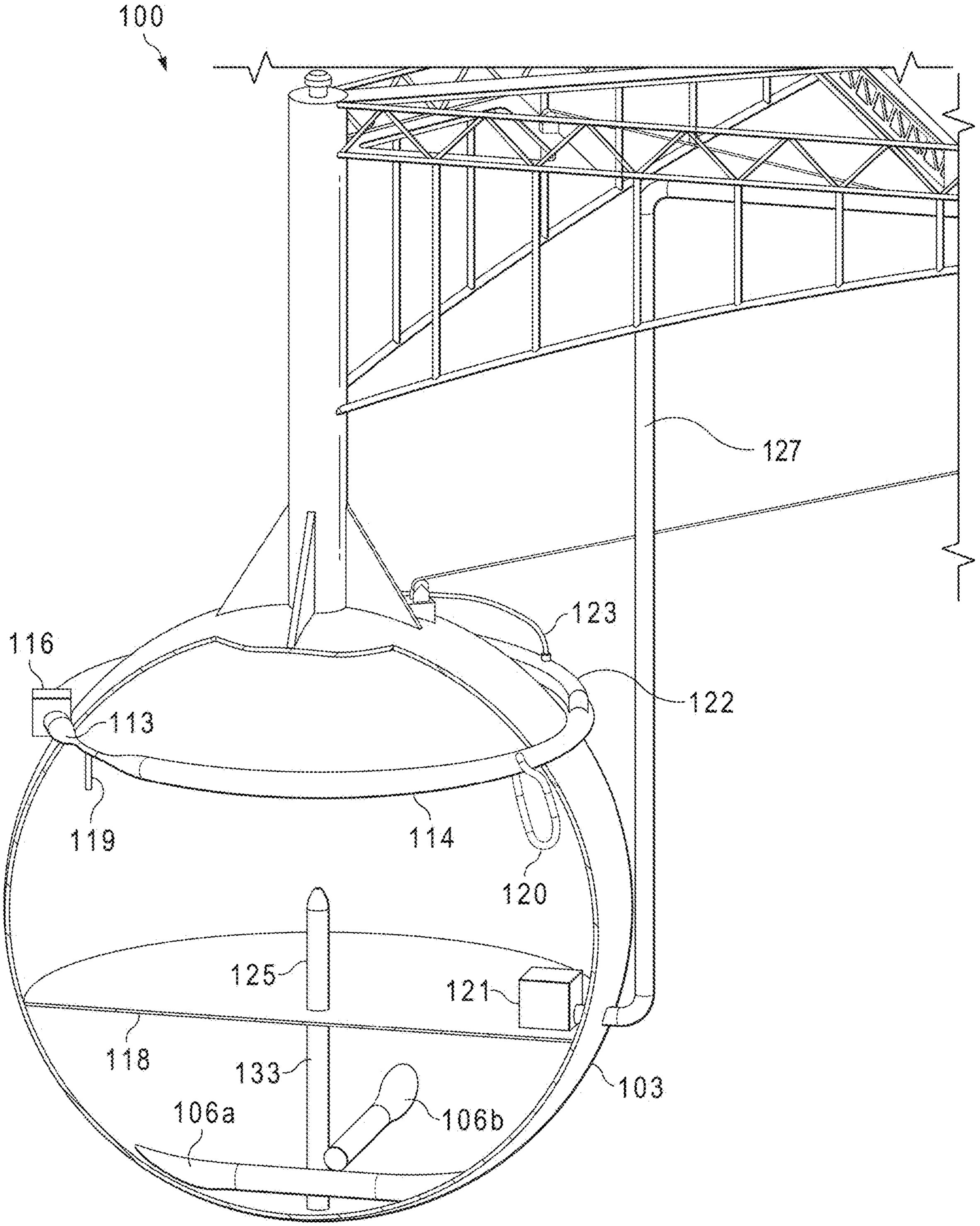
FIG. 10 is a detailed close-up partial perspective view of the first embodiment with some surfaces removed for clarity.

FIG. 10 shows partial perspective side view of the same embodiment of the present disclosure that is illustrated in FIGS. 1-9, with part of the outer first degassing sphere's 103 surfaces depicted as transparent for clarity. First degassing sphere 103 is comprised of a nozzle 125 through which seawater enters the sphere, a pump 121 that moves seawater to a second degassing sphere (not visible) and maintains a partial vacuum within the first degassing sphere.

First degassing sphere 103 includes a rigid floor 118, and an outlet connection 119 to a venturi circuit 114. The first degassing sphere utilizes, incorporates, and/or includes, two directional thrusters, propellers, water jets and/or other propulsive mechanisms, e.g. 106*a-b*, which, when energized by the embodiment's control system and/or human operator, propels the vessel through the body of water on which it floats. The region within the first degassing sphere that is positioned beneath the rigid floor 118 constitutes a permanent buoyancy compartment and can be filled with a gas, a vacuum, and/or a buoyant material, e.g. plastic foam.

Mounted to the embodiment's first degassing sphere 103 is a venturi circuit 114, which is comprised of a looped hollow tube wherein a portion of the tube's internal channel is tapered to a constricted and/or narrowed venturi tube section 113. At one end of the venturi tube section is a pump 116. At a larger diameter portion of the tube's internal channel is a recessed high-point 122 that acts as a separation gallery and/or collection chamber which allows, facilitates, and/or enables, a collection of N2 and O2 bubbles that coalesce within the seawater flowing therethrough. The recessed high point 122 within the tube's internal channel is fluidly connected to an exhaust port 123 through which said N2 and O2 gases are expelled, ejected, and/or vented, into the atmosphere above the embodiment.

The venturi circuit is further comprised of an outlet hose 120 that allows any excess water introduced to the circuit (e.g. as water vapor) to be expelled.

As first degassing sphere 103 floats on an upper surface of a body of water, seawater tends to move up, into, and through nozzle 125, and is thereafter ejected from an upper mouth of the nozzle 125 and therefrom into an interior of the first degassing sphere 103. The partial vacuum drawn inside the first degassing sphere 103 by pump 121 facilitates and/or enables, the flow of seawater from the body of seawater on which the embodiment floats, and into, through, and out from, nozzle 125.

The upper mouth of nozzle 125 is constricted which tends to cause water ejected from the nozzle and injected into the first degassing sphere 103 to spray, which tends to cause the ocean water so ejected to disperse as droplets within an interior of the first degassing sphere. Because first degassing sphere is comprised of a rigid, horizontal floor 118, water injected into, and trapped inside, the first degassing sphere tends to slosh, splash, agitate, and/or move about, in a vigorous manner (more so than if the interior was entirely, truly, and/or completely, spherical), which movements tend to create splashing and spray, which in turn causes ocean water within the first degassing sphere to disperse as droplets.

Seawater is circulated within the venturi circuit 114 by a pump 116, and the low static pressure of said fluid within the venturi throat section 113 of said circuit draws fluid from first degassing sphere 103 through outlet connection 119, thereby reducing a pressure within the first degassing sphere. The resulting suction within the first degassing sphere tends to create a relative vacuum within the first degassing sphere 103, and because of this suction and/or partial vacuum, gases dissolved within the seawater within the first degassing sphere will tend to be released, and/or to evolve, and said evolved gases will tend to move from an interior of the first degassing sphere to and/or into the venturi circuit 114 through outlet connection 119 that connects the narrow, constricted portion of the venturi circuit 114, where static pressure within the fluids flowing through the venturi circuit will tend to be minimal, to the interior of the first degassing sphere 103.

Pump 116 circulates seawater through venturi circuit 114. The venturi circuit is a roughly circular hollow tube of which a portion of an interior channel of the tube is of a larger diameter than an interior channel of the venturi tube 113 section. The venturi circuit 114 tapers down to the venturi throat section 113, which is the narrowest point of the circuit, and/or the narrowest portion of an internal channel of the tube. As seawater circulates within the venturi circuit, the relative speed at which the seawater circulates within the tube's internal channel will tend to be higher where the pump 116 forces this liquid through the venturi tube section 113 of the tube, and will tend to be relatively slower as and after the seawater enters a non-constricted portion of the tube with a larger diameter. This slowing of the fluid within the venturi circuit, following its passage through the venturi portion of the circuit, tends to allow N2 and O2 to coalesce into gas bubbles. As these coalesced bubbles of gases continue to flow through the venturi circuit, N2 and O2 will tend to collect in the recessed, elevated, and/or expanded, portion of the tube's channel, i.e. high point 122. N2 and O2 that collect in this high point are expelled and/or vented into the atmosphere via an exhaust port 123.

The continual suction of N2 and O2 into the venturi circuit 114, and the concomitant expulsion and/or venting of N2 and O2 into the atmosphere, tends to result in a degassing of N2 and O2 of the water within the first degassing sphere 103. An outlet hose 120 located on, and fluidly connected with, the venturi circuit tends to expel any excess water introduced into the venturi circuit, by suction, from the degassing sphere. The venturi circuit 114 is a form of vacuum pump.

Ocean water within degassing sphere one 103 that has been degassed of N2 and O2 is moved to second degassing sphere 104 via a pump 121 and pipe 127 and, prior to introduction into the second degassing sphere 104, is combined with hydrochloric acid solution collected from WECs and stored aboard the vessel 100.

Figure 11:
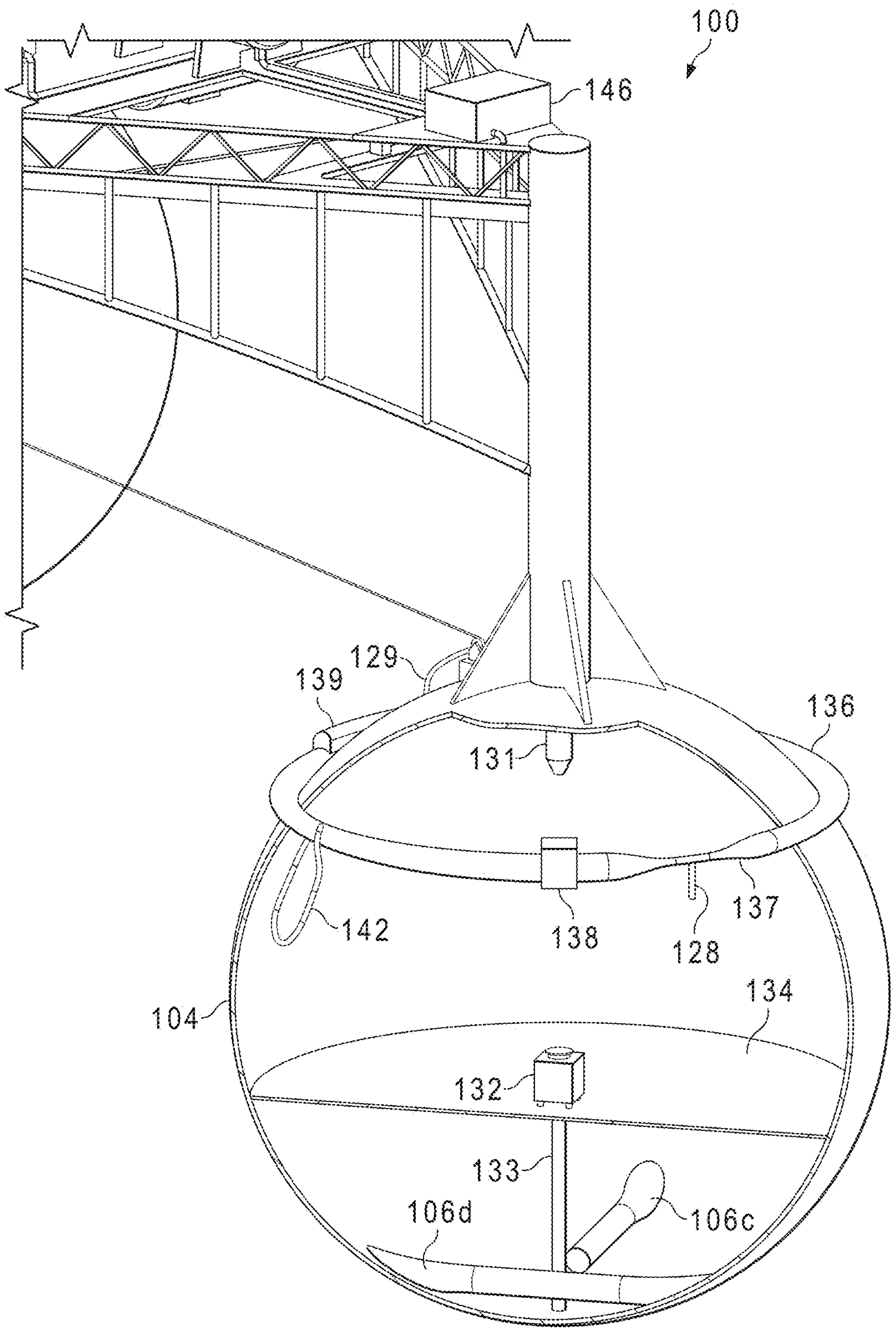
FIG. 11 is a detailed close-up partial perspective view of the first embodiment with some surfaces removed for clarity.

FIG. 11 shows partial perspective side view of the same embodiment of the present disclosure that is illustrated in FIGS. 1-10, with the second degassing sphere's 104 outer surfaces depicted as transparent for clarity.

Second degassing sphere 104 utilizes, incorporates, and/or includes, a nozzle 131 through which seawater degassed in the first degassing sphere (not visible, see 103 in FIG. 10) flows into, and/or enters, an interior of the second degassing sphere. The second degassing sphere also utilizes, incorporates, and/or includes, a pump 132 and a pipe 133 for removing seawater from the sphere and ejecting it into the ocean on which the embodiment floats. The second degassing sphere also utilizes, incorporates, and/or includes, a rigid floor 134, and an outlet connection 128 to a venturi circuit 136. The second degassing sphere 104 is also comprised of water jets, e.g. 106*c-d*, which, when energized, propel the vessel through the body a water on which the embodiment floats. The second degassing sphere incorporates and/or includes a permanent buoyancy compartment beneath a rigid floor 134.

Mounted and/or affixed to second degassing sphere 104 is a venturi circuit 136, which is comprised of a looped tube having a hollow interior channel of which a portion of the tube is tapered and/or constricted to form a relatively narrow venturi tube section 137. At one end of the venturi tube section is a pump 138. Another, larger-diameter portion, of the looped tube has an expanded volume (i.e. high-point 139) that acts as a separation gallery and accommodates a collection and/or consolidation of CO2 bubbles, a transfer hose 129 for routing said CO2 for CH3OH synthesis, and an outlet hose 142 that allows excess water introduced to the venturi circuit 136 to be expelled.

Extraction of dissolved CO2 from water by vacuum is inefficient, if not impossible, if the pH of said water is not first lowered to or below a threshold acidity. CO2's solubility in water is an apparent exception to Henry's Law (whereby the amount of dissolved gas in a liquid is directly proportional to the partial pressure of the gas above the liquid) as CO2 reacts with water to form carbonic acid which ionizes into bicarbonate ions. Bicarbonate ions are not subject to Henry's Law; therefore only a small amount of dissolved inorganic carbon can be released and collected through vacuum methods alone. To effectively degas and thereby release and collect dissolved inorganic carbon from water, the pH of the water must be low enough to alter the equilibrium between the bicarbonate ions and the CO2. At a pH of 8.3 or higher, primarily bicarbonate ions are present in water. At a pH level of approximately 4.5, or lower, most dissolved inorganic carbon in water is present as a dissolved gas (relatively little bicarbonate is present). Therefore, an introduction and/or addition of an HCl solution into water being pumped from the first degassing sphere 103 (not visible), prior to introduction of said water into the second degassing sphere 104, lowers the pH to a degree sufficient to cause dissolved inorganic carbon in that water to exist primarily in the form of dissolved CO2, thereby allowing a relatively significant amount of CO2 to be released when the partial pressure of CO2 gas is reduced by suction within the second degassing sphere.

Ocean water degassed of N2 and O2 is pumped from the first degassing sphere 103 (not visible) and combined with an HCl solution obtained and/or drawn from HCl stored in an intermediary tank 146 which is injected into the second degassing sphere 104 at the top and/or from a mouth of a nozzle 131. The HCl stored in intermediary tank 146 may be retrieved by the vessel 100 from one or more WECs 102 (not shown in FIG. 11). In some instances, the WECs 102 may generate the HCl through a process that includes the conversion of wave energy into electrical energy. The HCl stored in intermediary tank 146 may also be provided to the vessel 100 by a resupply vessel (not shown in FIG. 11) or any other storage facility for HCl. The mouth of nozzle is constricted such that the acidified water injected into the second degassing sphere tends to spray, causing the HCl solution to disperse into an interior of the second degassing sphere as droplets, thus increasing the surface area of said injected HCl solution. Because the second degassing sphere incorporates and/or includes a rigid, horizontal floor 134, the acidified water within the sphere tends to slosh, splash, and/or move about, in a vigorous manner (more so than if the interior was truly and/or completely spherical), which tends to create spray, which in turn causes the acidified water to disperse as droplets with increased surface area.

Liquid, e.g. seawater, is circulated within the venturi circuit 136 by a pump 138 which draws fluid under suction from an interior of the second degassing sphere 104 through outlet connection 128. This suction creates a partial vacuum within the second degassing sphere, and because of this suction and partial vacuum, dissolved gasses within the water inside the second degassing sphere will tend to bubble out of that water, gather in an upper portion of an interior of the second degassing sphere, and then, under suction, enter the venturi circuit through an outlet connection that connects the narrow, constricted portion of the venturi circuit to the interior of the second degassing sphere.

Pump 138 forces fluid (primarily water and CO2 drawn in by suction) through the constricted venturi tube section 137 of the venturi circuit 136. The venturi circuit is a roughly tube with a roughly circular cross-sectional shape, in which a portion of the tube's internal channel is of a larger diameter than is the venturi tube 137 section. The venturi circuit tapers down to the venturi tube section, which is the narrowest point of the circuit's tubular channel. Fluid circulating within the tube will tend to speed up as the pump 138 forces gas through the venturi tube section and will subsequently tend to slow down as the gas enters the portion of the tube with a larger diameter. This slowing down of the fluid tends to allow CO2 to coalesce into larger gas bubbles. As this coalesced gas continues to travel throughout the venturi circuit, CO2 gas will tend to collect within the recessed high point 139 of the venturi circuit. CO2 is collected from the recessed high point 139 in venturi circuit 136 via connection tube 129. An outlet hose 142 located on the venturi circuit tends to expel excess water that collects within the venturi circuit. The venturi circuit 136 is a form of vacuum pump.

Figure 12:
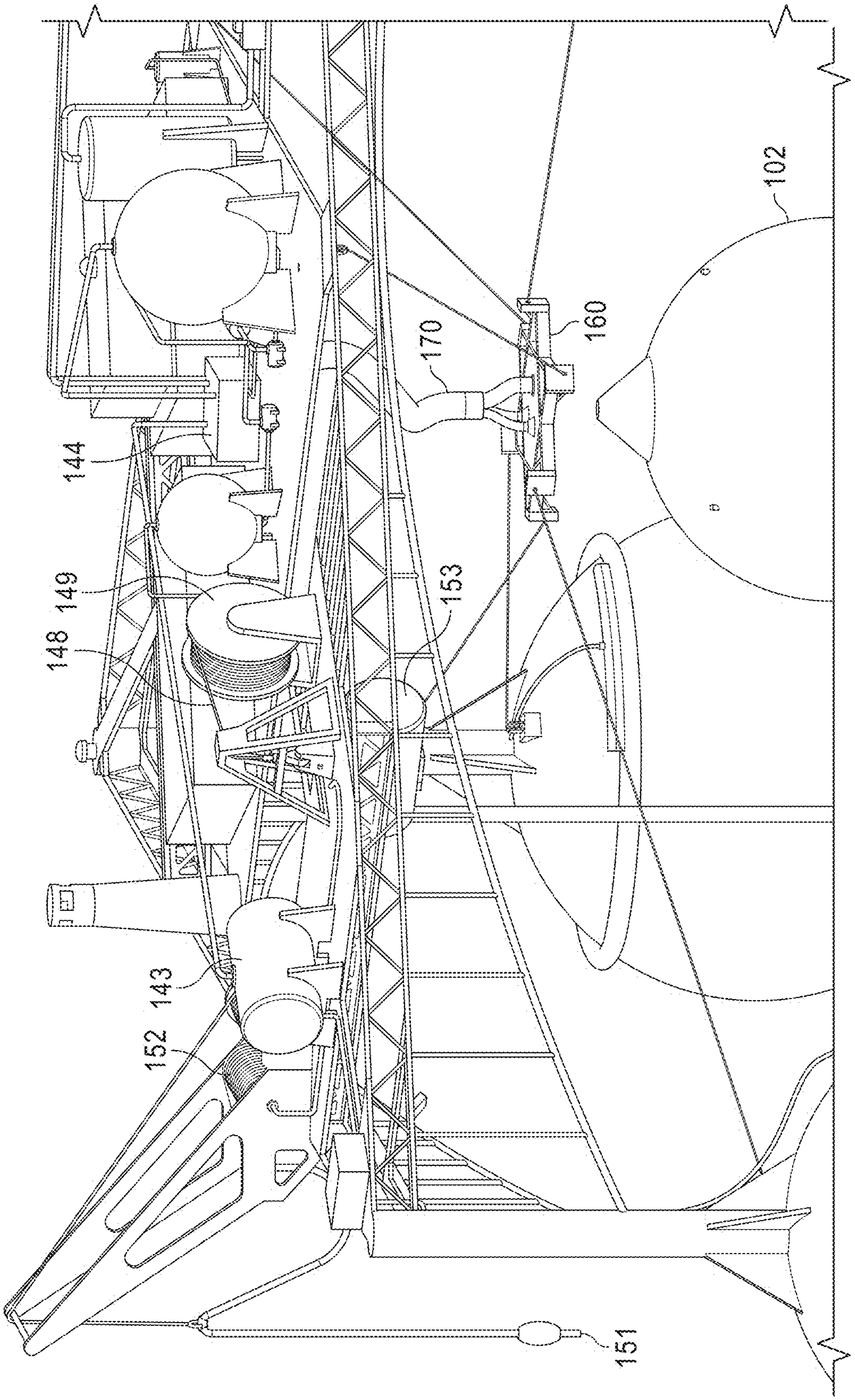
FIG. 12 is a partial close-up perspective view of the first embodiment.

FIG. 12 shows a partial perspective side view of the same embodiment of the present disclosure that is illustrated in FIGS. 1-11. A hydrochloric acid (HCl) solution storage tank 143 collects HCl solution offloaded from a WEC 102 via a pump and valve interchange 144 and composite hose 170 connected to the nozzle head 160. HCl solution may be transferred to an intermediary tank and combined with degassed seawater for CH3OH synthesis. HCl solution may also be transferred directly overboard via a hose 151 and reel apparatus 152 from HCl solution storage tank 143 or transferred and stored in a tank 153 to be sequestered and lowered to the seafloor via a cable 148 and winch 149.

Figure 13:
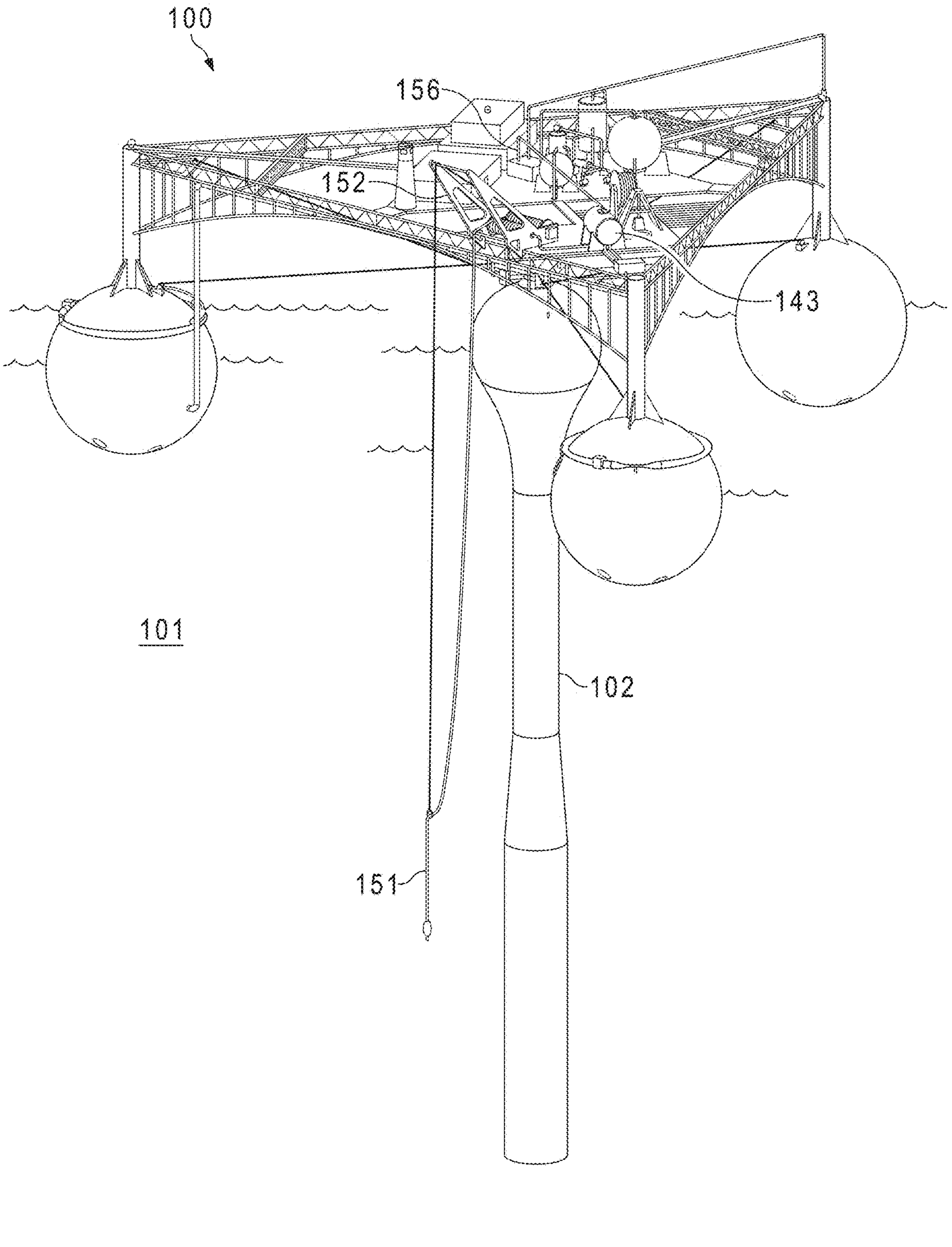
FIG. 13 is a side perspective view of the first embodiment.

FIG. 13 shows a partial perspective side view of the same embodiment of the present disclosure that is illustrated in FIGS. 1-12. Hydrochloric acid (HCl) solution synthesized aboard a WEC 102 is collected via nozzle head 160 and routed to storage tank 143.

In one mode of operation, a reel apparatus 152 deploys a drain hose 151 from the embodiment 100 down into a body of water 101 prior to nozzle head 160 (not visible and shown elsewhere) coupling with the WEC nozzle 112 (not visible and shown elsewhere). The length of the drain hose 151, and therefore the depth at which the offloaded HCl solution flows back into the body of water 101, e.g. 3 kilometers deep, is sufficient for the HCl solution thus deposited to be diluted and neutralized.

In this mode of operation, HCl solution is on boarded via nozzle head 160 (not visible and shown elsewhere) and subsequently sequestered in deep water as part of a single operational process. The embodiment 100 couples with the WEC via the nozzle head. The HCl solution is on boarded and moves directly to the drain hose 151 via a pipe 156 whence it is temporarily collected in storage tank 143 before being drained overboard and into the depths of the body of water 101. Each WEC is drained of its HCl solution at the respective location and/or position of each respective WEC. A portion of HCl solution may be retained to enable the embodiment's degassing-extraction of CO2 from seawater (as explained elsewhere). After draining a WEC of its store of HCl solution, reel apparatus 152 retracts drain hose 151, after which the embodiment is able to travel to the location of another WEC.

In another mode of operation, hose 151 is deployed to depth prior to nozzle head 160 coupling with WEC nozzle 112 and HCl solution is offloaded from the WEC 102 in the same manner described previously, yet once a WEC 102 is drained of its store of HCl, drain hose 151 remains deployed and the embodiment 100 travels to the location of a second WEC (not shown), couples with that second WEC as previously described, and offloads and deposits at depth that WEC's store of HCl solution. In this mode of operation, an embodiment can travel to and drain numerous WECs of HCl solution without retracting drain hose 151.

Figure 14:
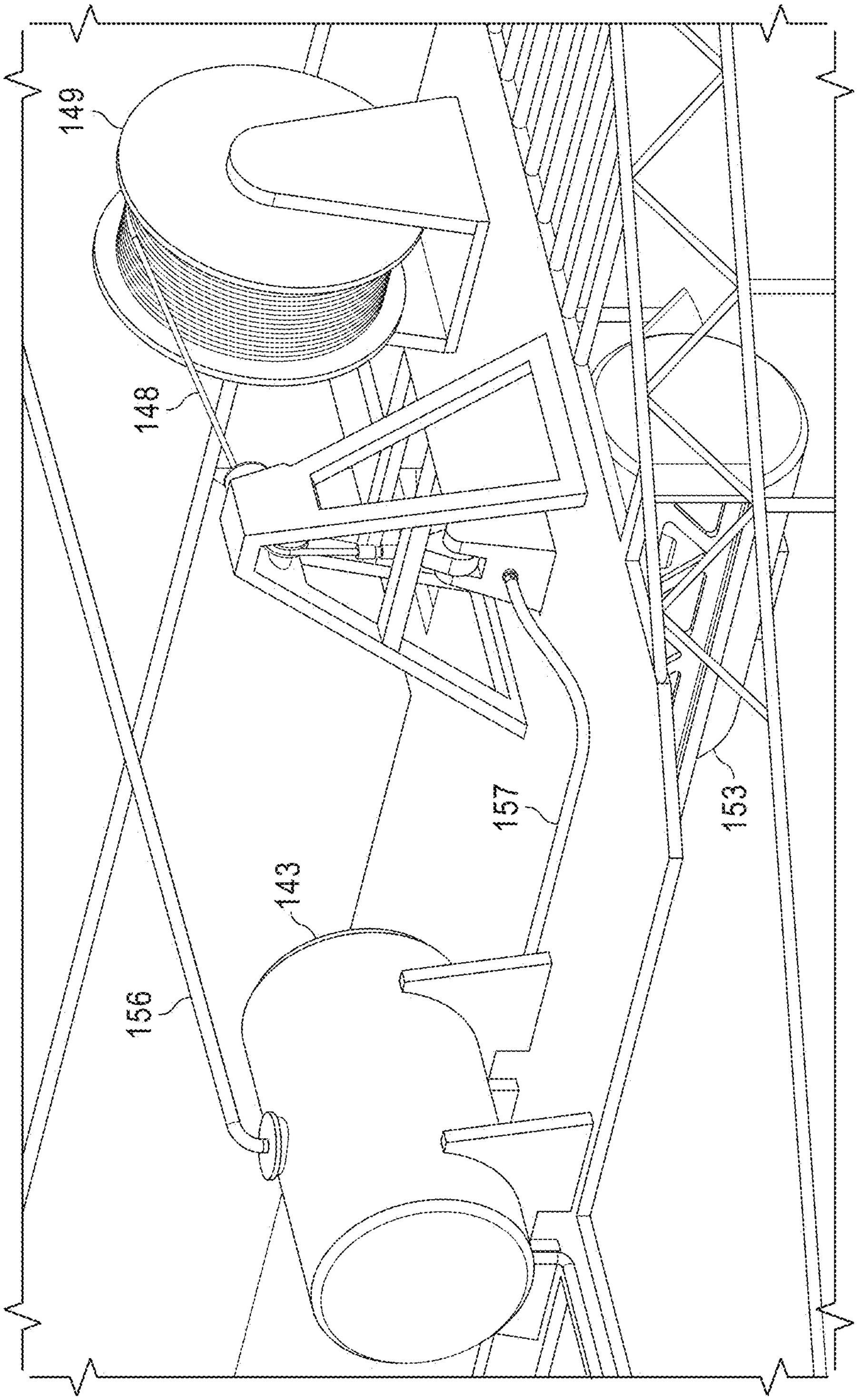
FIG. 14 is a detailed close-up partial perspective view of the first embodiment.

FIG. 14 shows a detailed perspective side view of an upper portion of the same embodiment of the present disclosure that is illustrated in FIGS. 1-13, with the majority of the vessel not shown for clarity.

In this illustrated mode of operation, hydrochloric acid (HCl) solution synthesized aboard a WEC 102 is collected via nozzle head 160 as described and shown elsewhere and routed to an HCl tank 143 via a pipe 156. The HCl solution is then routed to tank 153 via an HCl transfer hose 157. Tank 153 is secured to a length of cable 148 which is wound upon a winch and reel assembly 149.

Figure 15:
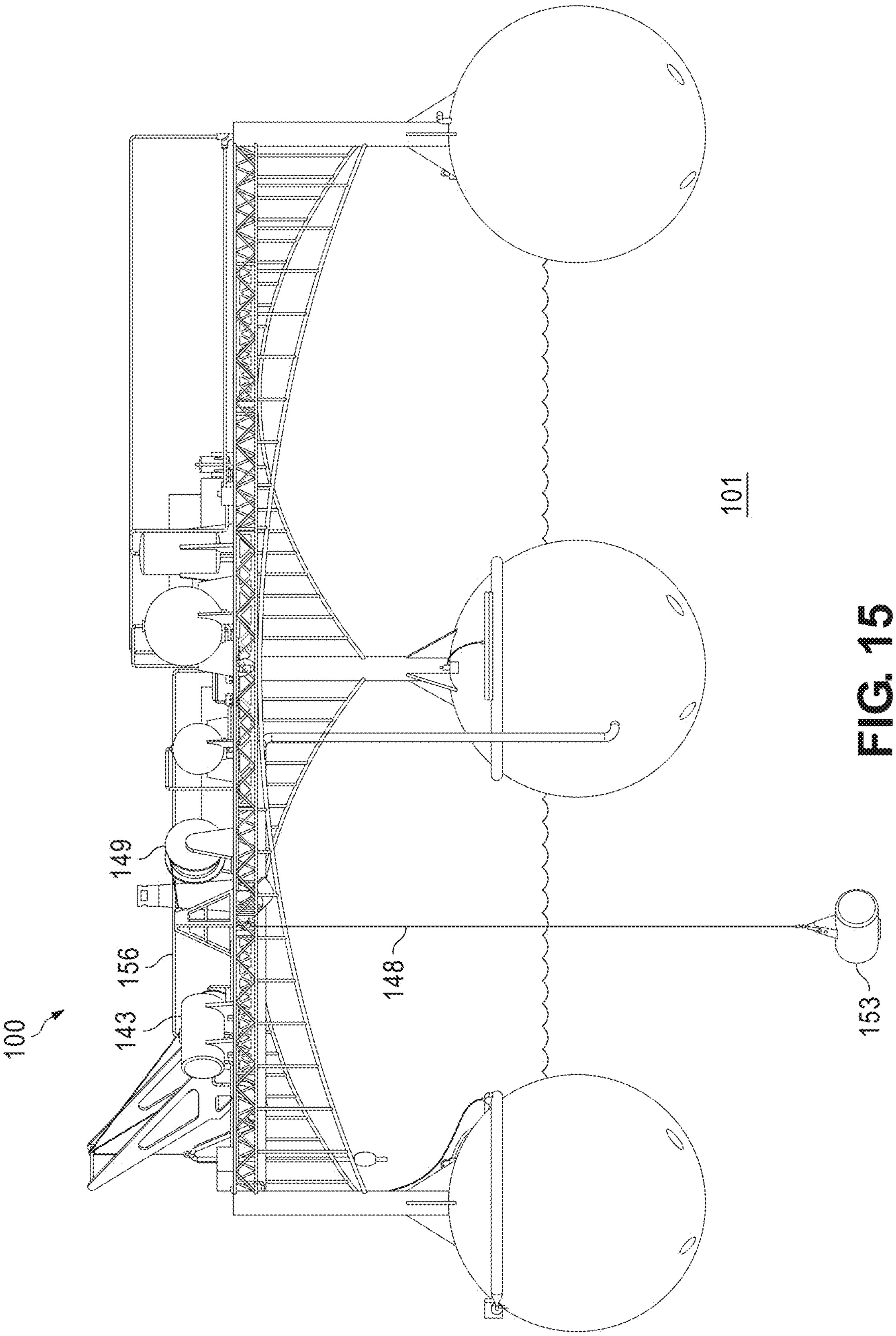
FIG. 15 is a side view of the first embodiment.

FIG. 15 shows side view of the same embodiment of the present disclosure that is illustrated in FIGS. 1-14, with hydrochloric acid (HCl) solution tank 153 being lowered into a body of water 101.

In this mode of operation (the same mode partially described in FIG. 14), HCl solution synthesized aboard a WEC and collected via nozzle head 160 is routed to HCl solution tank 143 via a pipe 156. The HCl solution is then routed to tank 153 via an HCl transfer hose 157 (not visible and shown elsewhere), which is secured to a length of cable 148 which is wound upon a winch and reel assembly 149.

Embodiment 100 may collect HCl solution from multiple WECs until the HCl solution tank 153 is full and/or at capacity. Once full, the HCl solution tank 153 is lowered to an appropriate depth, e.g. 3 kilometers, using the winch and reel assembly 149 and the corresponding length of cable 148. Once the tank 153 is at the appropriate depth, a hatch 154 (not visible and shown elsewhere) operated by a pressure switch opens. The HCl solution is more dense and/or heavier than the surrounding water, therefore once hatch 154 is open, said HCl solution drains out, and/or is expelled, into the body of water 101.

The depth at which the HCl solution flows back into the body of water 101 is sufficient that the HCl solution will be diluted and neutralized there and will result in a net alkalization of the surface waters from which it was extracted. When HCl solution tank 153 is drained of its HCl, the winch and reel assembly 149 retract cable 148, thereby returning the HCl solution tank 153 to the embodiment 100. The embodiment may travel to, couple with, and continue the collection of HCl solution from additional WECs and sequester that additional HCl solution into the ocean via tank 153 in the manner previously described.

In some embodiments, the HCl solution tank 153 is provided with weights, floats, and/or otherwise buoyancy calibrated so that the HCl solution tank is negatively buoyant when it contains HCl solution, and, by contrast, is net buoyant when it contains only seawater-thereby minimizing the energy required to lower it to depth and pull it back to the surface of the body of water.

Figure 16:
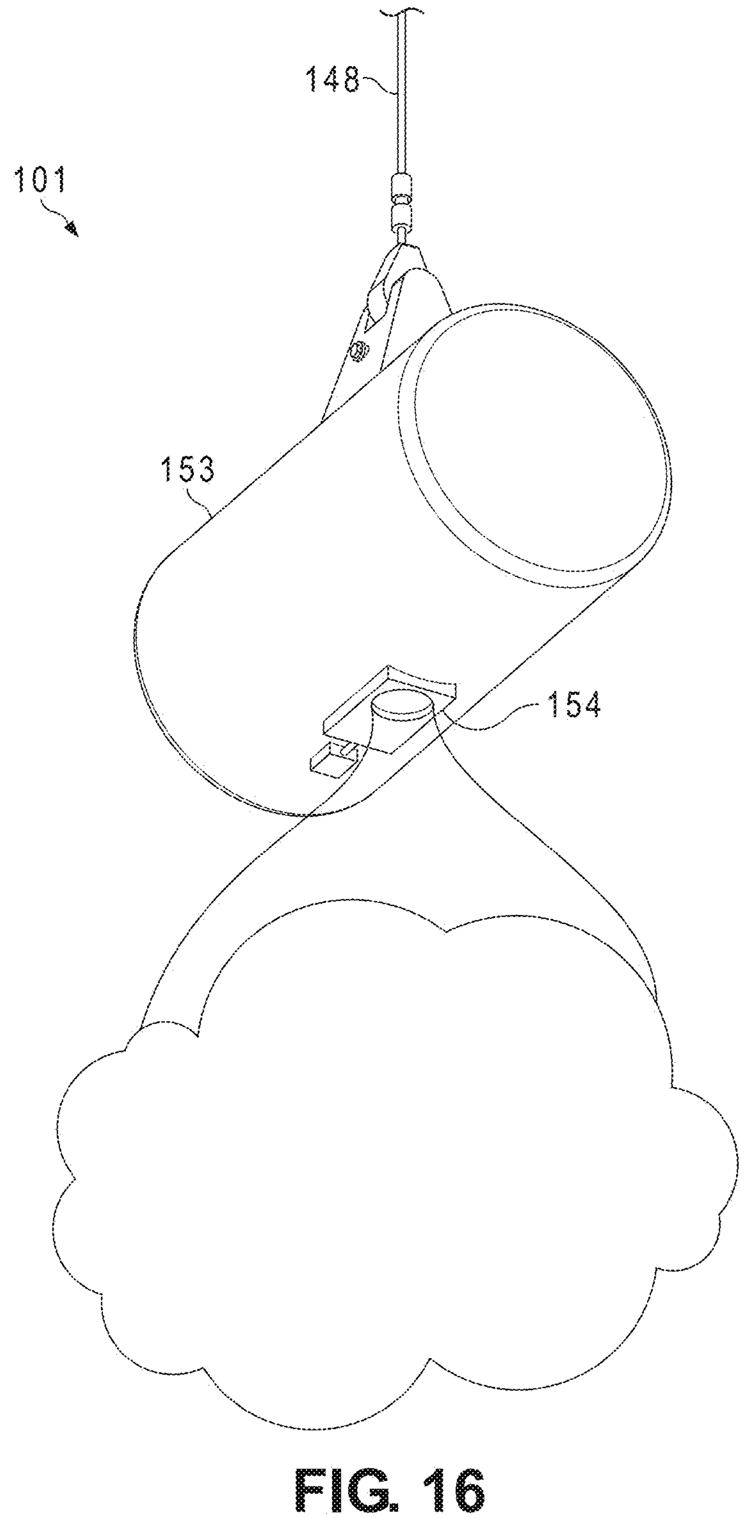
FIG. 16 is a detailed close-up partial perspective view of the first embodiment.

FIG. 16 shows a partial perspective bottom-up view of tank 153 deployed in a body of water 101. Tank 153 has been lowered by a reel assembly 149 (not visible and shown elsewhere) and cable 148 to an appropriate depth, e.g. 3 km, where hatch 154 opens by a pressure switch, thereby releasing and sequestering acidity collected from the surface waters.

Figure 17:
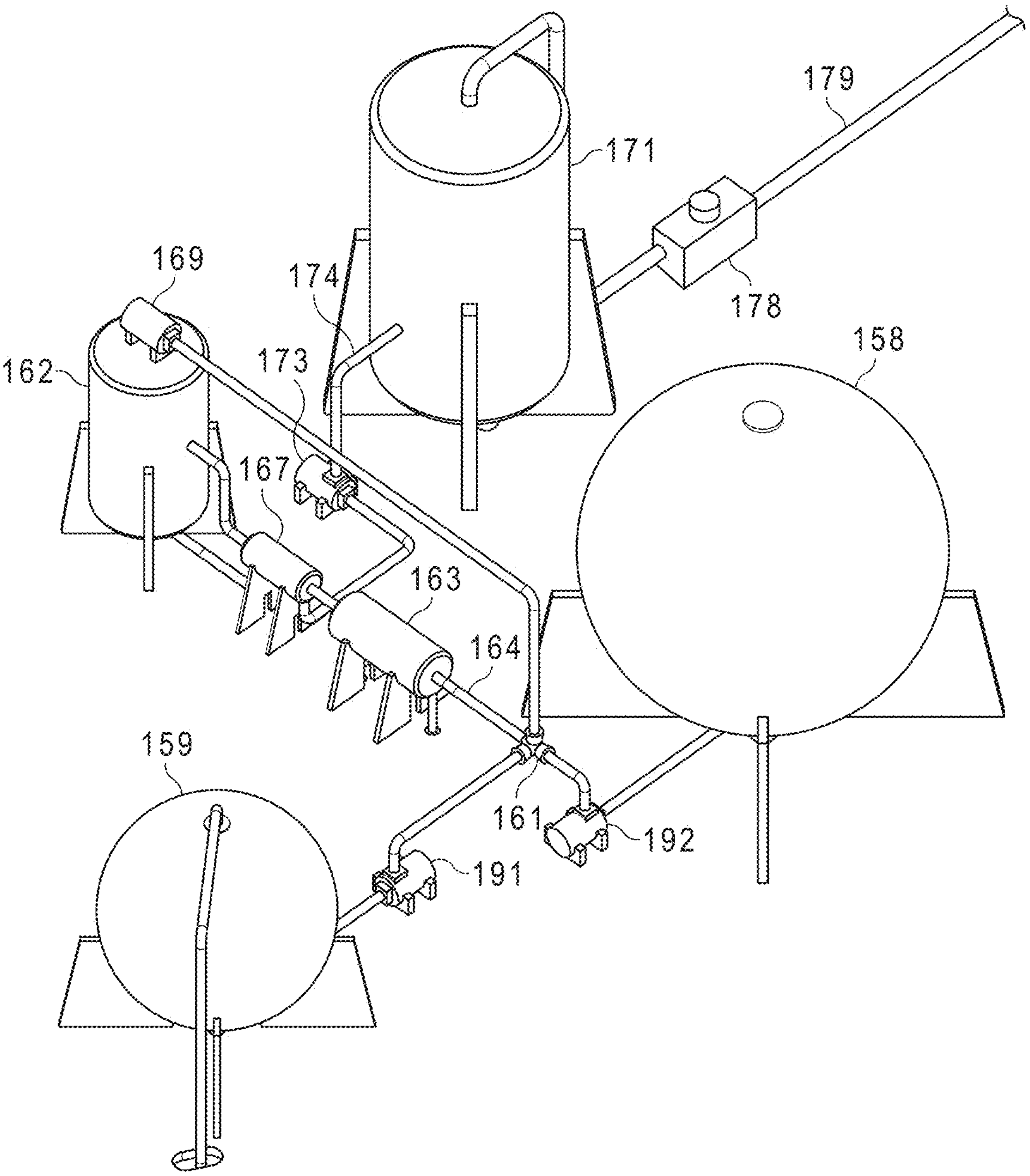
FIG. 17 is a detailed close-up partial perspective view of the first embodiment.

FIG. 17 shows a partial perspective top-down view of the CH3OH processing infrastructure that comprises an upper deck area of the embodiment.

With respect to the embodiment of the present disclosure illustrated in FIGS. 1-16, green methanol (CH3OH) is formed, synthesized, and/or created, through a chemical process of CO2 hydrogenation.

Hydrogen gas (H2) collected from one or more WECs 102 (not visible and shown elsewhere) and stored in H2 tank 158, and CO2 extracted from seawater aboard the embodiment and stored in CO2 tank 159, are transferred by CO2 pump 191 and H2 pump 192 into mixer 161 wherein they mix together. Also transferred into mixer 161 is a recirculated stream from flash vessel 162 which tends to heat the initial stream of H2 and CO2 gases. The heated and mixed H2 and CO2 gases are then transferred to and/or into catalytic reactor vessel 163 via pipe 164.

Inside the catalytic reactor vessel 163, the H2 and CO2 gas mixture is heated to approximately 150° C. by a heat exchanger within the reactor vessel in which an exothermic reaction takes place in the presence of appropriate catalysts. The temperature within the catalytic reactor vessel 163 can reach 250° C. and the pressure within the catalytic reactor vessel can reach 65 bar or higher. A gas product resulting from the reaction is pumped to heat exchanger 167 and then to flash vessel 162, where the temperature and pressure can be 30.0° C. and 64.5 bar, respectively. The top outlet stream of flash vessel 162 is reintroduced to reactor vessel 163 via a pump 169 and pipe 172 at the mixer 161. Purge gas is released to expunge byproducts such as hydrocarbons, inert gases, etc., via an outlet valve (not shown) prior to that stream's reintroduction into the mixer 161 and reactor vessel 163.

A crude liquid stream of CH3OH (also containing water and other undissolved gasses) from a bottom-most portion of flash vessel 162 is reheated (e.g., to 85° C.) by heat exchanger 167 and transferred to distillation tower 171 through a pipe 174 and a compressor pump 173 at an inlet pressure that is approximately 1.3 bar. Distillation tower 171 completes the CH3OH synthesis by separating CH3OH from water. Gaseous CH3OH is transferred to methanol ballast sphere 105 (not visible and shown elsewhere) by compressor pump 178 and pipe 179, where the CH3OH is cooled to form a liquid. Water separated from the aqueous solution of CH3OH within and/or by the distillation tower is expelled from the bottom of the distillation tower.

Alternate embodiments of the present disclosure may use additional heat exchangers, flash vessels, pumps, compressors, and other components and may operate at different temperatures and pressures as will be apparent to one skilled in the art. Given streams of CO2 and H2, multiple related methods exist in the prior art for methanol synthesis, and all such alternate methods, and alternate mechanisms for executing them, are included within the scope of the present disclosure.

Figure 18:
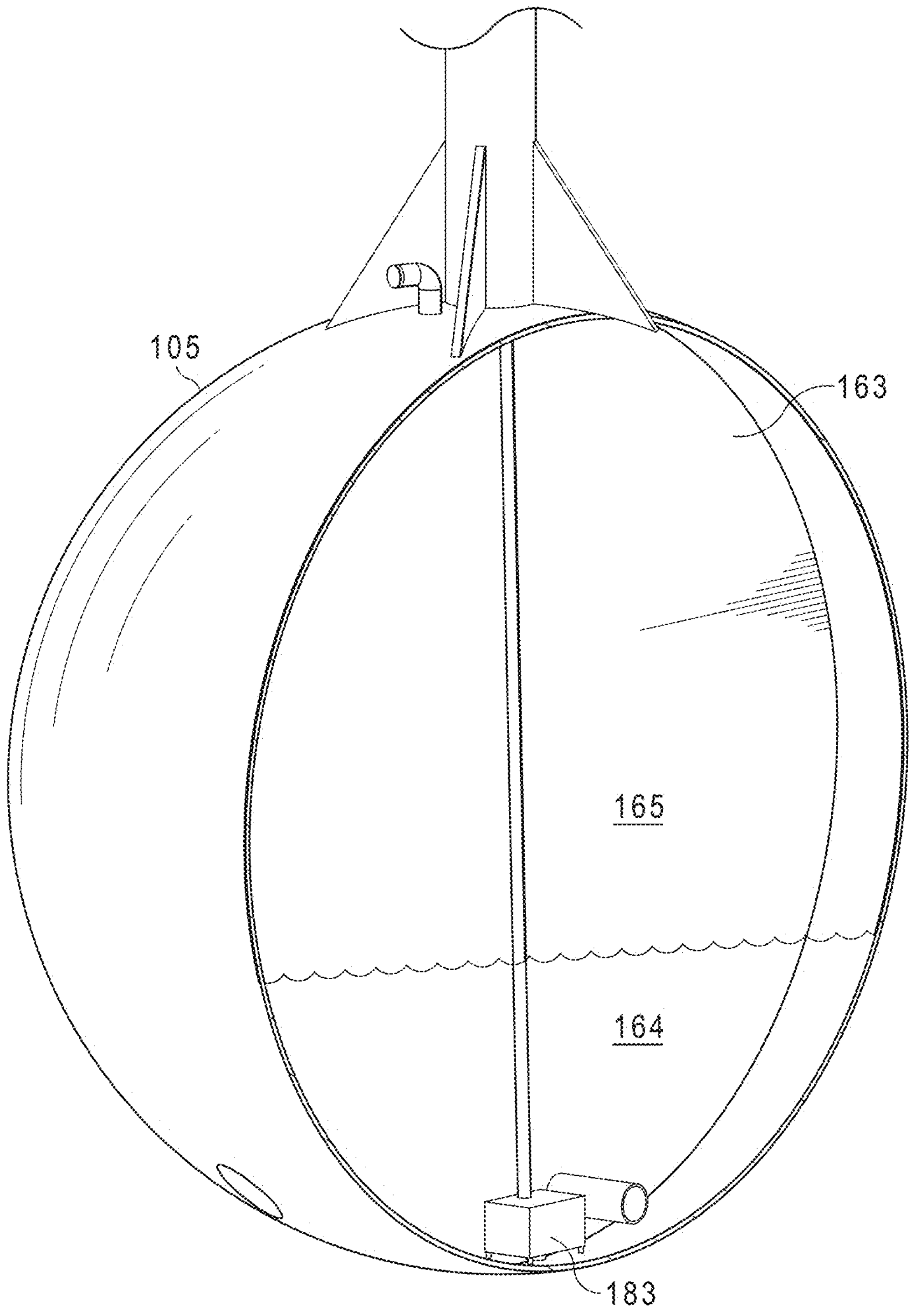
FIG. 18 is a detailed close-up partial perspective view of the first embodiment with some surfaces removed for clarity.

FIG. 18 shows a partial perspective side view of methanol ballast sphere 105 with some surfaces removed for clarity. A quantity of synthesized CH3OH 162 (not visible and shown elsewhere) is stored within the methanol ballast sphere which additionally acts and/or serves as a floatation implement for the disclosed embodiment. The methanol ballast sphere is of the same or similar size as the previously disclosed first 103 and second 104 degassing spheres and is separated internally into two chambers by an approximately vertical bulkhead 163, one chamber being for the storage of CH3OH synthesized and purified aboard the embodiment, and the other chamber containing a supply of water 164 and air 165 with an alteration of the relative amounts of each allowing a buoyancy of the sphere to be maintained even as the volume of CH3OH stored in the adjacent chamber is steadily increased, and maintaining a buoyancy of that methanol ballast sphere which is approximately equal to the buoyancies of the embodiment's first and second degassing spheres.

A ballast pump 183 maintains an appropriate ratio of air and water in the methanol ballast sphere so as to maintain proper buoyancy in that sphere, depending on the quantity of methanol stored in the methanol chamber.

Figure 19:
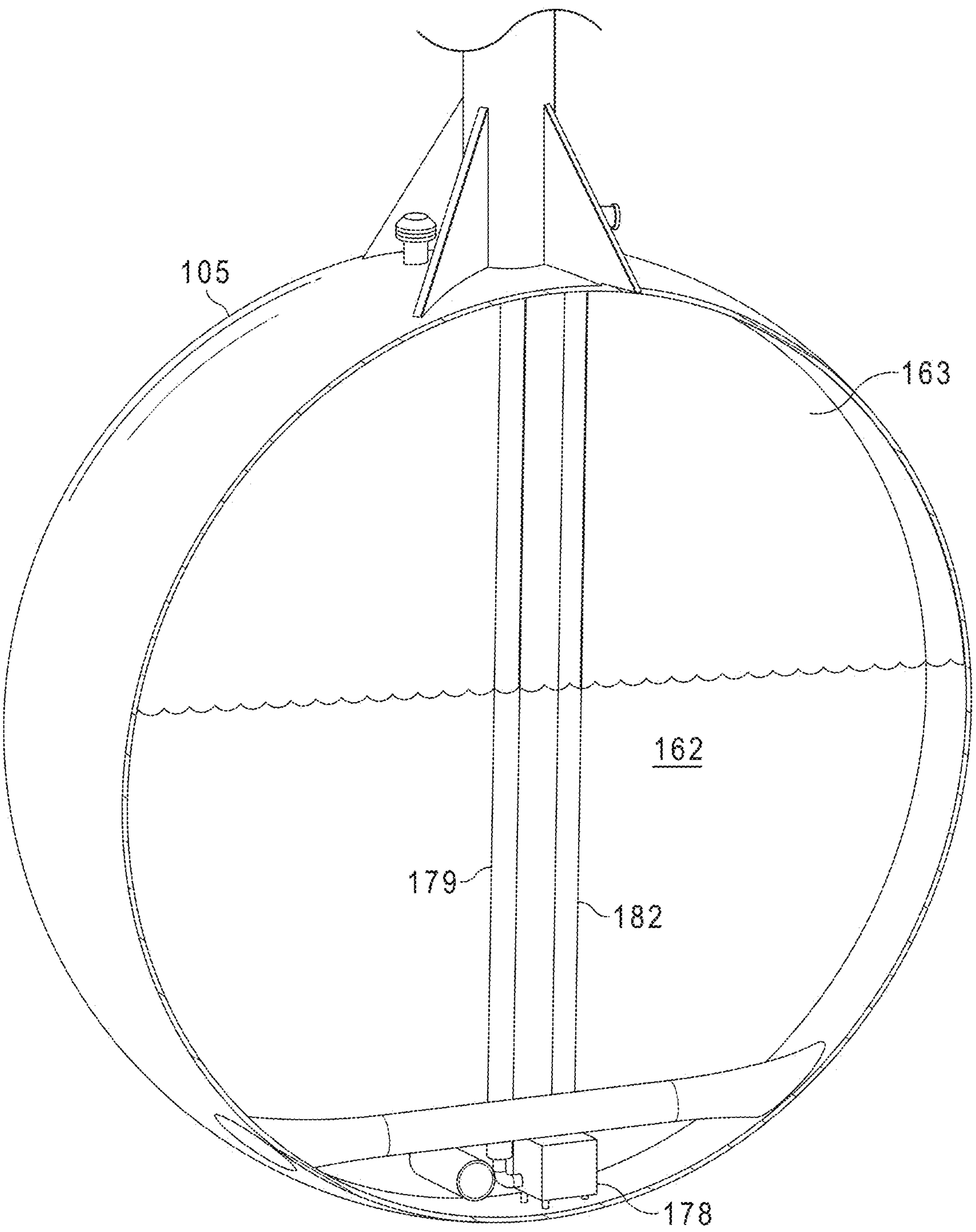
FIG. 19 is a detailed close-up partial perspective view of the first embodiment with some surfaces removed for clarity.

FIG. 19 shows a partial perspective side view of methanol ballast sphere 105 with some surfaces removed for clarity. The sphere is separated internally into two separate laterally adjacent chambers by an approximately vertical bulkhead 163, the chamber visible in FIG. 19 being the chamber used for storage of CH3OH 162. A pump 178 and pipe 179 move CH3OH 162 into the methanol ballast sphere 105 after it is synthesized, and pump 178 and a pipe 182 transfers CH3OH 162 to another vessel or land-based storage facility, e.g. via an engaged end effector.

Figure 20:
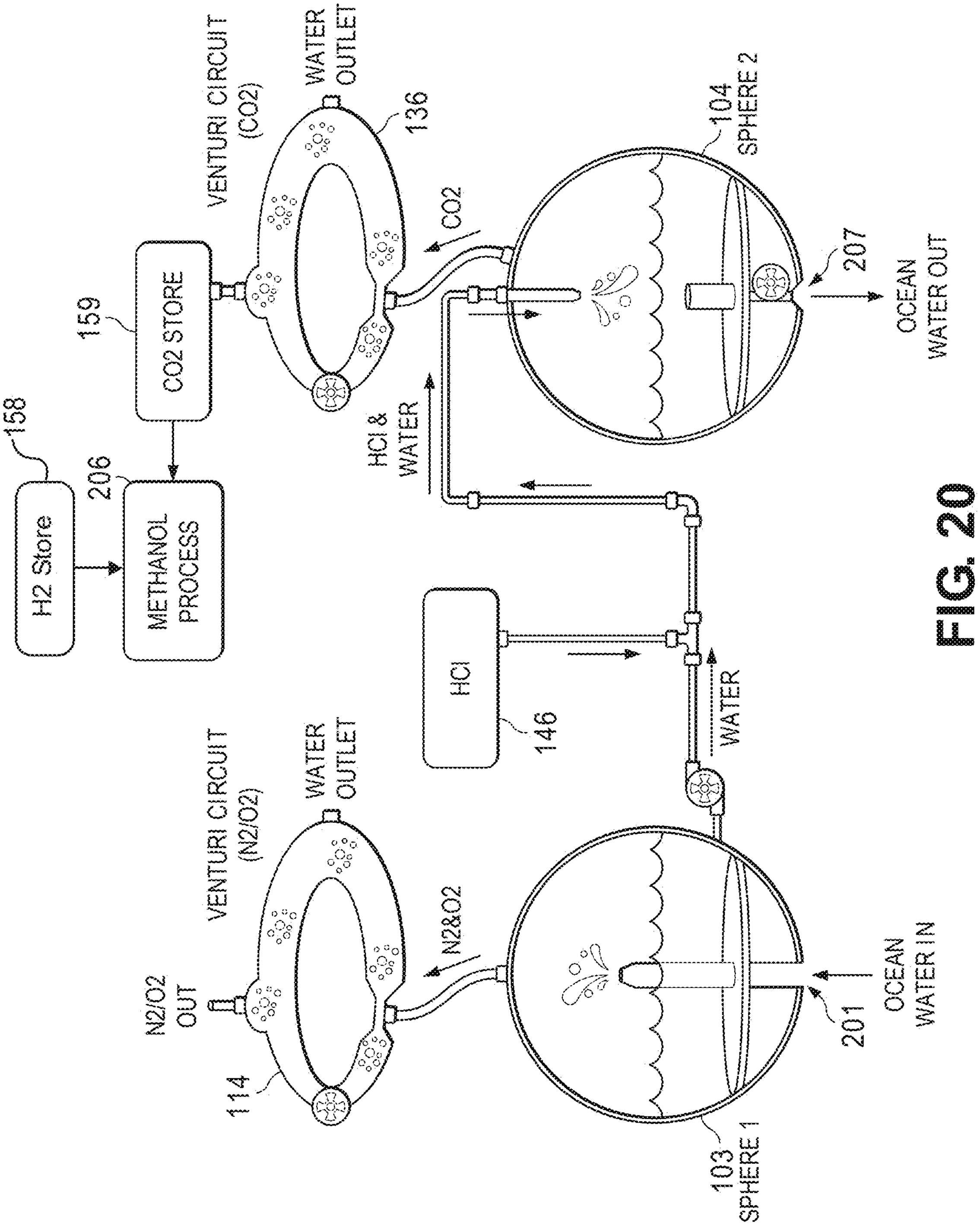
FIG. 20 is an infographic.

FIG. 20 shows a diagram detailing a process by which seawater is degassed of N2, O2 and carbon dioxide (CO2) via first 103 and second 104 degassing spheres, venturi circuits, pumps, plumbing, piping and valves as described previously. Ocean water 201 enters the first degassing sphere wherein dissolved N2 and O2 gases are removed via a venturi circuit 114. Degassed water is combined with hydrochloric acid (HCl) solution from intermediary tank 146 as it is pumped to second degassing sphere where it dissolved CO2 gas is removed via a venturi circuit 136. Said CO2 gas is collected in CO2 tank 159 and subsequently used for methanol (CH3OH) synthesis 206. The methanol synthesis 206 may also be provided H2 gas from an H2 store 158. The H2 store 158 may be a chamber on the vessel, or the H2 store 158 may be a WEC that is fluidly coupled to the vessel during the methanol synthesis 206 process. Degassed seawater is reintroduced into the ocean 207.

Figure 21:
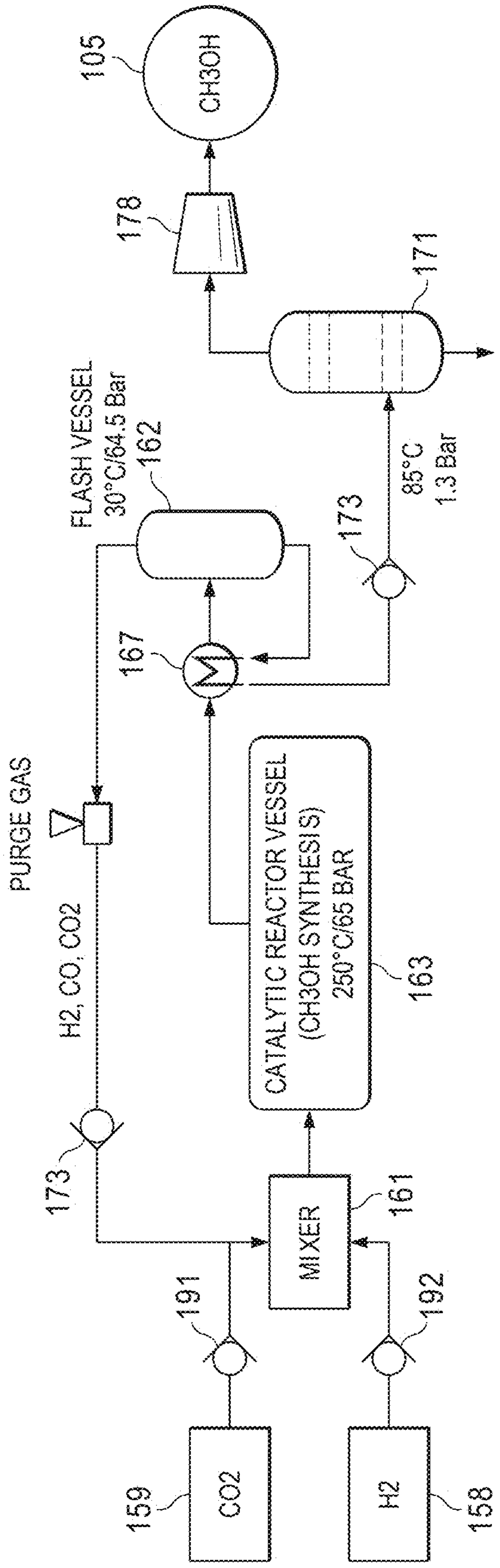
FIG. 21 is an infographic.

FIG. 21 shows a diagram detailing the process by which CH3OH is synthesized from, by, and/or through, CO2 hydrogenation. CO2 stored in CO2 tank 159 and H2 stored in H2 tank 158 are pumped with pump 191 and pump 192 and combined in a mixer 161 with a recirculated stream from flash vessel 162. The mixed stream (of CO2 and H2 gases) is pumped to a catalytic reactor vessel 163 where an exothermic reaction takes place, and the temperature and pressure can reach 250° C. and 65 bar, respectively, or higher. The post-reaction stream exits the catalytic reactor vessel 163 and passes through heat exchanger 167 and then enters flash vessel 162 where the temperature and pressure will be approximately 30.0° C. and 64.5 bar, respectively.

A stream of H2, CO and CO2 from flash vessel 162 is recirculated back to mixer 161 by pump 169 after being purged of a small amount of gas to further purify the stream. The liquid stream from flash vessel 162 enters heat exchanger 167 which is then pumped to distillation tower 171 by pump 173. The crude CH3OH stream entering distillation tower 171 can be at a temperature and pressure of 85° C. and 1.3 bar, respectively. A final separation of CH3OH and water takes place within distillation tower 171. Gaseous CH3OH is pumped to methanol ballast sphere 105 via a compressor pump 178 where the CH3OH is cooled to liquefaction. Water extracted from the crude aqueous CH3OH is released from a bottom of the distillation tower 171. Other processes for synthesizing methanol from CO2 and H2 are known in the prior art and can be used in place of the one shown. Embodiments utilizing, incorporating, and/or including, such other methanol synthesis processes and/or associated mechanism and equipment are included within the scope of the present disclosure.

Figure 22:
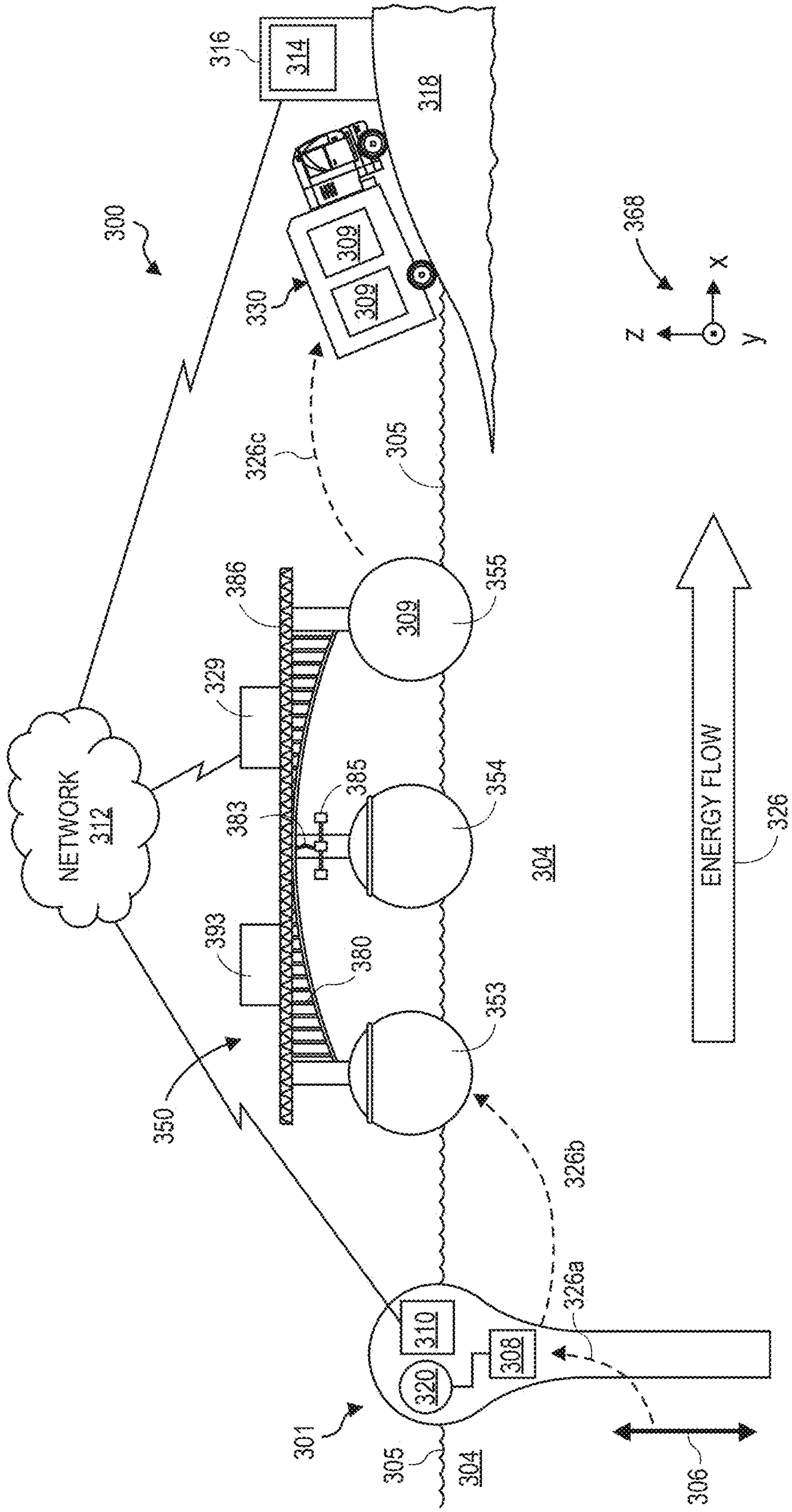
FIG. 22 is a side view of an energy flow diagram of energy products starting at a WEC, delivered to a vessel, and transported to shore.

FIG. 22 a schematic diagram of a wave energy harvesting system 300 is shown. The wave energy harvesting system 300 may include a first free-floating body 301 and a second free-floating body 350 which may transiently couple to one another while floating on a surface 305 of a body of water 304. In an example embodiment, the first free-floating body 301 may be configured as a wave engine 301 (e.g., a WEC or hydrodynamic pump, such as those described herein) and the second free-floating body 350 may be a reaction and storage vessel 350, such as a vessel 100 described in greater detail herein. For example, the storage vessel 350 may comprise a first degassing chamber 353, a second degassing chamber 354, and a methanol ballast chamber 355. The chambers 353-355 may be fluidly connected to each other, as described herein. The chambers 353-355 may be mechanically coupled to each other by a structure 386 (e.g., a deck or platform) that is supported by reinforcing members 380, or the like. The chambers 353-355 may be positioned at vertices of a triangle in order to provide a stable base to support the structure 386 on the surface 305 of the body of water 304.

In some embodiments, the wave engine 301 may include a receiving port 320 operable to receive a nozzle 385 in fluidic communication with a conduit 383 from the vessel 350 and thereby fluidly couple the wave engine 301 to the vessel 350 via the conduit 383 for transfer of one or more fluids therebetween.

In an embodiment, the fluidic communication (or fluidic coupling) between the wave engine 301 and the vessel 350 may be enabled through the use of automated, autonomous, and/or passive systems. In some embodiments, for instance, the nozzle 385 may be coupled to an end effector (not shown in FIG. 22, but described elsewhere herein) that is able to be moved with wires and pulleys that enable six degrees of freedom so as to facilitate, enable, and/or realize, a coupling, and/or a fluid-connection of the nozzle 385 to the WEC 301 receiving port 320. Further, since both the WEC 301 and the vessel 350 are floating on the same surface 305 of the body of water 304, the relative motion between the WEC 301 and the vessel 350 is minimal, which facilitates simpler coupling. That is, the WEC 301 and the vessel 350 may float in a manner similar to each other since both the WEC 301 and the vessel 350 experience substantially the same wave patterns, currents, wind, and/or other environmental conditions.

A set of Cartesian coordinate axes 368 is shown in FIG. 22 for contextualizing positions of the various components of the wave energy harvesting system 300. Specifically, x-, y-, and z-axes are provided which are mutually perpendicular to one another, where the x- and z-axes define a plane of the schematic diagram shown in FIG. 22 and the y-axis is perpendicular thereto. In some embodiments, a direction of gravity may be parallel to and coincident with a negative direction of the z-axis.

Though exemplified herein in the context of wave engines, the first free-floating body 301 may be configured as any free-floating body capable of self-propulsion, e.g., by extracting energy from stored fuel, inducing a flow of pressurized water, and/or harnessing one or more ambient environmental forces, so as to translate along the surface 305 of the body of water 304. For example, the first free-floating body 301 may be a ship (such as a deployment ship, a tanker ship or other storage vessel, or another transport vessel), a buoy, a wind turbine, an offshore platform, such as a floating data center, or the like.

In embodiments where the first free-floating body 301 is configured as the wave engine 301, water may pass into and through the wave engine 301 with upward and downward motion 306 (e.g., in a positive direction of the z-axis and the negative direction of the z-axis, respectively) of water waves. As described in greater detail herein, the upward and downward motion 306 may induce the water passing into and through the wave engine 301, energy from which may be captured and converted to an energy product 308 (as indicated by a dashed arrow **326*a*). The energy product 308**, for example, may include one or more of an electrolysis product or other fuel/chemical, such as H2 gas, HCl, etc., removed carbon, minerals, a biological product, digital goods, or an executed computational algorithm, such as, but not limited to a proof-of-work mechanism for a cryptocurrency, a trained machine learning algorithm, or the like.

In some embodiments, the first free-floating body 301 may include a first onboard controller or other computing device 310 and/or the second free-floating body 350 may include a second onboard controller or other computing device 329, the first and second onboard controllers 310, 329 each including non-transitory memory on which executable instructions may be stored. The executable instructions may be executed by one or more processors of the first and second onboard controllers 310, 329 to respectively perform various functionalities of the first and second free-floating bodies 301, 350. Accordingly, the executable instructions may include various routines for operation, propulsion, maintenance, tracking, and testing of the first and second free-floating bodies 301, 350. The first and second onboard controllers 310, 329 may be communicably coupled to various components (e.g., valves, power supplies, etc.) of the first and second free-floating bodies 301, 350 to command actuation and use thereof (wired and/or wireless communication paths between the first and second onboard controllers 310, 329 and the various components are omitted from FIG. 22 for clarity). For instance, the first onboard controller 310 may command actuation of one or more first coupling elements annularly distributed on the receiving port 320 and the second onboard controller 329 may command actuation of one or more second coupling distributed on the nozzle 385 so as to selectively engage and disengage the one or more first coupling elements with one or more second coupling elements (first and second coupling elements not shown at FIG. 22).

In certain embodiments, the first and second onboard controllers 310, 329 may be communicably coupled to a remote controller or computing device 314 via a wireless network 312. The various controllers 310, 314, 329 may be configured in a substantially similar manner to one another, excepting, in some examples, one or more modifications or differences for a given use case. For example, the remote controller 314 may be positioned so as to be accessible to an operator of the wave energy harvesting system 300, e.g., on a ship or in a physical structure 316 on land 318 (as illustrated in FIG. 22). As such, even when one or both of the first and second free-floating bodies 301, 350 are not geographically located within a national or subnational jurisdiction, the one or both of the first and second free-floating bodies 301, 350 may nevertheless be in continuous (e.g., substantially uninterrupted) or periodic communication with the remote controller 314 which may be geographically located within a national or subnational jurisdiction (e.g., on the land 318).

In some embodiments, because the remote controller 314 may be configured for use by the operator, the remote controller 314 may include a user interface at which the operator may enter commands or otherwise modify operation of the wave energy harvesting system 300. The user interface may include various components for facilitating operator use of the wave energy harvesting system 300 and for receiving operator inputs (e.g., requests to direct the nozzle 385 to the receiving port 320), such as one or more displays, input devices (e.g., keyboards, touchscreens, computer mice, depressible buttons, mechanical switches, other mechanical actuators, etc.), lights, etc. In additional or alternative embodiments, one or both of the first and second onboard controllers 310, 329 may be configured with the user interface as described hereinabove.

An overall energy flow 326 of the wave energy harvesting system 300 is schematically depicted in FIG. 22, in which energy captured at the first free-floating body 301 from water induced therethrough by the upward and downward motion 306 of the water waves (as indicated by the dashed arrow **326*a*) may be converted to the energy product 308 and transferred to the second free-floating body 350 (as indicated by a dashed arrow 326*b*) and then transferred from the second free-floating body 350 to a land-based vehicle 330 (as indicated by a dashed arrow 326*c*) to be transported to a storage facility and/or an end user for consumption. For example, in some embodiments, the wave energy harvesting system 300 may include a plurality of nodes including a plurality of first free-floating bodies 301, one or more second free-floating bodies 350 to transport a plurality of energy products 308 from the plurality of first free-floating bodies 301 to the land 318, and one or more land-based vehicles 330 to transport the plurality of energy products 308 from the one or more second free-floating bodies 350 to the storage facility and/or the end user. In other instances, the energy products 308 may be directly transported from the second free-floating body 350 to a storage facility and/or end user on the land 318 or within a certain distance of the land 318** (e.g., up to 100 kilometers from land, up to 40 kilometers from land, up to 1 kilometer from land, up to 500 meters from land, or up to 50 meters from land). Though storage facilities or consumption locations may be further from land in other embodiments.

In an example embodiment, the energy product 308 may be a fluid (e.g., a liquid or a gas) which is transferred from the first free-floating body 301 to the second free-floating body 350 via the nozzle 385 and the conduit 383, the conduit 383 being configured to transiently fluidly couple an internal reservoir of the second free-floating body 350 to an internal reservoir of the first free-floating body 301 via one or more internal passages extending at least a length of the conduit 383 (internal reservoirs and internal passage(s) not shown at FIG. 22). In certain embodiments, the conduit 383 may include a plurality of internal passages, each of which may convey a different fluid between the first and second free-floating bodies 301, 350. As an example, the conduit 383 may include a first internal passage configured to supply an energy product precursor (e.g., an electrolysis reactant, such as deionized water) from the second free-floating body 350 to the first free-floating body 301 so as to replace the energy product 308 being transferred to the second free-floating body 350. Accordingly, in such an example, the conduit 383 may further include a second internal passage configured to siphon the energy product 308 (e.g., an electrolysis product, such as hydrogen gas) from the first free-floating body 301 to the second free-floating body 350. As such, the overall energy flow 326 may be maintained by periodically (e.g., once per week) replenishing a capacity of the first free-floating body 301 to convert captured energy into a chemical energy product.

In some embodiments, the adjustments to the position of the nozzle 385 may be executed based on a manual operator input, e.g., at the user interface of the remote controller 314. In additional or alternative embodiments, the adjustments to the position of the conduit assembly 383 may be automatically adjusted, e.g., based on feedback from one or more sensors and/or data received via the wireless network 312. As an example, one or both of the first and second free-floating bodies 301, 350 may include an accelerometer (e.g., an inertial measurement unit; not shown) configured to gather changes in local positional data, e.g., resulting from water wave motions. As an additional or alternative example, one or both of the first and second free-floating bodies 301, 350 may include a global positioning system (not shown) configured to gather geographic positional data. As an additional or alternative example, one or both of the first and second free-floating bodies 301, 350 may include a wind speed sensor (not shown) configured to measure wind speed. As an additional or alternative example, such data (e.g., the positional data and/or the wind speed) may be received via the wireless network 312, in addition to other data such as meteorological data (e.g., water wave height, direction of water wave propagation, water wave period, weather, etc.). In some embodiments, directions and magnitudes of applied forces may be inferred based on the feedback from the one or more sensors and/or the data received via the wireless network 312, such that specific operational parameters (e.g., the one or more continuously adjustable parameters) may be adjusted responsive such that changes in individual applied forces may be accounted for with specificity.

In the embodiment shown in FIG. 22, a first energy product 308 is generated at the first free-floating body 301 and subsequently converted to a second energy product 309 on the second free-floating body 350. The energy conversion process from the first energy product 308 to the second energy product 309 may be similar to any of the conversion processes described in greater detail herein. For example, a reaction of H2 gas (a first energy product 308 generated on the first free-floating body 301) with CO2 gas (a precursor generated on the second free-floating body 350) may produce methanol (a second energy product 309). The second energy product 309 may be stored in the chamber 355 in some embodiments. The CO2 gas may be formed in degassing chambers 353 and 354 (with the inclusion of HCl form a storage tank 393), as described in greater detail herein. The second energy product 309 is transported to land 318. That is, the second energy product 309 may not undergo any subsequent processing after it has been produced. However, in other embodiments, the second energy product 309 may be further processed in order to generate an alternative product before reaching land 318 (or near land). For example, the second energy product 309 may be filtered, compressed (e.g., from gas to liquid), used in a reaction as a precursor, or otherwise processed before reaching land 318 or near land.

Figure 23:
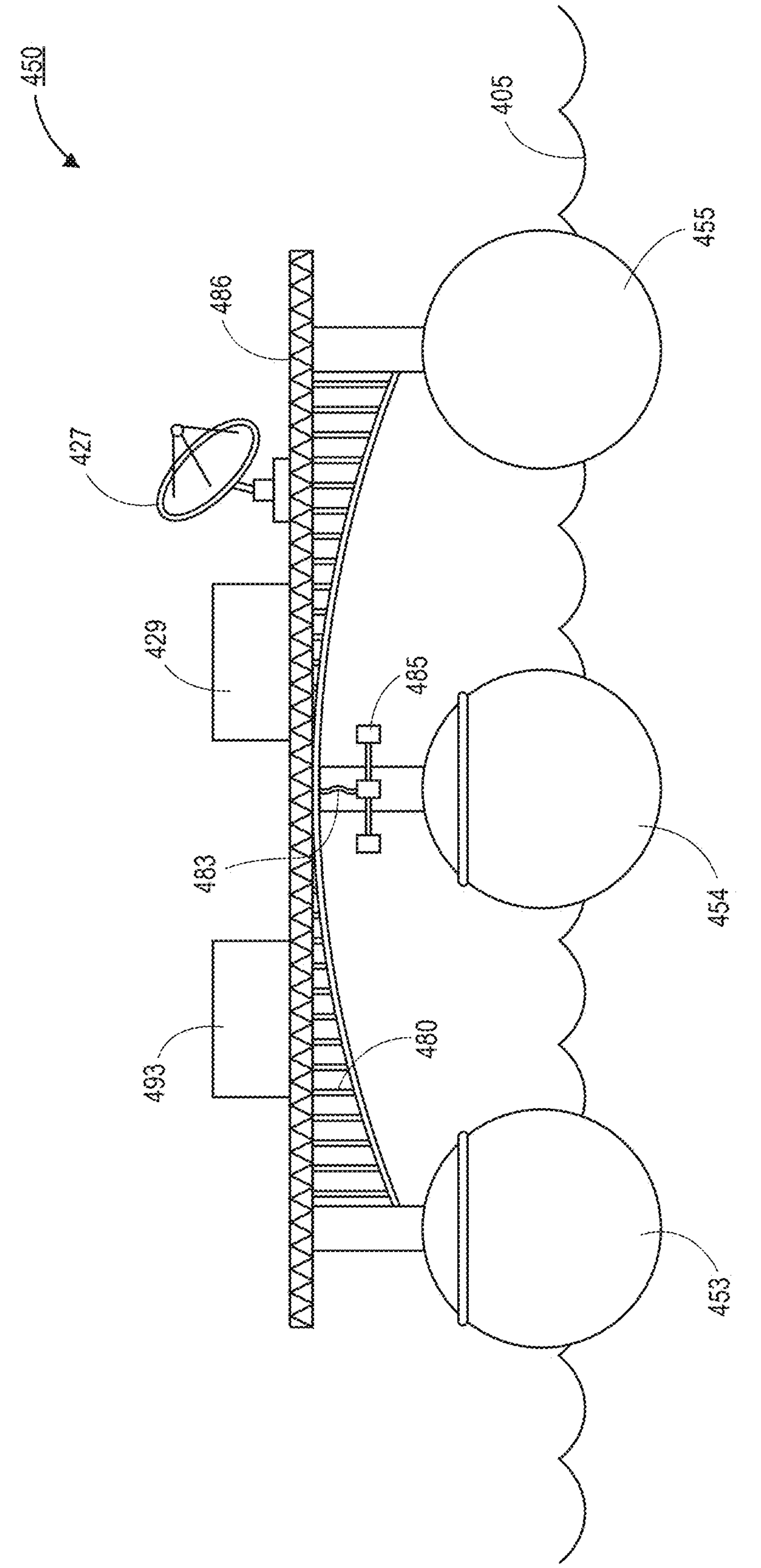
FIG. 23 is a side view of a transport vessel with a computing system and a wireless communications system.

FIG. 23 is a side view illustration of a transport vessel 450. The transport vessel 450 may comprise a first degassing chamber 453, a second degassing chamber 454, and a methanol ballast chamber 455. The chambers 453-455 may be fluidly connected to each other, as described herein. The chambers 453-455 may be mechanically coupled to each other by a structure 486 (e.g., a deck or platform) that is supported by reinforcing members 480, or the like. The chambers 453-455 may be positioned at vertices of a triangle in order to provide a stable base to support the structure 486 on the surface 405 of the body of water. The first degassing chamber 453 and the second degassing chamber 454 may be used to process seawater in order to extract CO2 gas. The first degassing chamber 453 may be used to remove N2 and O2 gas from the seawater. The processed seawater may then be degassed in the second degassing chamber 454 by lowering a pH of the seawater through the application of HCl from a storage tank 493. The CO2 gas from the second degassing process may be reacted with H2 obtained from a WEC (not shown) by a nozzle 485 and conduit 483 to form methanol that is stored in chamber 455. The reaction process may be similar to any of the reaction processes described in greater detail herein.

In an embodiment, the H2 gas is obtained from a single WEC and used in the reaction as it is being transferred onto the vessel 450. That is, there may not be a dedicated chamber for storing H2 gas. In other embodiments, the H2 gas is stored in a chamber (not shown) on the vessel 450 and used in a chemical reaction at a subsequent time. This may allow for H2 to be harvested from multiple WECs to provide a larger amount of H2 for the reaction. Similarly, the HCl may be removed from a WEC and used at the time of harvesting so that there is no dedicated chamber for storing HCl. In other embodiments, one or more WECs may be harvested for HCl, and the HCl is stored in chamber 493 for subsequent use. The HCl may also be a precursor that is periodically supplied to the vessel 450 from another vessel or source of HCl.

The vessel 450 may also comprise a computing system 429 and one or more antennas 427. A housing may protect the computing system 429 from environmental conditions. The computing system 429 and the one or more antennas 427 may be powered by any suitable source of electrical power. For example, a hydrogen fuel cell or other fuel cell construction may be used in order to convert H2 gas (received from WECs) into electrical power. Though, other sources of power (e.g., batters, generators, etc.) may also be used in some embodiments. The computing system 429 may include any number of components, such as processors, memories, control interfaces, and the like. The computing system 429 may be configured with a plurality of processing systems integrated with each other in order to perform complex computer processing operations. The computing system 429 may be optimized and/or configured to implement one or more of data center hosting, implementing block-chain mining, training ML or AI algorithms, or the like. The outcome of the computational work (e.g., block-chain coins or tokens, trained algorithms, data center capacity, etc.) can be transmitted to external devices over a wireless network through one or more antennas 427, or other wireless systems. A more detailed description of a suitable computing system 429 may be provided in greater detail herein.

Figure 24:
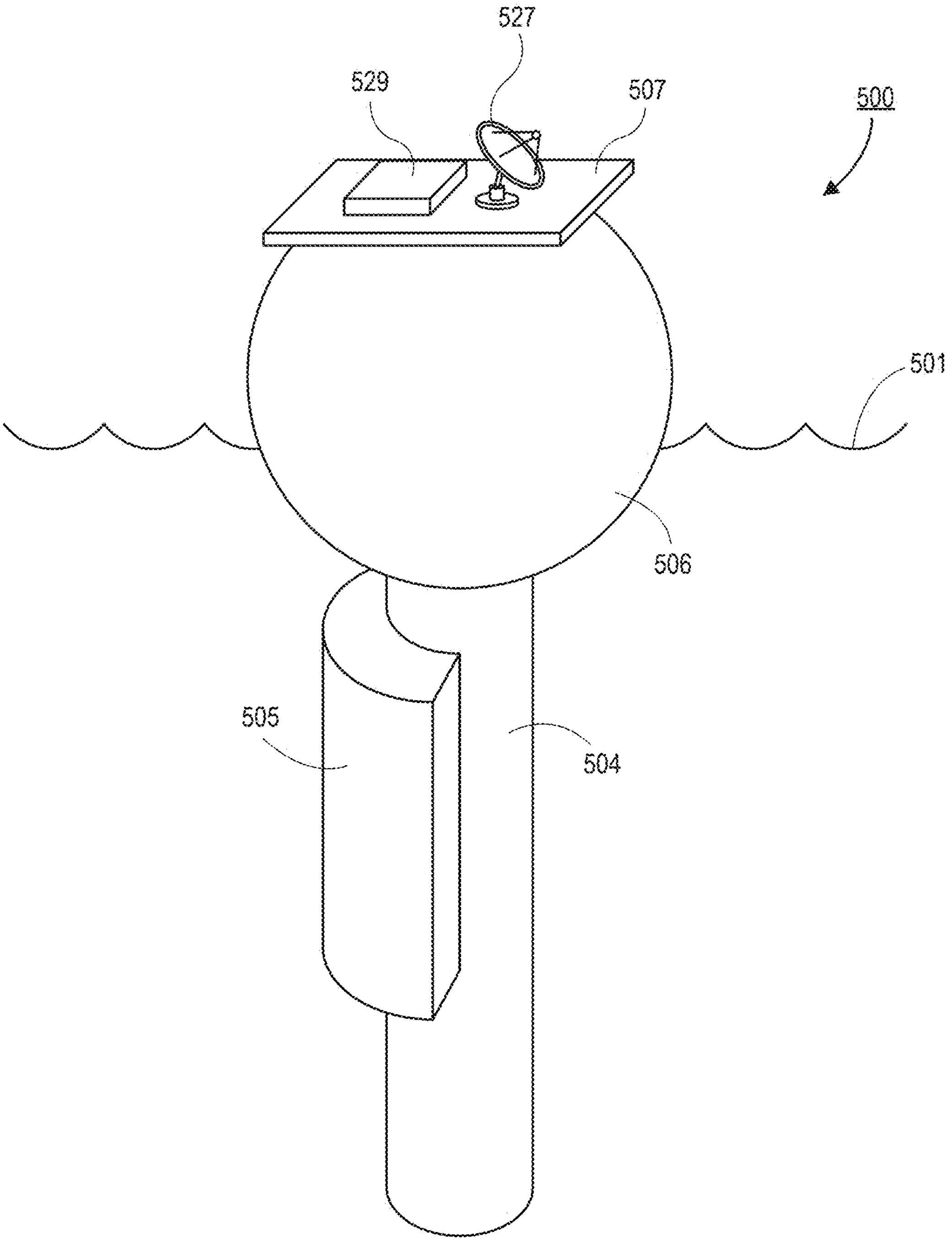
FIG. 24 is a side perspective view of a WEC with a computing system and a wireless communications system.

Referring now to FIG. 24 a side perspective view of a WEC 500 that includes a an integrated computing system 529 on a platform 507 at the top of the WEC 500 is shown, in accordance with an embodiment. The WEC 500 floats adjacent to an upper surface 501 of a body of water over which waves tend to pass. The WEC 500 comprises a hollow buoyant chamber 506, and/or buoy. In an embodiment a tube 504 is coupled to the buoyant chamber 506.

As described in other embodiments, an energy product may be generated by way of conversion of wave energy into electrical power. In some embodiments, the energy product may be a gas or other fluid, such as hydrogen gas. In some instances, the energy product may be stored in a chamber 505 coupled to the tube 504. The energy product may also be stored in the buoyant chamber 506, in a chamber (not shown) on the platform 507, or any other location of the WEC 500. In an embodiment, the energy product generated by the WEC 500 may be offloaded by a vessel similar to any of the vessels described in greater detail herein. For example, the vessel may harvest the energy product from the WEC 500 and convert the energy product into a different energy product similar to processes described in greater detail herein.

In an embodiment, the platform 507 may be provided over a top of the buoyant chamber 506. A computing system 529 may be provided on the platform and include an enclosure to protect components from water and the elements. Any number of computational systems (e.g., processors, graphics processors, etc.), memories, and/or the like may be housed within the enclosure. The computing system 529 may be configured with a plurality of processing systems integrated with each other in order to perform complex computer processing operations. The computing system 529 may be optimized and/or configured to implement one or more of data center hosting, implementing block-chain mining, training ML or AI algorithms, or the like. The outcome of the computational work (e.g., block-chain coins or tokens, trained algorithms, data center capacity, etc.) can be transmitted to external devices over a wireless network through one or more antennas 527, or other wireless systems. The computing system 529 may be powered by energy generated by the WEC 500 through conversion of wave energy into electrical power, or through conversion of the energy product stored in a chamber back into electrical power (e.g., through the use of a hydrogen fuel cell or the like).

Figure 25:
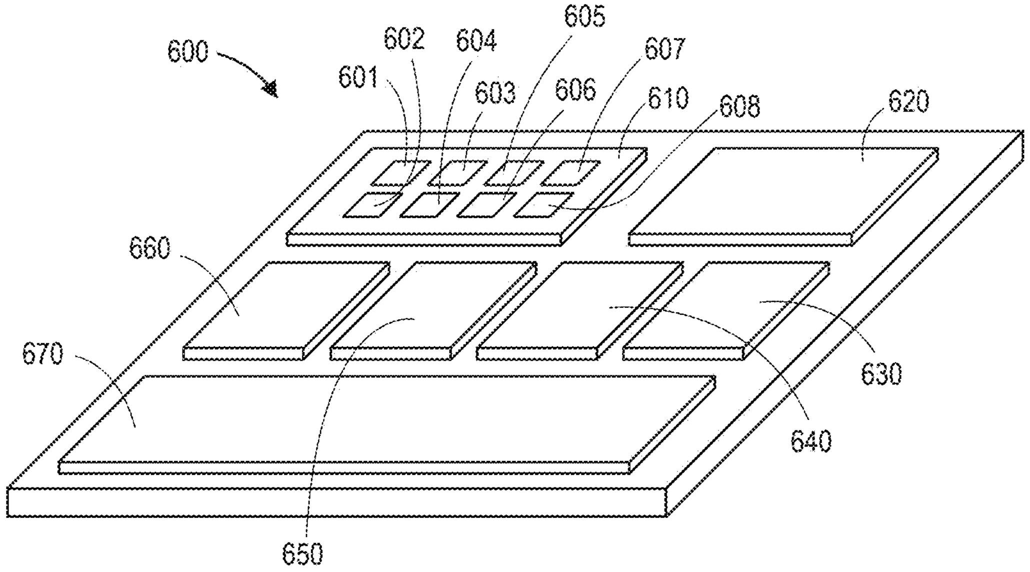
FIG. 25 is a perspective view illustration of a computing system suitable for use on a transport vessel or a WEC.

Referring now to FIG. 25 a perspective view of an computing system 600 that may be integrated with a WEC or a vessel, such as those described in greater detail herein, is shown, in accordance with an embodiment. For example, the computing system 600 may be used as the computing system 429 in FIG. 23 or computing system 529 in FIG. 24. The computing system 600 may comprise an array of electronics, hardware, and/or software that are configured to control one or more aspects of the wave-energy generation device. While the components illustrated in FIG. 25 are shown on a single board, it is to be appreciated that components may be on separate boards, structures, or the like. The computing system 600 may be housed within a water tight chamber or enclosure provided on the WEC or the vessel.

Computing system 600 may comprise a computing device 610. The computing device 610 houses a board. The board may include a number of components, including but not limited to a processor 601. The processor 601 may include, but is not limited to, a central processing unit (CPU), a graphics processing unit (GPU), an application-specific integrated circuit (ASIC), a field programmable gate array (FPGA), and/or the like. The processor 601 is physically and electrically coupled to the board. Other components of computing device 610 include, but are not limited to, memory 602 and/or 603, such as volatile memory (e.g., DRAM), non-volatile memory (e.g., ROM), flash memory, a mass storage device (such as hard disk drive, compact disk (CD), digital versatile disk (DVD), and so forth). The computing device may comprise a communications chipset 604, a digital signal processor 605, a chipset 606, an antenna 607, and/or an input/out device 608.

Computing system 600 may comprise a communications device 620. The communications device 620 enables wireless communications for the transfer of data to and from the computing system 600. The term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some embodiments they might not. The communications device 620 may implement any of a number of wireless standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, derivatives thereof, as well as any other wireless protocols that are designated as 3G, 4G, 5G, and beyond. The computing system 600 may include a plurality of communications devices 620. For instance, a first communications device 620 may be dedicated to shorter range wireless communications such as Wi-Fi and Bluetooth and a second communications device 620 may be dedicated to longer range wireless communications such as GPS, EDGE, GPRS, CDMA, WiMAX, LTE, Ev-DO, and others. The communications device 620 may be communicatively coupled to one or more antennas, satellite dishes, or other device to broadcast and/or receive wireless communications. The antennas or the like may be external to the enclosure, or the antennas may be within the enclosure.

Computing system 600 may also comprise a server rack 630. The server rack 630 may comprise a plurality of processors with associated hardware and software. The server rack 630 may execute computational work in order to provide a revenue generating service. The server rack 630 may be powered through energy generated by the WEC or stored on the vessel, such as those described in greater detail herein. While a constant power supply may be desired, computing system 600 may still function with an intermittent or non-constant power supply provided by wave-energy generation. To deal with the variable power supply, server rack 630 may include controllers that adjust clock speed for the processors. This allows for power consumption to be directly controlled to coincide with available power. In some instances, the server rack 630 may perform data center operations or tasks. The server rack 630 may host and/or deliver content, or otherwise provide a link between consumers and centralized data storage. In some instances, the server rack 630 may perform services in conjunction with block-chain technologies, such as cryptocurrency mining. The server rack 630 may perform services such as ML or AI training as well.

Computing system 600 may include a positioning system 640. The positioning system 640 may include one or more modules, components, and/or apparatuses for determining a geolocation of the wave-energy generation device. In some instances, the positioning system 640 may comprise a GPS, a compass, an accelerometer, a gyroscope, and/or the like. The positioning system 640 may include a processor and/or controller to enable navigation for the wave-energy generation device. For example, actuators may be controlled in order to steer or direct the wave-energy generation device in a particular direction. Propulsion devices (e.g., propellers, water jet flows, etc.) on the WEC or vessel may also be powered and/or directed by components of the positioning system 640.

Computing system 600 may include a sensor module 660. The sensor module 660 may include processors, memory, and associated hardware and software to control and/or record data from one or more sensors that monitor various aspects of the WEC. Sensors may comprise, but are not limited to, a pressure sensor, a gas composition sensor, a water level sensor, a temperature sensor, a fluid flow rate sensor, an electrical current sensor, a power sensor, a camera, an optical sensor, or the like. The physical sensors may be distributed throughout the WEC, and the controlling circuitry/software may be provided in the sensor module 660 within the computing system 600.

Computing system 600 may include an interface module 650. The interface module 650 may comprise one or more components used to interface with the wave-energy generation device. The interface module 650 may include one or more input devices. For example, a keyboard, a mouse, a touchscreen display, or the like may be provided in the interface module 650. Output devices, such as a display screen, a speaker, or the like may also be provided in the interface module 650. The interface module 650 may further comprise a camera, a video camera, a biometric screening device, or the like.

Computing system 600 may include a battery module 670. The battery module 670 may include any type of battery. The battery may include a rechargeable battery, such as a lithium based battery (e.g., a lithium-ion battery). The battery of the battery module 670 may be charged by electricity generated by the WEC or vessel. The battery module 670 may be used as a store of power in order to power one or more electrical components of the embodiment 600, or any other powered device of the wave-energy generation device. The battery module 670 may be used in order to normalize power delivery to electrical components. For example, the battery module may supply power in order to equalize total power delivery when the wave-energy generation device provides variable power over time.

Figure 26:
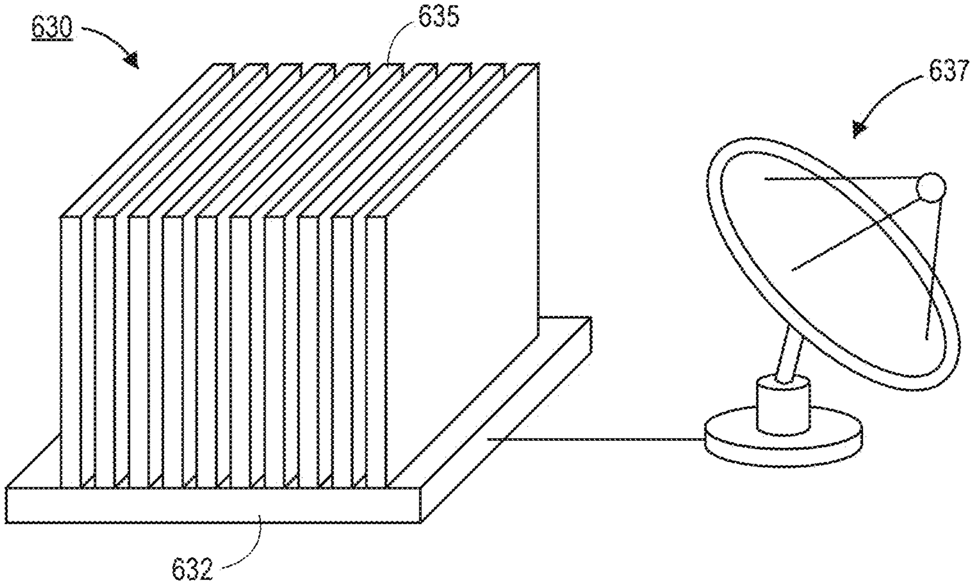
FIG. 26 is a perspective view illustration of a server system suitable for use on a transport vessel or a WEC.

Referring now to FIG. 26 a perspective view of a server rack 630 that may be integrated into a WEC or vessel, such as those described in greater detail herein. As shown, the server rack 630 may include a plurality of server blades 635 that are provided on a rack 632. The server blades 635 may be communicatively coupled to each other through the rack 632 and/or associated cabling, in order to provide enhanced processing power. The server blades 635 may include processors, such as, but not limited to, central processing units (CPUs), graphics processing units (GPUs), application-specific integrated circuits (ASICs), field programmable gate arrays (FPGAs), and/or the like.

In some instances the server rack 630 is communicatively coupled to an antenna 637 to enable wireless communication. The antenna 637 may include a parabolic dish antenna or any other antenna configuration. The ability to wirelessly transmit data from the server rack 630 allows for data to be processed remotely at the source of power generation (e.g., in the ocean) while still being useful to the end consumer. The data delivery, hosting, computation, and the like can be executed at lower energy costs using such wave-energy generation devices. Further, the server rack 630 can be passively cooled by the body of water surrounding the wave-energy generation device (e.g., the server rack 630 can be in a water tight enclosure that is submersed in water). In some instances, the server rack 630 functions as a cryptocurrency mining rig that is powered through the energy produced by the WEC or vessel.

Figure 27:
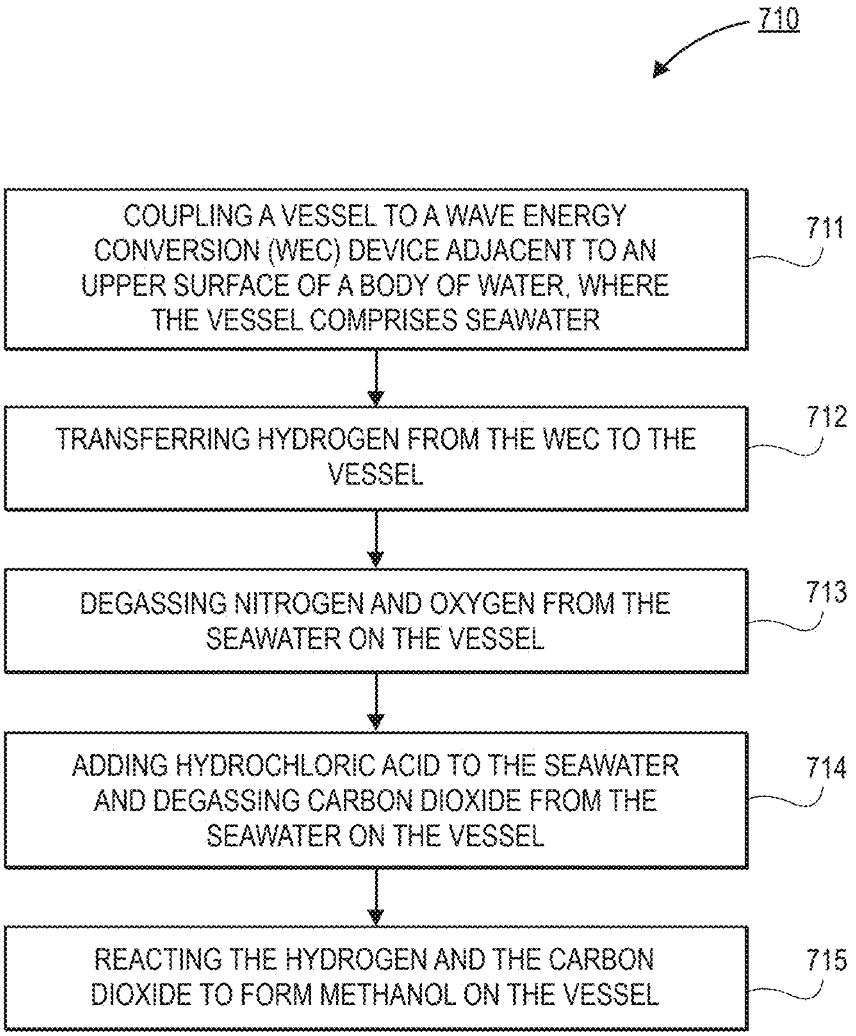
FIG. 27 is a process flow diagram of a process for extracting hydrogen from a WEC and converting the hydrogen into methanol through a reaction with carbon dioxide.

FIG. 27 is a process flow diagram of a process 710 for converting a first energy product into a second energy product. In a particular embodiment, the first energy product comprises hydrogen gas and the second energy product comprises methanol. In an embodiment, the process 710 may begin with operation 711, which comprises coupling a vessel to a wave energy conversion (WEC) device adjacent to an upper surface of a body of water. In an embodiment, the vessel comprises seawater. The seawater may be loaded onto the vessel through any suitable process, such as pumping or the like. The seawater may be stored in a first chamber.

The process 710 may continue with operation 712, which comprises transferring hydrogen from the WEC to the vessel. The hydrogen may be transferred through the use of a nozzle and conduit assembly with the nozzle fluidly connecting the WEC to the vessel. The nozzle may be controlled in up to six degrees of freedom. Since both the WEC and the vessel are floating on the same surface of the body of water, the relative motion between the WEC and the vessel is minimal, which facilitates simpler coupling. That is, the WEC and the vessel may float in a manner similar to each other since both the WEC and the vessel experience substantially the same wave patterns, currents, wind, and/or other environmental conditions. In other embodiments, multiple WECs may be harvested in order to supply a larger amount of hydrogen to the vessel.

The process 710 may continue with operation 713, which comprises degassing nitrogen and oxygen from the seawater on the vessel. The degassing operation may be implemented in the first chamber using a venturi circuit coupled to the first chamber. The nitrogen and oxygen may be vented to the environment or stored for other purposes.

The process 710 may continue with operation 714, which comprises adding hydrochloric acid to the seawater and degassing carbon dioxide from the seawater on the vessel. The carbon dioxide degassing may occur in a second chamber. The hydrochloric acid may be supplied to the second chamber from a chamber for storing hydrochloric acid provided on the vessel. The hydrochloric acid may sometimes be sourced from one or more WECs, such that hydrochloric acid is transferred to the vessel from one or more WECs.

The process 710 may continue with operation 715, which comprises reacting the hydrogen and the carbon dioxide to form methanol on the vessel. The methanol may be stored in a third chamber. The first chamber, the second chamber, and the third chamber may be buoyant chambers suitable for floating the vessel adjacent to the upper surface of the body of water. The chambers may sometimes be referred to as flotation chambers. In an embodiment, the reaction of hydrogen and carbon dioxide may be similar to any of the reaction processes described in greater detail herein.

Figure 28:
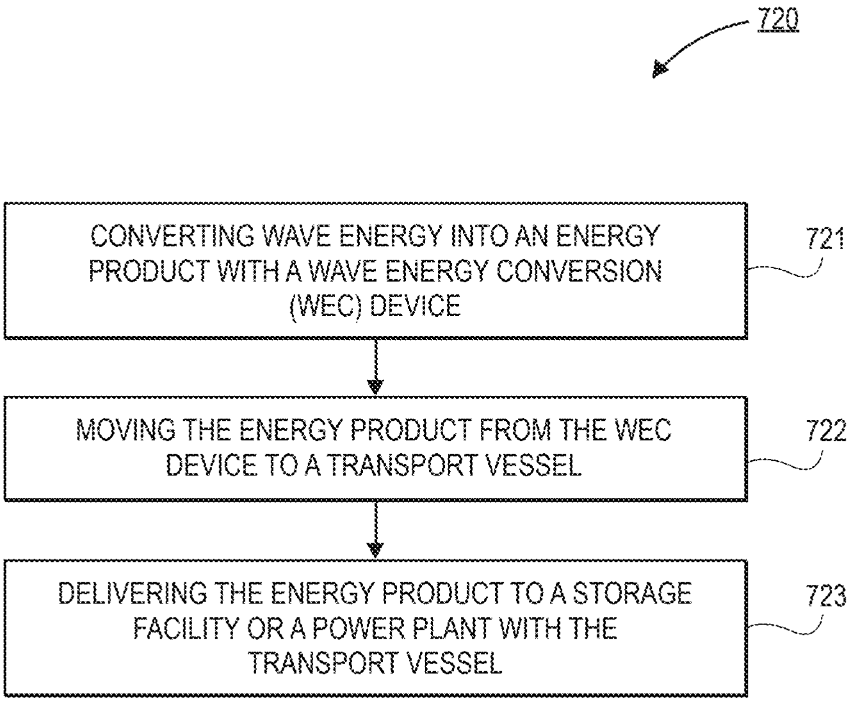
FIG. 28 is a process flow diagram of a process for transporting an energy product from a WEC to a storage facility with a transport vessel.

FIG. 28 is a process flow diagram of a process 720 for generating an energy product with a WEC and transporting the energy product to an alternative location, in accordance with an embodiment. In an embodiment, the process 720 may begin with operation 721, which comprises converting wave energy into an energy product with a WEC device. The WEC may be similar to any of the WECs described in greater detail herein. The energy product may be similar to any of the energy products described in greater detail herein. For example, the energy product may be a liquid or gas fuel (e.g., hydrogen), a chemical (e.g., HCl), a biological product (e.g., algae, fish, or any other marine species), or the like. The generation of the energy product may be made using any process described herein. For example, electrical power generated by the WEC can be used in order to produce the energy product.

In an embodiment, the process 720 may continue with operation 722, which comprises moving the energy product from the WEC to a transport vessel. The transport vessel may be similar to any vessel described herein. For example, the transport vessel may comprise a vessel that harvests the energy product from the WEC and converts the energy product into a different energy product through one or more different chemical reactions done on the vessel. In some embodiments, one or more of the precursors for one or more of the chemical reactions is generated on the transport vessel. The transport vessel is capable of controlled motion on, through, and/or over the body of water on which the WEC floats. The energy product may be delivered or moved (actively or passively) to the transport vessel through any mechanism, such as a hose, a pipe, a cable, or the like.

In an embodiment, the process 720 may continue with operation 723, which comprises moving the energy product to a storage facility or a power plant with the transport vessel. The storage facility or a power plant may be provided at a location that is different than an approximate location of the WEC. In one embodiment, the location is at land. Though, in other embodiments, the location is near land (e.g., up to 100 kilometers from land, up to 40 kilometers from land, up to 1 kilometer from land, up to 500 meters from land, or up to 50 meters from land). In other embodiments, the storage facility may be a second vessel. For example, the first vessel may take the energy product from the WEC and deliver it to the second vessel. The second vessel may then take the energy product towards shore.

Figure 29:
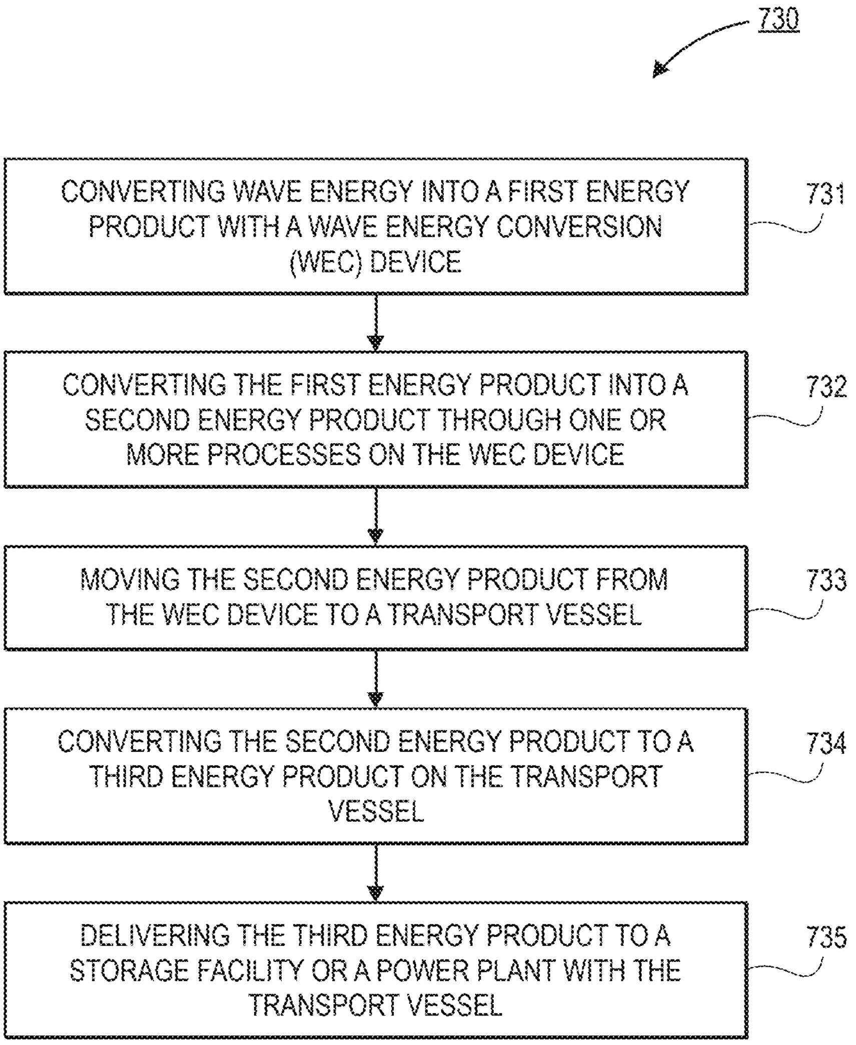
FIG. 29 is a process flow diagram of a process for converting energy products and transporting energy products with a transport vessel.

FIG. 29 is a process flow diagram of a process 730 for converting a first energy product into a third energy product and transporting the third energy product to a storage facility or power plant. In an embodiment, the process 730 may begin with operation 731, which comprises converting wave energy into a first energy product with a WEC device. The WEC may be similar to any of the WECs described in greater detail herein. The first energy product may be similar to any of the energy products described in greater detail herein. For example, the energy product may be a liquid or gas fuel (e.g., hydrogen), a chemical (e.g., HCl), a biological product (e.g., algae, fish, or any other marine species), or the like. The generation of the first energy product may be made using any process described herein. For example, electrical power generated by the WEC can be used in order to produce the energy product.

In an embodiment, the process 730 may continue with operation 732, which comprises converting the first energy product into a second energy product through one or more processes on the WEC. The conversion of the first energy product to the second energy product may include converting one type of fuel or chemical into another fuel or chemical. In one embodiment, the first energy product may comprise hydrogen, and the second energy product may be hydrochloric acid. Other conversion processes may also be used, such as, but not limited to, filtering, compression (e.g., from a gas to a liquid), purification, or the like may be used. Conversions may also include processing biological products. For example, algae may be processed into algae oil, or fish may be processed into fish oil. The conversion process may be implemented on or within the vicinity of the WEC.

In an embodiment, the process 730 may continue with operation 733, which comprises moving the second energy product from the WEC to a transport vessel. The transport vessel may be similar to any vessel described herein. For example, the transport vessel may comprise a vessel that harvests the second energy product from the WEC and converts the second energy product into a third energy product through one or more different chemical reactions done on the vessel. In some embodiments, one or more of the precursors for one or more of the chemical reactions is generated on the transport vessel. The transport vessel is capable of controlled motion on, through, and/or over the body of water on which the WEC floats. The energy product may be delivered or moved (actively or passively) to the transport vessel through any mechanism, such as a hose, a pipe, a cable, or the like.

In an embodiment, operation 733 may also comprise transferring the first energy product to the vessel as well. That is, both a first energy product and a second energy product may be provided to the transport vessel. In the case of a methanol conversion, the first energy product may comprise hydrogen, and the second energy product may comprise hydrochloric acid.

In an embodiment, the process 730 may continue with operation 734, which comprises converting the second energy product to a third energy product on the transport vessel. For example, in the case of methanol conversion, the transport vessel generates carbon dioxide through the use of hydrochloric acid in a degassing operation (as described in greater detail herein). The carbon dioxide may be reacted with the hydrogen in order to generate methanol (i.e., the third energy product), which can be stored in a chamber on the transport vessel.

In an embodiment, the process 730 may continue with operation 735, which comprises delivering the third energy product to a storage facility or a power plant with the transport vessel. The storage facility or a power plant may be provided at a location that is different than an approximate location of the WEC. In one embodiment, the location is at land. Though, in other embodiments, the location is near land (e.g., up to 100 kilometers from land, up to 40 kilometers from land, up to 1 kilometer from land, up to 500 meters from land, or up to 50 meters from land). In other embodiments, the storage facility may be a second vessel. For example, the first vessel may take the third energy product from the WEC and deliver it to the second vessel. The second vessel may then take the third energy product towards shore.

Figure 30:
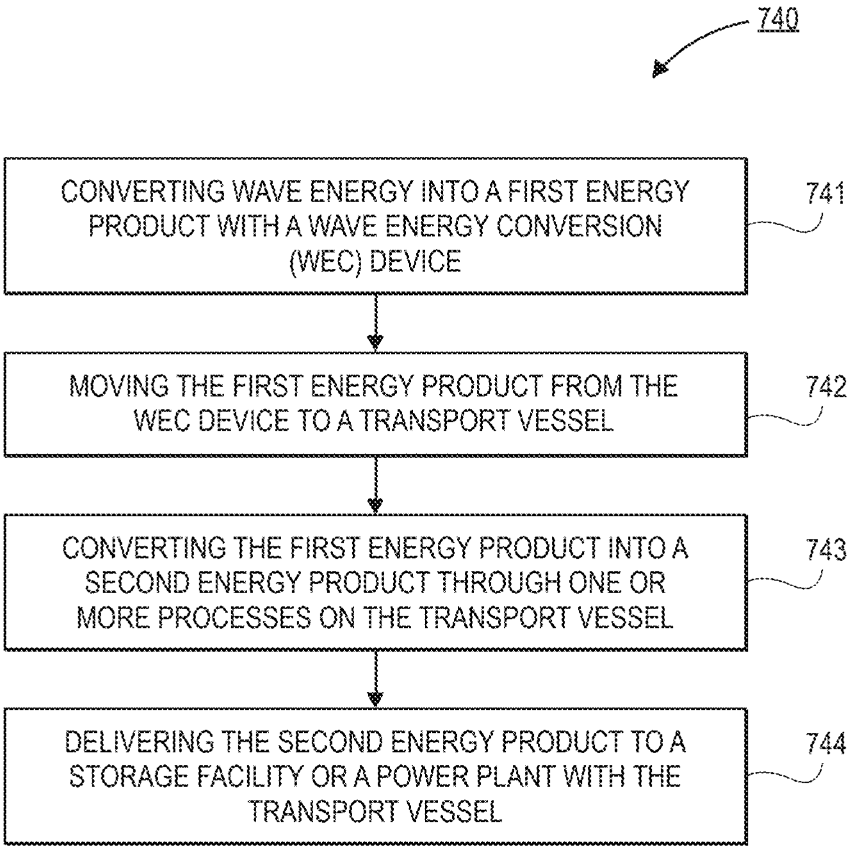
FIG. 30 is a process flow diagram of a process for converting a first energy product into a second energy product on a transport vessel and delivering the second energy product to a storage facility.

FIG. 30 is a process flow diagram of a process 740 for converting a first energy product into a second energy product and transporting the second energy product to storage facility or power plant. In an embodiment, the process 740 may begin with operation 741, which comprises converting wave energy into a first energy product with a WEC device. The WEC may be similar to any of the WECs described in greater detail herein. The first energy product may be similar to any of the energy products described in greater detail herein. For example, the energy product may be a liquid or gas fuel (e.g., hydrogen), a chemical (e.g., HCl), a biological product (e.g., algae, fish, or any other marine species), or the like. The generation of the first energy product may be made using any process described herein. For example, electrical power generated by the WEC can be used in order to produce the energy product.

In an embodiment, the process 740 may continue with operation 742, which comprises moving the first energy product from the WEC to a transport vessel. The transport vessel may be similar to any vessel described herein. For example, the transport vessel may comprise a vessel that harvests the energy product from the WEC and converts the energy product into a different energy product through one or more different chemical reactions done on the vessel. In some embodiments, one or more of the precursors for one or more of the chemical reactions is generated on the transport vessel. The transport vessel is capable of controlled motion on, through, and/or over the body of water on which the WEC floats. The first energy product may be delivered or moved (actively or passively) to the transport vessel through any mechanism, such as a hose, a pipe, a cable, or the like.

In an embodiment, the process 740 may continue with operation 743, which comprises converting the first energy product into a second energy product through one or more processes on the transport vessel. The conversion of the first energy product to the second energy product may include converting one type of fuel or chemical into another fuel or chemical. In one embodiment, the first energy product may comprise hydrogen, and the second energy product may comprise methanol. Additional precursors (e.g., CO2) may be reacted with the first energy product in order to generate the second energy product. For example, a process similar to the process described with respect to FIG. 21 may be used in some embodiments. In an embodiment, one or more additional precursors may be generated on the transport vessel. For example CO2 may be formed with a multi-step degassing operation that includes application of HCl to seawater to lower a pH of the seawater. Other conversion processes may also be used, such as, but not limited to, filtering, compression (e.g., from a gas to a liquid), purification, or the like may be used.

In an embodiment, the process 740 may continue with operation 744, which comprises delivering the second energy product to a storage facility or a power plant with the transport vessel. The storage facility or a power plant may be provided at a location that is different than an approximate location of the WEC. In one embodiment, the location is at land. Though, in other embodiments, the location is near land (e.g., up to 100 kilometers from land, up to 40 kilometers from land, up to 1 kilometer from land, up to 500 meters from land, or up to 50 meters from land). In other embodiments, the storage facility may be a second vessel. For example, the first vessel may take the energy product from the WEC and deliver it to the second vessel. The second vessel may then take the energy product towards shore.

Figure 31:
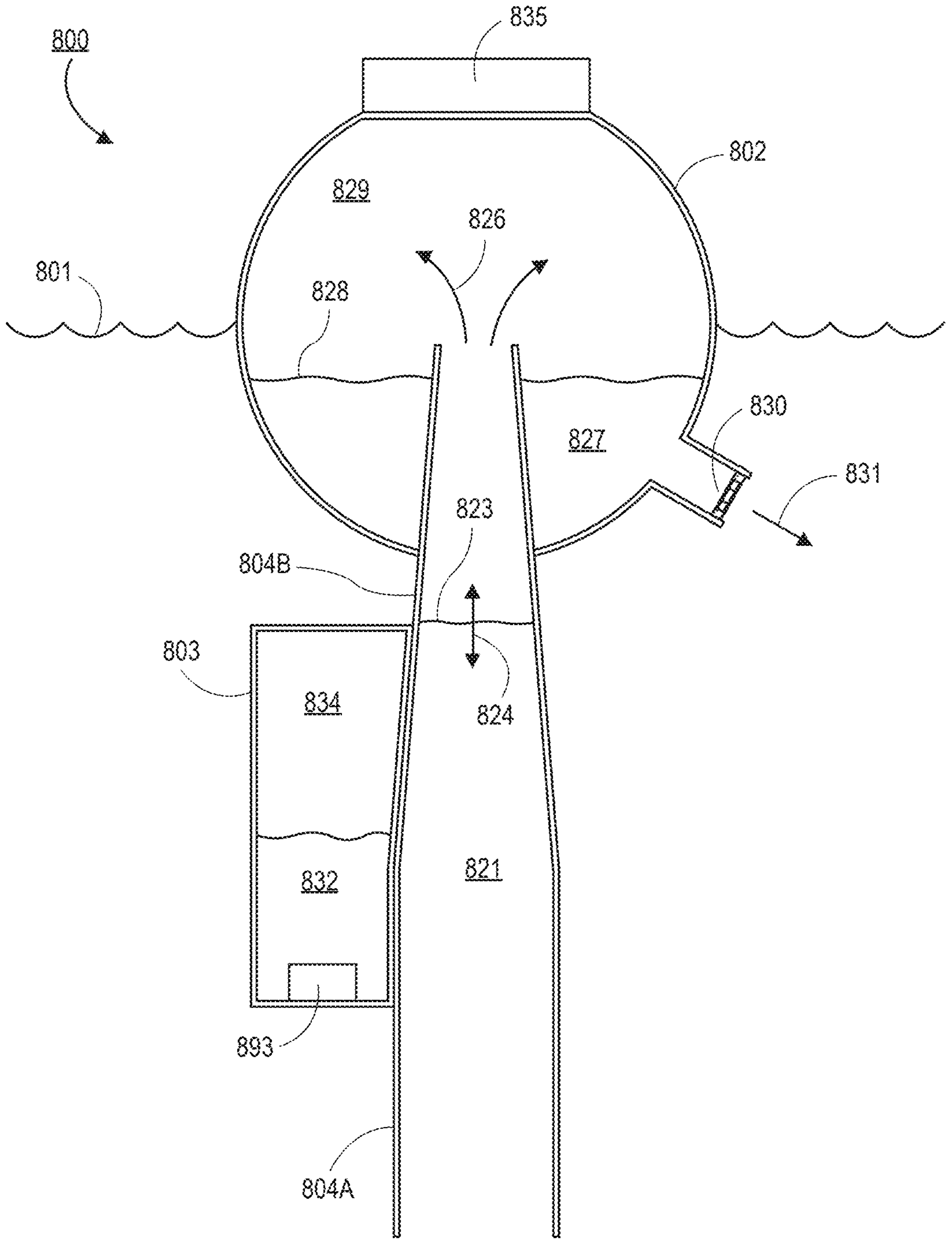
FIG. 31 is a cross-sectional illustration of a WEC for generating an energy product.

FIG. 31 illustrates a cross-sectional view of a WEC 800, in accordance with an embodiment. The WEC 800 floats adjacent to an upper surface 801 of a body of water over which waves pass. The WEC 800 may include a buoyant chamber 802 with an interior volume 829. The interior volume 829 may be partially filled with water 827. Gasses (e.g., oxygen, hydrogen, air, or the like) may fill additional portions of the interior volume 829. Internal structures may also be provided within the buoyant chamber 802. For example, baffles, walls, sub-chambers, doors, or the like may be provided within the chamber 802. The internal structures may be used to control flow or movement of water 827 within the chamber 802, provide housing for different gas species, or the like.

The chamber 802 may be axially symmetric in some instances. For example, in FIG. 31, the chamber 802 is a spherical segment with a substantially horizontal top surface. In other instances, the chamber 802 may be a spherical cap, or any other type of axially symmetric shape. Though, the chamber 802 may be non-axially symmetric in other instances. For example, the chamber 802 may have a keel or hull shape similar to that of a floating vessel (e.g., a boat or ship). Openings, ports, or the like may also be provided through the walls of the chamber 802 in order to access materials and/or substances within the chamber 802, to provide control of pressure within the chamber 802, and/or the like.

A tube 804 may be coupled to the chamber 802. The tube 804 may have an open bottom that is in fluid communication with the water surrounding the WEC 800. The tube 804 may pass through a wall of the chamber 802 and pass into the interior volume 829. An opening at the top of the tube 804 is fluidically coupled to the interior of the chamber 802. The tube 804 may have a constant diameter through its length. In other instances, the tube 804 may have a non-uniform diameter through its length. For example, the tube 804 may have a first portion 804A with a constant diameter and a second constricted portion 804B where the diameter is reduced. The tube 804 may be cylindrical or have any other shaped cross-section.

As shown, water 821 may reside in the tube 804 with a free surface 823. As indicated by the double arrow 824 across the free surface 823, the level of the oscillates up and down in response to oscillation of the WEC 800. Oscillation is driven by interaction with waves that pass along the surface 801 of the body of water. The confined water 821 within the tube 804 may acquire momentum during oscillation of the WEC 800. At some points in time, the free surface 823 rises above the top opening of the tube 804 and is expelled (as indicated by arrows 826) into the interior volume 829 of the chamber 802. The water from the tube 804 maintains a level 828 of water 827 within the chamber 802.

In order to generate energy, water 827 from the interior of the chamber 802 is expelled out a pipe. As water 827 passes through the pipe, an energy generation device 830 is engaged. The energy generation device 830 may comprise a hydropower turbine, such as a reaction turbine (e.g., a propeller turbine, a bulb turbine, a straflo turbine, a tube turbine, a Kaplan turbine, a Francis turbine, or a kinetic turbine) or an impulse turbine (e.g., a Pelton turbine, or a cross-flow turbine). In some instances, a single turbine is used for the energy generation device 830, and in other instances, multiple turbines arranged in series are used for the energy generation device 830. While a single energy generation device 830 is shown in the WEC 800, embodiments may include a plurality of energy generation devices 830.

The energy generation device 830 may be coupled to an electrical generator (not shown). The energy generation device provides rotational energy which is converted into electrical energy by the electrical generator. The electrical energy may be stored (e.g., in a battery) or consumed for one or more purposes, which will be described in greater detail herein. While an electrical generator is one option, other generator types may also be used. For example, generators described herein may include any generator, alternator, other mechanism, device, and/or component that converts energy from one form into another. In some instances, one or more of the energy generation systems may be replaced with a magnetohydrodynamic (MHD) generator, which generates electricity directly from a flow of liquid without the need for connection with a turbine and associated rotating shaft. That is, a combination of a turbine connected to a generator by a shaft can be replaced, in some instances and with an appropriate choice of working fluid, with a MHD generator.

As noted above, WEC 800 may generate significant amounts of energy that needs to be stored or used in a constructive manner. In some instances, energy generated from WEC 800 may be stored in a battery. The battery may provide an accessible energy source in order to run one or more electrical components integrated into the WEC 800. Alternatively (or in addition), WEC 800 may provide a material conversion process in order to "store" energy in a more transportable form. For example, energy generated by WEC 800 can be stored in the form of an energy product, such as those described in greater detail herein.

In the case of the energy product being hydrogen gas, an electrolyzer 893 may be provided on the WEC 800. The electrolyzer 893 may be fluidly coupled to a water source, such as water 832 within a chamber 803. Water 832 may be deionized, filtered, distilled, and/or otherwise purified. Water 832 may be provided to the WEC 800 as a precursor material. Energy generated by the WEC 800 may be consumed by the electrolyzer 893 to convert water into oxygen and hydrogen. The hydrogen gas may be stored in the internal volume 834 of the chamber 803 or any other confined space associated with the WEC 800. The oxygen gas may be vented to atmosphere. After hydrogen gas is produced, the gas may be collected (i.e., removed or off-loaded from the WEC 800) periodically be an external vessel, ship, air-ship, submersible, drone, or any other vehicle, such as a transport and reaction vessel, such as those described in greater detail herein.

WEC 800 may be an autonomous device with the ability to move and/or navigate in a controlled manner about the body of water. Propulsion of the WEC 800 may be driven through one or more different mechanisms. In one instance, the expelled water 831 out of the pipe provides a propulsive force that can move the WEC 800. The WEC 800 can be steered through control of the force of the expelled water 831 and/or the direction of the expelled water 831. In some instances, one or more rudders (not shown) can be coupled to the WEC 800 in order to provide directional control, rotational control, and/or the like.

In some embodiments, propulsion of the WEC 800 may be provided through one or more active propulsion devices. For example, propellers or the like may be used in some instances. Energy to drive the active propulsion devices may be obtained through the energy generation of the WEC 800, or from batteries that were charged through the wave-energy generation of the WEC. In other instances, hydrogen or other gasses generated on the WEC 800 can be consumed (e.g., through the use of a fuel cell) in order to power active propulsion devices.

The WEC 800 may include an enclosure 835 that is provided on the chamber 802. The enclosure 835 may be a water proof chamber for securing one or more electrical components. For example, a computing system, a positioning system, and/or a communications system may be provided in the enclosure 835. The computing system may provide one or more processors and associated hardware and/or software that enables control of the WEC 800. For example, the computing system may control power generation, such as by controlling flow rates of water to the energy generation device 830. The positioning system may include a GPS, a compass, an accelerometer, a gyroscope, or any other suitable navigational system. The positioning system may control propulsion and steering systems in order to navigate the WEC 800. The communications system may include an antenna, a receiver, and associated circuitry, hardware, and/or software. The communications system may provide a communication link to external systems, other waver-energy generation systems, or the like. The systems described in the enclosure 835 on the WEC 800 are exemplary in nature, and it is to be appreciated that many different systems, control apparatuses, and/or the like may be provided in the enclosure 835. For example, computing systems and/or servers similar to those described in greater detail with respect to FIG. 25 and FIG. 26 may be provided in the enclosure 835 in some embodiments.

Figure 32:
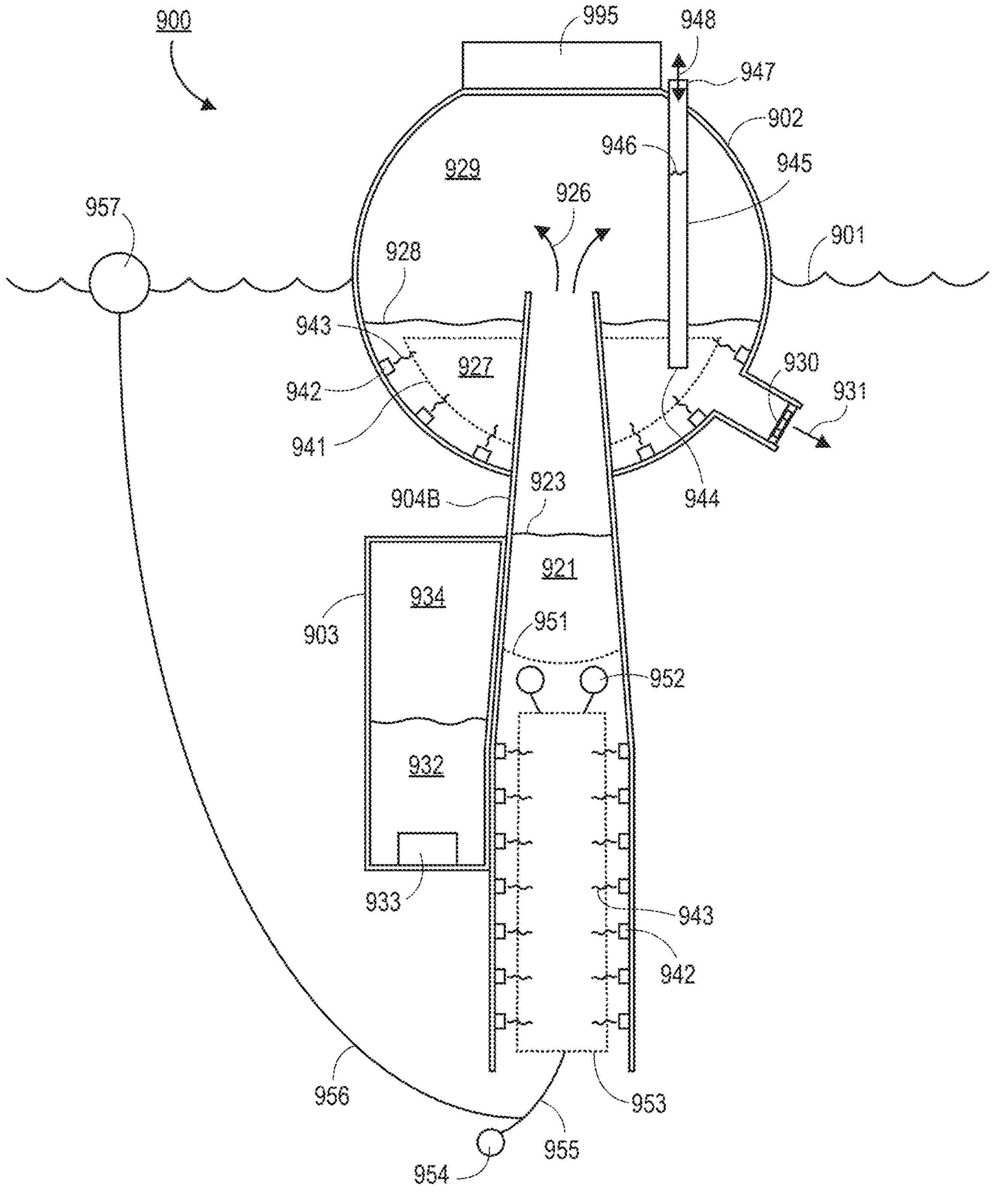
FIG. 32 is a cross-sectional illustration of a WEC for generating a biological energy product.

FIG. 32 illustrates a cross-sectional view of a WEC 900, in accordance with an embodiment. The WEC 900 may be similar to the WEC 800 described above, with the exception of the energy product that is being generated or produced by the WEC 900. For example, WEC 900 may include a buoyant chamber 902 coupled to an injection tube 904A/904B. Water 921 within the tube 904 oscillates so that the surface 923 raises and lowers within the tube 904. In some instances water 921 may flow out 926 of the tube 904 into the interior 929 of the chamber 902 in order to fill water 927 in the chamber 902. Water 927 in the chamber 902 can be expelled through energy generation device 930 and exit 931 the WEC 900 in order to generate energy. An enclosure 995 may be provided at a top of the chamber 902 for housing electronics and/or a computing system, such as those described in greater detail herein.

However, instead of producing a gas as an energy product (or only gas), the WEC 900 may produce a biological product. The biological product may comprise one or more of marine algae (e.g., micro-alae and/or macro-algae), seaweed, other marine plants, fish, krill, or other marine organisms. More specifically, electrical power generated through the operation of an energy generation device 930 can be used to power lights 942, lamps, thermal devices (e.g., heaters), and/or the like. For example, lights 942 may be light emitting diode (LED) lights or any other suitable source for generating electromagnetic radiation 943. The electromagnetic radiation 943 can be consumed by the biological product within the WEC 900 in order to induce growth of the biological product.

As shown in FIG. 32, the lights 942 may be arranged, attached, or otherwise coupled to interior surfaces of the chamber 902. Additionally, lights 942 may be provided along sidewalls of the injection tube 904. While shown as being coupled directly to interior wall surfaces, other embodiments may comprise suspending lights 942 within an interior volume of the chamber 902. The lights 942 in FIG. 32 are all shown as being submerged in water 927 or 921.

Though, in other embodiments, lights 942 may be provided above the surface 928 of the water 927 within the chamber 902.

In one instance, designed to promote the growth of biological products (e.g., algae and/or other marine based plant life), an approximately circular net 941 spans, and/or is adjacent to, an approximately flow-normal and/or horizontal cross-section of the water reservoir 927, adjacent to the surface 928 of the water 927. Net 941 entrains the biological product within the lower portion of the water 927 thereby tending to reduce, if not prevent, the outflow and/or loss of that macroalgae through the energy generation device 930. In other embodiments, other structures (e.g. a sieve, catchment, mesh, or grating) are positioned in the path of water flow to the energy generation device 930 in order to prevent outflow or loss of biological products.

Periodically, biological products may be removed from the water 927 by a ship, platform, or other vessel. A ship may insert a suction tube into and through an access tube 945. Once inserted into and through access tube 945, an inserted suction tube can be positioned near the bottom of the embodiment's reservoir of water 927 and suck out a portion of the biological product therein. A complementary access tube (not shown), and/or a complementary channel within a single access suction tube 945, can return water to the reservoir while biological products, are being removed from the reservoir of water 927, thereby maintaining and/or preserving the original level 928 of the water 927 in the reservoir.

The access tube 945 allows algae, water, nutrients, and/or other materials, to be added to, and/or withdrawn from, the reservoir of water 927 when that reservoir is otherwise sealed inside the chamber 902. Because the access tube is open to the atmosphere (as indicated by arrow 948) at its upper mouth 947, and open to the water and biological product in the water 927 at its lower mouth 944, water 927 from the reservoir is free to rise up within the algae access tube 945. Because of the pressure of the air trapped within the air pocket 929 of the interior of the chamber 902, and the corresponding pressure of the water 927, the surface 946 of the water within the access tube 945 tends to rise to a height above the surface 928 of the water 927 within the reservoir whose head pressure approximately corresponds to the pressure of the air within hollow chamber 902.

In addition to growing biological products, especially macroalgae, within the water 927 reservoir inside the hollow chamber 902, biological products, especially macroalgae, may be grown inside the embodiment's injection tube 904. An upper barrier net 951 spanning an upper portion, and/or at an upper position, of the injection tube 904 prevents at least a portion of the algae within the injection tube 904 from too closely approaching the upper constricted portion of the injection tube 904 which, if not prevented, could potentially clog the injection tube 904 at that location.

Macroalgae or other biological products are grown within a net enclosure and/or containment bag 953 that forms a porous bag entraining most, if not all, of the biological products. An upper end of the algae containment bag 953 is pulled upward by a float 952, tending to position the upper end of the bag proximate to the lower side of the barrier net 951. The biological product within the containment bag 953 are encouraged to grow through the embodiment's provision of light, e.g. 943, emitted by lamps, e.g. 942, positioned along the interior wall and/or surface of the injection tube 904.

A lower end of the containment bag 953 is pulled downward by a weight 954 connected to the bag by a tether, chain, rope, linkage, and/or cable 955. Also connected to the weight 954, and therethrough to the containment bag 953, is a tether, chain, rope, linkage, and/or cable 956 an upper end of which is connected to a float 957 that tends to float at the surface 901 of the body of water on which the WEC 900 floats.

Periodically, biological products may be removed from the WEC's 900 injection tube 904 by a ship or other vessel. A ship may attach a secondary cable to cable 956 and then lower a secondary weight to increase the total weight tending to pull the algae containment bag 953 down and out of the injection tube 904. After the containment bag 953 has been pulled down and become free of the injection tube 904, the containment bag 953 may be pulled up by the secondary cable and therewith lifted onto and/or into the ship where its biological products may be harvested. The same containment bag 953 that was removed may be reinserted into the injection tube 904 using the same second cable, using an underwater autonomous vehicle, and/or using another method, mechanism, and/or system. If the same containment bag 953 is reinserted into the embodiment's inertial water tube 904, it will tend to be so reinserted after most, but not all, of its entrained biological product has been harvested and/or removed. By leaving a portion of the biological product in the containment bag 953, the residual biological product can grow and give rise to another harvest. If a "new" second containment bag 953 is inserted into the embodiment's injection tube 904 to replace the removed containment bag 953, then it is advantageous to first "seed" that containment bag 953 with biologic stock so that a new crop of a preferred species of algae can be grown.

The scope of the present disclosure includes a complementary ship to periodically harvest the biological products grown within the embodiment, as well as the facilities on a shore, floating platform, and/or other ship where the harvested algae are processed and/or stored, as well as a method for harvesting biological products wherein: a wave energy converter of a type herein disclosed is deployed on a body of water; electrical energy produced by said wave energy converter operating in waves is used to power LEDs, or other lamps, or other sources of light emissions, that are mounted on, within, inside, or outside, of said wave energy converter, and/or LEDs, or other lamps, or other sources of light emissions, that are suspended from walls, surfaces, and/or structural members, within, inside, or outside, of said wave energy converted; biological products are permitted to grow in an enclosure, cavity, or vicinity of said wave energy converter using light from said lamps as a source of metabolic energy; said biological products (or products or byproducts produced therefrom, e.g. algal oil, fish oil, etc.) is transferred to a ship or other floating vessel; said ship or floating vessel transfers said biological products (or products or byproducts produced therefrom, e.g. algal oil, fish oil, etc.) to a shore facility for processing and/or storage.

The aquaculture configuration embodiment illustrated in FIG. 32 may also include fish within either or both of the water 927 reservoir and/or the algal containment bag 953. If one or more species of fish that are able to eat and/or consume the type(s) of algae being grown within the embodiment are selected and included within the respective growth areas prior to each growth cycle, then a portion of those fish may be harvested along with whatever algae remains uneaten. The scope of the present disclosure includes a method for harvesting fish wherein: a wave energy converter of a type herein disclosed is deployed on a body of water; electrical energy produced by said wave energy converter is used to power LEDs, or other lamps, or other sources of light emissions, that are mounted on, within, inside, or outside, of said wave energy converter, as well as LEDs, or other lamps, or other sources of light emissions, that are suspended from walls, surfaces, and/or structural members, within, inside, or outside, of said wave energy converter; algae are permitted to grow in an enclosure, cavity, or vicinity of said wave energy converter using light from said lamps as a source of metabolic energy; fish or other marine organisms are permitted to grow in an enclosure, cavity, or vicinity of said wave energy converter, feeding, at least in part, on said algae as a source of metabolic energy; said fish or other marine organisms are transferred to a ship or other floating vessel; said ship or floating vessel transfers said fish and/or other marine organisms (or products or byproducts produced therefrom, e.g. fish meal or fish oil) to a shore facility for processing and/or storage.

The scope of the present disclosure includes, but is not limited to, the growth and/or harvesting of any and every kind of microalgae, macroalgae, fish, or crustacean. Fish that do not eat the varieties of algae grown may nonetheless receive nutrition, e.g. plankton and phytoplankton, from the water that is regularly introduced to the reservoir of water 927 and injection tube 904 as a result of wave action. In addition to introducing potentially nutrient-rich water from outside the embodiment into the water 927 reservoir and injection tube 904 as a result of wave action, the embodiment also tends to remove waste-containing and/or nutrient-depleted, water from the water 927 reservoir and injection tube 904 as a result of the same water cycle (i.e. water enters tube 904, and therefrom enters the water 927 reservoir, and thereafter flows out of the water reservoir through the energy generation device 930.

The scope of the present disclosure includes embodiments utilizing water reservoir lamps and/or inertial water tube lamps emitting light of any single wavelength, any range of wavelengths, and/or any combinations of wavelengths or ranges of wavelengths.

The scope of the present disclosure includes embodiments in which lamps are attached to the inner surface of the upper portion of the hollow chamber 902, i.e. within the air pocket 929. The scope of the present disclosure includes embodiments in which lamps are attached to the outer surfaces of the hollow chamber 902 and/or injection tube 904 thereby encouraging biological product growth, and the establishment of communities of fish or other marine life, outside the WEC 900, but in the vicinity of the WEC 900.

In addition to the generation of biological energy products, energy products such as hydrogen gas can be produced by an electrolyzer 933 on the WEC 900. The electrolyzer 933 may be fluidly coupled to a water source, such as water 932 within a chamber 903. Water 932 may be deionized, filtered, and/or otherwise purified. Water 932 may be provided to the WEC 900 as a precursor material. Energy generated by the WEC 900 may be consumed by the electrolyzer 933 to convert water into oxygen and hydrogen. The hydrogen gas may be stored in the internal volume 934 of the chamber 903, or any other confined space associated with the WEC 900. The oxygen gas may be vented to atmosphere. After hydrogen gas is produced, the gas may be collected (i.e., removed or offloaded from the WEC 900) periodically be an external vessel, ship, air-ship, submersible, drone, or any other vehicle.

While the foregoing disclosure has described various embodiments, it is understood that the invention is not limited to any specific embodiment or depiction herein. A person of ordinary skill in the art would readily appreciate modifications and substitutions herein, and the scope of the invention includes all such modifications and substitutions. Accordingly, the scope of the invention should not be construed to be limiting by the foreign description except where expressly so stated, but rather the invention's scope is properly determined by the appended claims, using the common and ordinary meanings of the words therein consistent with, but not limited by, the descriptions and figures of this disclosure.

EXAMPLES

Example 1: a vessel for floating and traveling adjacent to an upper surface of a body of water, the vessel comprising: a support structure; a first floatation chamber coupled to the support structure; a second floatation chamber coupled to the support structure, the second floatation chamber laterally spaced apart from and fluidly coupled to the first floatation chamber; a third floatation chamber coupled to the support structure, the third floatation chamber laterally spaced apart from the first floatation chamber and from the second floatation chamber; and a robot system coupled to the support structure, the robot system comprising an end effector, and a nozzle head coupled to the end effector.

Example 2: the vessel of Example 1, wherein the first floatation chamber is a first degassing chamber.

Example 3: the vessel of Example 2, wherein the second floatation chamber is a second degassing chamber.

Example 4: the vessel of Examples 1-3, wherein the third floatation chamber is a chemical storage chamber.

Example 5: the vessel of Examples 1-4, wherein the first floatation chamber is a first degassing chamber, the second floatation chamber is a second degassing chamber, and the third floatation chamber is a chemical storage chamber.

Example 6: the vessel of Examples 1-5, wherein one or more of the first floatation chamber, the second floatation chamber, or the third floatation chamber has a spherical shape.

Example 7: the vessel of Examples 1-6, wherein the first floatation chamber, the second floatation chamber, and the third floatation chamber form vertices of a triangle.

Example 8: the vessel of Examples 1-7, wherein one or more of the first floatation chamber or the second floatation chamber comprises a venturi circuit.

Example 9: the vessel of Examples 1-8, wherein the robot system further comprises a composite hose coupled to the nozzle head.

Example 10: the vessel of Example 9, wherein the composite hose comprises a plurality of tubes.

Example 11: the vessel of Example 10, wherein one of the plurality of tubes comprises an inner tube coaxially within an outer tube.

Example 12: the vessel of Examples 1-11, wherein the nozzle head is configured for coupling to a wave energy conversion (WEC) device.

Example 13: the vessel of Example 12, wherein the nozzle head comprises a tooling feature for coupling a port of the nozzle head to a nozzle of the WEC device.

Example 14: the vessel of Examples 1-13, wherein the robot system further comprises a plurality of cables to move, position, or orient the nozzle head in six degrees of freedom.

Example 15: the vessel of Examples 1-14, wherein the support structure comprises one or more structures selected from the group consisting of a beam, a truss, and a girder.

Example 16: the vessel of Examples 1-15, further comprising a platform coupled to the support structure.

Example 17: the vessel of Example 16, further comprising a chemical storage tank coupled to the platform.

Example 18: a method comprising: coupling a vessel to a wave energy conversion (WEC) device adjacent to an upper surface of a body of water, the vessel comprising a support structure, a first floatation chamber coupled to the support structure, a second floatation chamber coupled to the support structure, the second floatation chamber laterally spaced apart from and fluidly coupled to the first floatation chamber, a third floatation chamber coupled to the support structure, the third floatation chamber laterally spaced apart from the first floatation chamber and from the second floatation chamber, and a robot system coupled to the support structure, the robot system comprising an end effector, and a nozzle head coupled to the end effector, the coupling comprising connecting the nozzle head of the vessel to a nozzle of the WEC; transferring a chemical from the WEC to the vessel; and at least one of (i) storing the chemical on the vessel, or (ii) forming a chemical fuel on the vessel using the chemical, or (iii) dispensing the chemical from the vessel to a location beneath the upper surface of the body of water.

Example 19: the method of Example 18, wherein the chemical comprises H2.

Example 20: the method of Examples 18-19, wherein the chemical comprises HCl.

Example 21: the method of Examples 18-20, comprising the storing the chemical on the vessel.

Example 22: the method of Examples 18-21, comprising the forming the chemical fuel on the vessel using the chemical.

Example 23: the method of Example 22, comprising storing the chemical fuel in one of the first floatation chamber, the second floatation chamber, or the third floatation chamber of the vessel.

Example 24: the method of Examples 18-23, comprising the dispensing the chemical from the vessel to a location beneath the upper surface of the body of water.

Example 25: a method of forming methanol, the method comprising: coupling a vessel to a wave energy conversion (WEC) device adjacent to an upper surface of a body of water, the vessel having seawater therein; transferring hydrogen from the WEC to the vessel; and while the vessel is floating on the body of water, degassing nitrogen and oxygen from the seawater on the vessel, then adding hydrochloric acid to the seawater on the vessel, then degassing carbon dioxide from the seawater on the vessel, and then reacting the hydrogen and the carbon dioxide to form methanol on the vessel.

Example 26: the method of Example 25, further comprising: transferring hydrochloric acid from the WEC device to the vessel.

Example 27: the method of Examples 25-26, further comprising: storing the methanol in a floatation chamber of the vessel.

Example 28: the method of Examples 25-27, wherein the degassing the nitrogen and oxygen from the seawater is performed in a floatation chamber of the vessel.

Example 29: the method of Example 28, wherein the degassing the carbon dioxide from the seawater is performed in a second floatation chamber, the second floatation chamber fluidly coupled to the floatation chamber.

Example 30: a vessel for floating and traveling adjacent to an upper surface of a body of water, the vessel configured to collect liquids, gasses or other chemical products from a wave energy conversion (WEC) apparatus via a transfer apparatus, and store or process said liquids, gasses or other chemical products, the vessel configured to, when at rest, drift adjacent to the upper surface of the body of water over which waves pass in a manner similar to that of the WEC apparatus from which it retrieves chemical products, thereby reducing complications that can otherwise arise during an attempt to couple two vessels moving out of phase as they oscillate in response to the passage of waves, and the vessel configured to deliver collected or synthesized chemical products to shore, to other vessels or to other platforms, or reintroduce portions of synthesized chemical products back into the environment.

What is claimed is:

1. A method of coupling a vessel to a wave energy conversion (WEC) device, the method comprising:
- positioning the WEC device within a footprint of the vessel, wherein the WEC device is adjacent to an upper surface of a body of water, and wherein the vessel comprises:
  - a support structure;
  - a first floatation chamber coupled to the support structure;
  - a second floatation chamber coupled to the support structure, wherein the second floatation chamber is laterally spaced apart from the first floatation chamber;
  - a third floatation chamber coupled to the support structure, wherein the third floatation chamber is laterally spaced apart from the first floatation chamber and from the second floatation chamber, and wherein the footprint of the vessel is defined by the first floatation chamber, the second floatation chamber, and the third floatation chamber;
  - a plurality of cables, wherein each of the plurality of cables comprises a first end coupled to the vessel and a second end opposite from the first end; and
  - an end effector coupled to the second ends of the plurality of cables; and
- attaching the end effector to the WEC device to form a connection between the vessel and the WEC device.

2. The method of claim 1, wherein the vessel further comprises:
- a hose coupled to the end effector, wherein a first end of the hose is fluidly coupled to the vessel; and
- a nozzle head fluidly coupled to a second end of the hose, and wherein attaching the end effector to the WEC device comprises fluidly coupling the nozzle head to the WEC device.

3. The method of claim 2, further comprising:
- transferring hydrogen to the vessel from the WEC device along the hose.

4. The method of claim 3, further comprising:
- using the hydrogen to synthesize an energy produce onboard the vessel.

5. The method of claim 2, wherein the hose comprises a plurality of isolated fluidic channels.

6. The method of claim 1, further comprising:
- mechanically coupling the end effector to a docking point on an upper surface of the WEC device.

7. The method of claim 6, wherein the end effector is magnetically coupled to the docking point.

8. The method of claim 1, further comprising:
- conveying data through the end effector from the WEC device to the vessel.

9. The method of claim 1, wherein each of the plurality of cables is coupled to one of a plurality of winches that are configured to retract and extend the plurality of cables in order to move the end effector to a desired location within the footprint of the vessel.

10. The method of claim 1, wherein the WEC device further comprises:

a plurality of target nodes, wherein the end effector is directed to the WEC device by tracking the plurality of target nodes.

11. The method of claim 10, wherein the vessel further comprises:

a plurality of cameras configured to track the plurality of target nodes.

12. The method of claim 1, wherein the plurality of cables comprises six or more cables.

13. The method of claim 1, wherein each of the plurality of cables is coupled to the support structure.

14. The method of claim 1, further comprising:

releasing tension on one or more of the plurality of cables after attaching the end effector to the WEC device.

* * * * *